US012059161B2

(12) United States Patent
Deville et al.

(10) Patent No.: US 12,059,161 B2
(45) Date of Patent: Aug. 13, 2024

(54) ASPIRATION THROMBECTOMY SYSTEM AND METHODS FOR THROMBUS REMOVAL WITH ASPIRATION CATHETER

(71) Applicant: RapidPulse, Inc., Miami, FL (US)

(72) Inventors: Derek Dee Deville, Coral Gables, FL (US); Matthew A. Palmer, Miami, FL (US); William T. Bales, Miami, FL (US); M. Sean McBrayer, Coral Gables, FL (US); Eric Petersen, Homestead, FL (US); Richard Cartledge, Boca Raton, FL (US); Thomas O. Bales, Jr., Miami, FL (US); Carlos Rivera, Cooper City, FL (US)

(73) Assignee: RapidPulse, Inc., Miami, FL (US)

( * ) Notice: Subject to any disclaimer, the term of this patent is extended or adjusted under 35 U.S.C. 154(b) by 716 days.

(21) Appl. No.: 16/899,514

(22) Filed: Jun. 11, 2020

(65) Prior Publication Data

US 2020/0297362 A1    Sep. 24, 2020

Related U.S. Application Data

(63) Continuation of application No. 16/681,564, filed on Nov. 12, 2019, now Pat. No. 10,722,253, and a
(Continued)

(51) Int. Cl.
*A61B 17/22* (2006.01)
*A61B 17/00* (2006.01)
(Continued)

(52) U.S. Cl.
CPC .............. *A61B 17/22* (2013.01); *A61F 2/013* (2013.01); *A61M 25/0075* (2013.01);
(Continued)

(58) Field of Classification Search
CPC ................ A61B 17/22; A61B 17/3207; A61B 2017/00022; A61B 2017/22079;
(Continued)

(56) References Cited

U.S. PATENT DOCUMENTS 4,164,223 A  8/1979 Munib
4,315,506 A  2/1982 Kayser et al.
(Continued)

FOREIGN PATENT DOCUMENTS

CN  101027004 A  8/2007
EP  1799128 B1  3/2010
(Continued)

OTHER PUBLICATIONS

International Search Report and Written Opinion for patent application PCT/US2019/42546 dated Oct. 7, 2019.
(Continued)

*Primary Examiner* — Wade Miles
(74) *Attorney, Agent, or Firm* — Perkins Coie LLP

(57) ABSTRACT

A clot removal system comprises a catheter, a vacuum source, and a controller. The catheter comprises a proximal end, a distal end, and controller operating parameters and defines a lumen configured to be filled with a liquid column having a proximal portion. The vacuum source is configured to supply vacuum. The controller is configured to carry out a control pattern of turning on and off the vacuum based upon the controller operating parameters and is configured to receive the controller operating parameters in an automatic response to the catheter being operatively connected to at least one of the vacuum source and the controller and, responsive to the connection, to carry out the control pattern to change a level of vacuum at the distal end of the catheter.

35 Claims, 29 Drawing Sheets

Related U.S. Application Data continuation of application No. PCT/US2019/042546, filed on Jul. 19, 2019, which is a continuation of application No. 16/516,232, filed on Jul. 18, 2019, now Pat. No. 10,531,883, said application No. 16/681,564 is a continuation of application No. 16/516,232, filed on Jul. 18, 2019, now Pat. No. 10,531,883.

(60) Provisional application No. 62/750,011, filed on Oct. 24, 2018, provisional application No. 62/701,086, filed on Jul. 20, 2018.

(51) Int. Cl.
*A61F 2/01* (2006.01)
*A61M 25/00* (2006.01)

(52) U.S. Cl.
CPC ............ *A61B 2017/00022* (2013.01); *A61B 2017/00154* (2013.01); *A61B 2017/22079* (2013.01); *A61B 2017/22082* (2013.01); *A61B 2217/007* (2013.01); *A61F 2/011* (2020.05)

(58) Field of Classification Search
CPC ..... A61B 2017/22082; A61B 2217/005; A61F 2/013; A61F 2002/011; A61M 1/0037; A61M 1/0066; A61M 1/0068; A61M 1/0072; A61M 1/0074; A61M 1/0003; A61M 1/0005; A61M 1/0007; A61M 1/0023; A61M 1/0031; A61M 1/0033; A61M 25/0075
See application file for complete search history.

(56) References Cited

U.S. PATENT DOCUMENTS

| | | |
|---|---|---|
| 4,458,877 A | 7/1984 | Holmes |
| 4,662,871 A | 5/1987 | Rafelson |
| 4,696,669 A | 9/1987 | Menhusen |
| 4,767,403 A | 8/1988 | Hodge |
| 4,902,276 A | 2/1990 | Zakko |
| 4,911,399 A | 3/1990 | Green |
| 5,254,085 A | 10/1993 | Cleveland, Jr. |
| 5,318,546 A | 6/1994 | Bierman |
| 5,496,267 A | 3/1996 | Drasler et al. |
| 5,704,584 A | 1/1998 | Winterer et al. |
| 6,027,490 A | 2/2000 | Radford et al. |
| 6,193,732 B1 | 2/2001 | Frantzen et al. |
| 6,200,276 B1 | 3/2001 | Biesel et al. |
| 6,226,843 B1 | 5/2001 | Crainich |
| 6,261,283 B1 | 7/2001 | Morgan et al. |
| 6,280,429 B1 | 8/2001 | Lewis et al. |
| 6,423,027 B1 | 7/2002 | Gonon |
| 6,423,028 B1 | 7/2002 | Gonon |
| 6,471,683 B2 | 10/2002 | Drasler et al. |
| 6,533,792 B2 | 3/2003 | Menne et al. |
| 6,605,074 B2 | 8/2003 | Zadno-Azizi et al. |
| 6,689,109 B2 | 2/2004 | Lynn |
| 6,887,220 B2 | 5/2005 | Hogendijk |
| 6,960,189 B2 | 11/2005 | Bates et al. |
| 7,004,931 B2 | 2/2006 | Hogendijk |
| 7,033,336 B2 | 4/2006 | Hogendijk |
| 7,178,699 B2 | 2/2007 | Spray et al. |
| 7,472,882 B2 | 1/2009 | Spray et al. |
| 7,530,976 B2 | 5/2009 | MacMahon et al. |
| 7,641,170 B2 | 1/2010 | Spray et al. |
| 7,713,276 B2 | 5/2010 | Dennis |
| 7,717,853 B2 | 5/2010 | Nita |
| 7,842,010 B2 | 11/2010 | Bonnette et al. |
| 7,846,126 B2 | 12/2010 | Steen et al. |
| 7,901,374 B2 | 3/2011 | Seto et al. |
| 7,918,822 B2 | 4/2011 | Kumar et al. |
| 7,931,659 B2 | 4/2011 | Bose et al. |
| 7,955,318 B1 | 6/2011 | Schultz et al. |
| 7,976,515 B2 | 7/2011 | Murphy et al. |
| 7,998,168 B2 | 8/2011 | Kleimann, Sr. |
| 8,206,374 B2 | 6/2012 | Duane et al. |
| 8,287,654 B2 | 10/2012 | Shaffer |
| 8,333,796 B2 | 12/2012 | Tompkins et al. |
| 8,337,452 B2 | 12/2012 | Seto et al. |
| 8,366,726 B2 | 2/2013 | Dennis |
| 8,366,735 B2 | 2/2013 | Bose et al. |
| 8,388,570 B2 | 3/2013 | Kumar et al. |
| 8,435,225 B2 | 5/2013 | Courtney et al. |
| 8,460,312 B2 | 6/2013 | Bose et al. |
| 8,465,439 B2 | 6/2013 | Parks |
| 8,465,507 B2 | 6/2013 | Cosgrove et al. |
| 8,518,017 B2 | 8/2013 | Caluori |
| 8,568,370 B2 | 10/2013 | Chew |
| 8,591,464 B2 | 11/2013 | Kumar et al. |
| 8,617,106 B2 | 12/2013 | Zacharias |
| 8,636,754 B2 | 1/2014 | Hughett, Sr. et al. |
| 8,647,294 B2 | 2/2014 | Bonnette et al. |
| 8,652,091 B2 | 2/2014 | Seto et al. |
| 8,690,907 B1 | 4/2014 | Janardhan et al. |
| 8,715,314 B1 | 5/2014 | Janardhan et al. |
| 8,721,595 B2 | 5/2014 | Stiehl et al. |
| 8,770,542 B2 | 7/2014 | Loth et al. |
| 8,814,778 B2 | 8/2014 | Kiser et al. |
| 8,814,821 B2 | 8/2014 | Steen et al. |
| 8,852,218 B2 | 10/2014 | Hughett, Sr. |
| 8,911,487 B2 | 12/2014 | Bennett et al. |
| 8,932,321 B1 | 1/2015 | Janardhan et al. |
| 9,017,349 B2 | 4/2015 | Privitera et al. |
| 9,073,069 B2 | 7/2015 | Seto et al. |
| 9,095,326 B2 | 8/2015 | Ritchie et al. |
| 9,119,656 B2 | 9/2015 | Bose et al. |
| 9,186,151 B2 | 11/2015 | Tompkins et al. |
| 9,220,485 B2 | 12/2015 | Parks |
| 9,248,228 B2 | 2/2016 | Bono et al. |
| 9,254,144 B2 | 2/2016 | Nguyen et al. |
| 9,370,611 B2 | 6/2016 | Ross et al. |
| 9,402,757 B2 | 8/2016 | Kassab et al. |
| 9,402,985 B2 | 8/2016 | Caluori |
| 9,492,598 B2 | 11/2016 | Nour |
| 9,510,854 B2 | 12/2016 | Mallaby |
| 9,526,864 B2 | 12/2016 | Quick |
| 9,526,865 B2 | 12/2016 | Quick |
| 9,545,334 B2 | 1/2017 | Steen et al. |
| 9,549,850 B2 | 1/2017 | Sorensen et al. |
| 9,554,805 B2 | 1/2017 | Tompkins et al. |
| 9,561,129 B2 | 2/2017 | Ross et al. |
| 9,572,933 B2 | 2/2017 | Grannell et al. |
| 9,597,108 B2 | 3/2017 | Ahn |
| 9,615,832 B2 | 4/2017 | Bose et al. |
| 9,615,951 B2 | 4/2017 | Bennett |
| 9,623,230 B2 | 4/2017 | Kim et al. |
| 9,655,633 B2 | 5/2017 | Leynov et al. |
| 9,681,882 B2 | 6/2017 | Garrison et al. |
| 9,737,309 B1 | 8/2017 | Ad |
| 9,775,621 B2 | 10/2017 | Tompkins et al. |
| 9,820,761 B2 | 11/2017 | Garrison et al. |
| 9,883,863 B2 | 2/2018 | Hughett, Sr. et al. |
| 9,883,885 B2 | 2/2018 | Henderick et al. |
| 9,889,289 B2 | 2/2018 | Howlett et al. |
| 9,901,351 B2 | 2/2018 | Winkler et al. |
| 9,901,352 B2 | 2/2018 | Fago et al. |
| 9,937,287 B2 | 4/2018 | Nour |
| 9,943,321 B2 | 4/2018 | Nita |
| 9,980,841 B2 | 5/2018 | Kassab et al. |
| 9,999,710 B2 | 6/2018 | Ross et al. |
| 10,166,024 B2 | 1/2019 | Williamson, IV et al. |
| 10,188,409 B2 | 1/2019 | Smalling |
| 10,219,940 B2 | 3/2019 | Raney et al. |
| 10,251,739 B2 | 4/2019 | Janardhan et al. |
| 10,258,354 B2 | 4/2019 | Turjman et al. |
| 10,299,947 B2 | 5/2019 | Bennett et al. |
| 10,314,953 B2 | 6/2019 | Ovchinnikov et al. |
| 10,335,260 B2 | 7/2019 | Janardhan et al. |
| 10,342,655 B2 | 7/2019 | Janardhan et al. |
| 10,390,926 B2 | 8/2019 | Janardhan et al. |
| 11,197,683 B1 * | 12/2021 | Teigen ............... A61M 1/774 |

(56) References Cited

U.S. PATENT DOCUMENTS

| | | |
|---|---|---|
| 2002/0058904 A1 | 5/2002 | Boock et al. |
| 2003/0023263 A1 | 1/2003 | Krolik et al. |
| 2003/0229368 A1 | 12/2003 | Viola |
| 2004/0024360 A1 | 2/2004 | Greter et al. |
| 2004/0102716 A1 | 5/2004 | Mobbs et al. |
| 2004/0267305 A1 | 12/2004 | Borgman |
| 2005/0149068 A1 | 7/2005 | Williams et al. |
| 2005/0182432 A1 | 8/2005 | Fanton et al. |
| 2005/0197640 A1 | 9/2005 | Say |
| 2005/0209585 A1 | 9/2005 | Nord et al. |
| 2005/0256447 A1 | 11/2005 | Richardson et al. |
| 2005/0273122 A1 | 12/2005 | Theroux et al. |
| 2006/0025794 A1 | 2/2006 | Fanton et al. |
| 2006/0058837 A1 | 3/2006 | Bose et al. |
| 2006/0200191 A1 | 9/2006 | Zadno-Azizi |
| 2006/0264995 A1 | 11/2006 | Fanton et al. |
| 2007/0060888 A1 | 3/2007 | Goff et al. |
| 2007/0100276 A1 | 5/2007 | Fanton et al. |
| 2007/0129652 A1 | 6/2007 | Nita |
| 2007/0161963 A1 | 7/2007 | Smalling |
| 2007/0239261 A1 | 10/2007 | Bose et al. |
| 2008/0015478 A1 | 1/2008 | Bose |
| 2008/0125695 A1 | 5/2008 | Hopkins et al. |
| 2008/0154184 A1 | 6/2008 | Blight et al. |
| 2008/0163731 A1 | 7/2008 | Lewis |
| 2008/0208324 A1 | 8/2008 | Glithero et al. |
| 2008/0319355 A1 | 12/2008 | Nita |
| 2009/0012545 A1 | 1/2009 | Williamson, IV et al. |
| 2009/0030400 A1 | 1/2009 | Bose et al. |
| 2009/0120957 A1 | 5/2009 | Phillips |
| 2009/0124962 A1 | 5/2009 | Hopkins et al. |
| 2009/0187198 A1 | 7/2009 | Weitzner |
| 2010/0076370 A1 | 3/2010 | Howlett et al. |
| 2010/0204672 A1 | 8/2010 | Lockhart |
| 2010/0217276 A1 | 8/2010 | Garrison et al. |
| 2011/0160621 A1 | 6/2011 | Nita |
| 2011/0160683 A1 | 6/2011 | Pinotti Barbosa et al. |
| 2011/0184454 A1 | 7/2011 | Barry et al. |
| 2011/0238147 A1 | 9/2011 | Bennett et al. |
| 2011/0313328 A1 | 12/2011 | Nita |
| 2011/0314977 A1 | 12/2011 | Lewis |
| 2011/0319927 A1 | 12/2011 | Nita |
| 2012/0078140 A1 | 3/2012 | Nita |
| 2012/0078285 A1 | 3/2012 | Griffin |
| 2012/0089080 A1 | 4/2012 | Ross et al. |
| 2012/0150147 A1 | 6/2012 | Leynov et al. |
| 2012/0171055 A1 | 7/2012 | Wisniewski |
| 2012/0289892 A1 | 11/2012 | Shtul et al. |
| 2012/0330196 A1 | 12/2012 | Nita |
| 2013/0110087 A1 | 5/2013 | Kane |
| 2013/0261730 A1 | 10/2013 | Bose et al. |
| 2013/0299032 A1 | 11/2013 | Caluori |
| 2014/0128907 A1 | 5/2014 | Hui et al. |
| 2014/0180377 A1 | 6/2014 | Bose et al. |
| 2014/0358175 A1 | 12/2014 | Tompkins et al. |
| 2015/0073524 A1 | 3/2015 | Bennett et al. |
| 2015/0157378 A1 | 6/2015 | Loebl et al. |
| 2015/0157772 A1 | 6/2015 | Li et al. |
| 2015/0173767 A1 | 6/2015 | Monti et al. |
| 2015/0196304 A1 | 7/2015 | Rabkin et al. |
| 2015/0223813 A1 | 8/2015 | Williamson, IV et al. |
| 2015/0342682 A1 | 12/2015 | Bowe |
| 2015/0359949 A1 | 12/2015 | Yeager et al. |
| 2015/0374380 A1 | 12/2015 | Miller et al. |
| 2016/0008001 A1 | 1/2016 | Winkler et al. |
| 2016/0058614 A1 | 3/2016 | Ross et al. |
| 2016/0095746 A1 | 4/2016 | Raney et al. |
| 2016/0095747 A1 | 4/2016 | Raney et al. |
| 2016/0095748 A1 | 4/2016 | Raney et al. |
| 2016/0095749 A1 | 4/2016 | Raney et al. |
| 2016/0095750 A1 | 4/2016 | Raney et al. |
| 2016/0166265 A1 | 6/2016 | Nita |
| 2016/0166266 A1 | 6/2016 | Nita |
| 2016/0220741 A1 | 8/2016 | Garrison et al. |
| 2016/0220807 A1 | 8/2016 | Bono et al. |
| 2016/0278895 A1 | 9/2016 | Caluori |
| 2017/0027730 A1 | 2/2017 | Kassab et al. |
| 2017/0049470 A1 | 2/2017 | Mallaby |
| 2017/0095259 A1 | 4/2017 | Tompkins et al. |
| 2017/0105743 A1 | 4/2017 | Vale et al. |
| 2017/0120039 A1 | 5/2017 | Childs et al. |
| 2017/0135700 A1 | 5/2017 | Rogowski et al. |
| 2017/0136209 A1 | 5/2017 | Burnett et al. |
| 2017/0143938 A1 | 5/2017 | Ogle et al. |
| 2017/0147765 A1 | 5/2017 | Mehta |
| 2017/0151032 A1 | 6/2017 | Loisel |
| 2017/0169374 A1 | 6/2017 | Harris et al. |
| 2017/0172581 A1 | 6/2017 | Bose et al. |
| 2017/0181760 A1 | 6/2017 | Look et al. |
| 2017/0215890 A1 | 8/2017 | Turjman et al. |
| 2017/0215902 A1 | 8/2017 | Leynov et al. |
| 2017/0238950 A1 | 8/2017 | Yang et al. |
| 2017/0238951 A1 | 8/2017 | Yang et al. |
| 2017/0238953 A1 | 8/2017 | Yang et al. |
| 2017/0239440 A1 | 8/2017 | Yang et al. |
| 2017/0239441 A1 | 8/2017 | Yang et al. |
| 2017/0239447 A1 | 8/2017 | Yang et al. |
| 2017/0252536 A1 | 9/2017 | Yang et al. |
| 2017/0266046 A1 | 9/2017 | Steen et al. |
| 2017/0296195 A1 | 10/2017 | Pleil et al. |
| 2017/0333170 A1 | 11/2017 | Caluori |
| 2017/0340797 A1 | 11/2017 | Raman et al. |
| 2017/0354777 A1 | 12/2017 | Ofek et al. |
| 2017/0360450 A1 | 12/2017 | Tompkins et al. |
| 2017/0367857 A1 | 12/2017 | Bennett et al. |
| 2018/0014840 A1 | 1/2018 | Panian |
| 2018/0042623 A1 | 2/2018 | Batiste |
| 2018/0064453 A1 | 3/2018 | Garrison et al. |
| 2018/0064578 A1 | 3/2018 | Clauson et al. |
| 2018/0116684 A1 | 5/2018 | Garrison et al. |
| 2018/0132857 A1 | 5/2018 | Fago et al. |
| 2018/0154063 A1 | 6/2018 | Criado et al. |
| 2018/0193042 A1 | 7/2018 | Wilson et al. |
| 2018/0197633 A1 | 7/2018 | Mehta |
| 2018/0199944 A1 | 7/2018 | Hughett, Sr. et al. |
| 2018/0221029 A1 | 8/2018 | Menn |
| 2018/0228502 A1 | 8/2018 | Shaffer et al. |
| 2018/0242989 A1 | 8/2018 | Nita |
| 2018/0263642 A1 | 9/2018 | Nita |
| 2018/0263646 A1 | 9/2018 | Loisel |
| 2018/0271686 A1 | 9/2018 | Kassab et al. |
| 2018/0317922 A1 | 11/2018 | Winkler et al. |
| 2018/0353194 A1 | 12/2018 | Shaffer et al. |
| 2018/0368965 A1 | 12/2018 | Janardhan et al. |
| 2019/0008626 A1 | 1/2019 | Janardhan et al. |
| 2019/0038300 A1 | 2/2019 | Savastano et al. |
| 2019/0133747 A1 | 5/2019 | Janardhan et al. |
| 2019/0142452 A1 | 5/2019 | Trosper et al. |
| 2019/0142568 A1 | 5/2019 | Janardhan et al. |
| 2019/0150959 A1 | 5/2019 | Cox et al. |
| 2019/0167406 A1 | 6/2019 | Janardhan et al. |
| 2019/0175184 A1 | 6/2019 | Hui et al. |
| 2019/0216476 A1 | 7/2019 | Barry et al. |
| 2019/0239910 A1 | 8/2019 | Brady et al. |

FOREIGN PATENT DOCUMENTS

| | | |
|---|---|---|
| WO | 94/21312 | 9/1994 |
| WO | 2010/089368 A2 | 8/2010 |
| WO | 2013184595 A1 | 12/2013 |
| WO | 2014151209 A1 | 9/2014 |
| WO | 2017147493 A1 | 8/2017 |
| WO | 2018019829 A1 | 2/2018 |
| WO | 2019115809 A1 | 6/2019 |
| WO | 2020023541 A1 | 1/2020 |

OTHER PUBLICATIONS

Health technology assessment of a national emergency endovascular service for mechanical thrombectomy in the management of acute ischaemic stroke, Health Information and Quality Authority, Jan. 25, 2017, pp. 1-197.

(56) References Cited

OTHER PUBLICATIONS

The Penumbra Pivotal Stroke Trial; Safety and Effectiveness of a New Generation of Mechanical Devices for Clot Removal in Intracranial Large Vessel Occlusive Disease, Stroke. 2009;40:2761-2768. Penumbra Inc. Alameda, Calif. DOI:10.1161/STROKEAHA. 108.544957.

Alawieh, Phd, et al., Lessons Learned Over More than 500 Stroke Thrombectomies Using ADAPT With Increasing Aspiration Cather Size, Neurosurgery vol. 0/No. 0/2018 pp. 1-10.

Almekhlafi, et al., Calcification and endothelialization of thrombi in acute stroke, Article in Annals of Neurology. vol. 64 No. 3 Sep. 2008. DOI:10.1002/ana.21404. Source: PubMed.

Arslanian, et al., Complete clot ingestion with cyclical ADAPT increases first-past recanalization and reduces distal embolization, J Neurointervent Surg 2019;0:1-6. doi:10.1136/neurintsurg-2018-014625.

Arslanian, et al.,"Is bigger really better for clot ingestion during a direct aspiration first pass tequenique?";, P-035; J NeuroIntervent Surg 2018;10(Suppl 2): pp. A43-A44.

Bhaskar, et al., Reperfusion therapy in acute ischaemic stroke: dawn of a new era?, BCN Neurology (2018) 18:8 DOI: 10.1186/s12883-017-1007-y; pp. 1-26.

Brinjikji, et al., Correlation of imaging and histopathology of thrombi in acute ischemic stroke with etiology and outcome: a systematic review, J NeuroIntervert Surg 2017;9:529-534 doi: 10.1136/neurintsurg-2016-012391.

Brouwer, et al., Clot Pathophysiology Why is it clinically important?, Neuroimag Clin N Am 28 (2018) 6111-623, https://doi.org/10.1016/j.nic2018.06.005; 1052-5149/18/2018 Elsevier Inc.

Chueh, et al., Abstract 3750: Embolus Adhesion to Activated Endthelium after embolization: A Parameter to predict outcomes of Mechanical thrombectomy in Acute Ischemic Stroke, Stroke: vol. 43, No. suppl_1, Feb. 2012.

Chueh, et al., Effectiveness of Mechanical Endovascular Thrombectomy in a Model system of Cerebrovascular Occlusion, AJNR Am J Neuroradiol 33:1998-2003 /Nov. 2012/ www.ajnr.org.

Chueh, et al., Mechanical Characterization of Thromboemboli in acute Ischemic Stroke and Laboratory Embolus Analogs, AJNR Am J Neuroradiol 32:1237-44/ Aug. 2011/ www.ajnr.org.

Cline, et al., Pathological Analysis of extracted clots in embolectomy patients with acute ischaemic stroke, O-027 J NeuroIntervent Surg 2013;5(Suppl 2):A15-A16, 10.1136/jnis-2013-010870.27.

De Meyer, et al., Analyses of thrombi in acute ischemic stroke: A consensus statement on current knowledge and future directions, International Journal of Stroke 2017, vol. 12(6) 606-614.

Delgado Almandoz, et al., Larger ACE 68 aspiration catheter increases first-pass efficacy of ADAPT technique, J NeuroIntervent Surg 2018;0:1-6. doi:10.1136/neurintsurg-2018-013957.

Duffy, et al.,"Novel methodology to replicate clot analogs with diverse composition in acute ischemic stroke";, J NeuroIntervent Surg 2017;9:486-491. doi:10.1136/neurintsurg-2016012308.

Duffy, et al., Per-Pass Analysis of Thrombus Composition in Patients with Acute Ischemic Stroke Undergoing Mechanical Thrombectomy, Stroke. 2019;50:1156-1163. DOI: 10.1161/STROKEAHA.118. 023419.

Fitzgerald, et al., Machine-learned Characterization of Acute Ischemic Stroke Clots Reveals a Correlation Between Clot Composition and HU Density on CT, Centre for Research in Medical Devices, National University of Irland, Galway. Department of Radiology, Mayo Cline, Rochester, MN, Division of Health Sciences, Mayo Clinic, Rochester, MN 2017 Mayo Foundation for Medical Education and Research, pp. 1.

Frei, et al.,"ADAPT FAST study: A direct aspiration first pass technique for acute stroke thrombectomy",, Article in Journal of Neurointerventional Surgery—Feb. 2014; Turk As, Frei D, Fiorella D, et al. J NeuroIntervent Surg 2014;6:260-264.

Froehler, et al.,"Comparison of Vacuum Pressures and Forces Generated by Different Catheters and Pumps for Aspiration Thrombectomy in acute Ischemic Stroke", Interventional Neurology 2017;6:199-206 DOI:10.1159/000475478 Published online: May 18, 2017; 2017 S. Karger AG,. Basel, www.karger.com/ine.

Ganesh, et al., Thrombectomy for Acute Ischemic Stroke: recent Insights and Future Directions, current Neurology and Neuroscience Reports (2018) 18:59 https://doi.org/10.1007/s11910-01869-8.

Gory, et al., A direct aspiration first pass technique for acute stroke therapy: a systematic review and meta-analysis, European Journal of Neurology 2018, 25: 284-292; doi:10.1111/ene.13490.

Gounis, Phd, et al., From Bench to Brain (and Back) Improving Mechanical Thrombectomy, New England Center for Stroke Research, WLNC 2017, Los Angles CA.

Gralla, et al., A Dedicated Animal Model for Mechanical Thrombectomy in Acute Stroke, AJNR Am J Neuroradiol 27:1357-61/ Jun.-Jul. 2006/ www.ajnr.org.

Gratz, et al., Whole-Brain Susceptibility-Weighted Thrombus Imaging in Stroke; Fragented Thrombi Predict Worse outcome, AJNR Am J Neuroradiol 2015 www.ajnr.org; pp. 1-6.

Heit, et al.,"Sofia intermediate catheter and the SNAKE technique: safety and efficacy of the Sofia catheter without guidewire of microcatheter construct", J NeuroIntervent Surg 2018;10:401-405. doi:10.1136/neurintsurg-2017-013256.

Hesse, et al., Comparing different thrombectormy techniques in five larg-volume centers: a real wordl observational study, J NeuroIntervent Surg 2018; 10:525-529. doi:10.1136/neurintsurg-2017-013394.

Hu, et al.,"Force and aspiration analysis of the ADAPT technique in acute ischemic stroke treatment", J NeuroIntervent Surg 2015; 0:1-3. doi:10.1136/neurintsurg-2014-011563.

Kaesmacher, et al., Risk of Thrombus Fragmentation during Endovascular Stroke Treatment, AJNR Am J Neuroradiol 38:991-98 May 2007 www.ajnr.org.

Kallmes, et al., Stroke Thromboembolism Registry of Imaging and Pathology (Strip), Strip Newsletter/ Edition #1/Confidential, Apr. 2018, pp. 1-5.

Kallmes, et al., The truth and fiction in aspiration physics: may the forces be with you, J NeuroIntervent Surg Nov. 2018 vol. 10 No. 11 pp. 1029-1030.

Kallmes, et al., To be or not2b? To see or not 2c? Alas, the clock is ticking on TICI, J NeuroIntervent Surg Apr. 2018 vol. 10 No. 4. pp. 323-324.

Kan, et al., A Novel Method of Thrombus Preparation for Use in a Swine Model for Evaluation of Thrombectomy Devices, AJNR Am J Neuroradiol 31:1741-43/ Oct. 2010/ www.ajnr.org, DOI 10.3174/ajnr.A1991.

Kurzawski, et al., Left atrial appendage function assessment and thrombus identification, Elsevier: IJC Heart & Vasculature, vol. 14, Mar. 2017, pp. 33-40.

Legrand MD, et al., Clot Burden Score on Admission T2*—MRI Predicts Recanalization in Acute Stroke, Stroke: Jul. 2013, pp. 1878-1884.

Liebeskind, et al., Collateral Circulation, Stroke. Sep. 2003;34:2279-2284.

Liebeskind, et al., CT and MRI Early Vessel Signs Reflect Clot Composition in Acute Stroke, Stroke. May 2011;42:1237-1243.; DOI: 10.1161/Strokeaha.110.605576.

Long, et al., Novel aspiration catheter design for acute stroke thrombectomy, J NeuroIntervent Surg 2018;0:1-6. doi:10.1136/neurintsurg-2017-013702.

Marder, et al., Analysis of Thrombi Retrieved from Cerebral Artiries of Patients with Acute Ischemic Stroke, Stroke. 2006;37:2086-2093. DOI: 10.1161/01.STR.0000230307.03438.94.

Merritt, et al., Quantifying the mechanical and histological properties of thrombus analog made from human blood for the creation of synthetic thrombus for therombectomy device testing, J NeuroIntervent Surg 2018;0:1-6. doi:10.1136/neurintsurg-2017-013675.

Moore, et al., 3D Models of blood flow in the cerebral vasculature, Article in Journal of Biomechanics Feb. 2006 DOI: 10.1016/j.jbiomech.2005.04.005—Source: PubMed: pp. 1-11.

Niesten, et al., Histopathologic Composition of Cerebral Thrombi of Acute Stroke Patients is Correlated withStroke Subtype and Thrombus Attenuation, Feb. 2014/ vol. 9/ Issue 2/ e88882; PLOS ONE 9(2):e88882. doi:10.1371/journal.pone.0088882.

(56) References Cited

OTHER PUBLICATIONS

Nikoubashman, et al., Necessary Catheter Diameters for Mechanical thrombectomy with ADAPT, AJNR AmJ Neuroradiol 38:2277-81, Dec. 2017, www.ajnr.org.
Nogueira, et al., The Trevo device: preclinical data of a novel stroke thrombectomy device in two different animal models of arterial thrombo-occlusive disease, J NeuroIntervent Surg 2012;4:295-300. doi:10.1136/neurintsurg-2011-010053.
Petty, et al., Ischemic Stroke Subtypes A Population-Based Study of Functional Outcome, Survival, and Recurrence, Stroke is available at http://www.strokeha.org, 2000, pp. 1062-1068.
Preut, et al., Novel Methodology for Emboli Analog Production and In-Vitro Simulation of Acute Ischemic Stroke, (2018), Theses and Dissertations.; 2802 http://scholarworks.uark.edu/etd/2802.
Price, et al., Bleeding outcomes after left atrial appendage closure compared with long-term warfarin: A pooled, pateient-level analysis of the watchmana randomized trial exprerience, Elsevier: JACC: Cardiovascular Interventions: vol. 8, Issue 15, Dec. 28, 2015, pp. 1925-1932.
Puetz, et al., Intracranial thrombus extent predicts clinical outcome, final infarct size and hemorrhagic transformation in ischemic stroke: the clot burden score, Journal compilation 2008 World stroke Organization International Journal of Stroke vol. 3, Nov. 2008, 230-236.
Rizvi, et al., Redefining 'success': a systematic review and meta-analysis comparing outcomes between incomplete and complete revascularization, J. NeuroIntervent Surg;0:1-5. doi:10.1136/neurintsurg-2018-013950.
Robbie, et al., Thrombi Formed in a Chandler Loop Mimic Human Arterial Trhombi in Structure and PAI-1 Content and Distribution, F.K. Schattauer Verlagsgesellschaft mbH (Struttgar) 77 (3) 510-5 (1997).
Romero, et al., Analysis and simulation of the adhesion forces between clot and the artery wall for a novel thrombectomy device applied to the Middle Cerebral Artery, ETSI Engineering, Universidad Politecnica de Madrid Spain pp. 1-6.
Saleh, et al., Safety and efficacy of the Aperio thrombectomy device when compared to the Solitaire AB/FR and the Revive devices in a pulsatile flow system, Am J Cardiovasc Dis 2012;2(4):301-308.
Samaniego, et al., Mechanical Thrombectomy: Emerging Technologies and Techniques, Journal of Stroke and Cerebrovascular Diseases, vol. No., (), 2018: pp. 1-17.
Schuhmann, et al., Immunohistochemical Analysis of Cerebral Thrombi Retrieved by Mechanical Thrombectomy from Patients with Acute Ischemic Stroke, Int. J. Mol. Sci. 2016, 17,298: doi:10.3390/ijms17030298.
Sillanpaa, et al.,"the clot burden score, the Boston Acute Stroke Imaging Scale, the cerebral blood volume ASPECTS, and two novel imaging parameters in the prediction of clinical outcome of ischemic stroke patients receiving intravenous thrombolytic therapy", Neuroradiology (2012) 54;663-672; DOI 10.1007/s00234-011-0954-z.
Simon, et al. , Exploring the efficacy of cyclic vs static aspiration in a cerebral thrombectomy model: an initial proof of concept study, J NeuraIntervent Surg 2014;6:677-683. doi:10.1136/neurintsurg-2013-010941.
Simon, et al., Hydrodynamic comparison of the Penumbra system and commonly available syringes in forced-suction thrombectomy, j NeuraIntervent surg 2014;6:205-211. doi:10.1136/neurintsurg-2012-010638.
Sorimachi, et al., Blood pressure measurement in the artery proximal and distal to an intra-arterial embolus during thrombolytic therapy, J NeuraIntervent Surg 2011;3:43-46. doi:10.1136/jmis.2010.003061.
Spiotta, et al., Hounsfield unit value and clot length in the acutely occluded vessel and time required to achieve thrombectomy, complications and outcome, J NeuraIntervent Surg 2014;6:423-427. Doi:10.1136/neurintsurg-203-010765.
Tan, et al., CT Angiography Clot Burden Score and Collateral Score: Correlation and Clinical and Radiologic Outcomes in Acute Middle Cerebral Artery infarct, AJNR Am J Neuroradiol 30:525-31/Mar. 2009/ www.ajnr.org; DOI 10.3174/ajnr.A1408.
Turk, et al., Initial clinical experience with the ADAPT technique: A direct aspiration first pass technique for stroke thrombectomy, J NeuraIntervent Surg 2013;0:1-7. doi:10.1136/neurintsurg-2013-010713.
Yuki, et al., The Impact of Thromboemboli Histology on the Performance of a mechanical thrombectomy Device, AJNR Am J Neuroradiol 33:643-48/Apr. 2012/ www.ajnr.org.
Zaidat, et al., First Pass Effect: A New Measure for Stroke Thrombectomy Devices, Stroke. 2018;49:660-666; originally published on line Feb. 19, 2018;; DOI: 10.1161/STROKEAHA.117.020315.
Zarrinkoob, et al., Blood flow distribution in cerebral arteries, Journal of Cerebral Blood Flow & Metabolism (2015) 35,648-654.
IPR2021-01466, Petition for Inter Partes Review of U.S. Pat. No. 10,531,883, dated Aug. 30, 2021, 87 pages.
IPR2022-00608, Petition for Inter Partes Review of U.S. Pat. No. 10,722,253, dated Feb. 15, 2022, 92 pages.
IPR2021-01466, Declaration of Brian Brown in Support of Petition for Inter Partes Review of U.S. Pat. No. 10,531,883, dated Aug. 26, 2021, 174 pages.
IPR2022-00608, Declaration of Brian Brown in Support of Petition for Inter Partes Review of U.S. Pat. No. 10,722,253, dated Feb. 2, 2022, 181 pages.
IPR2021-01466, Declaration of Ian Ross, MD in Support of Petition for Inter Partes Review of U.S. Pat. No. 10,531,883, dated Aug. 26, 2021, 35 pages.
IPR2022-00608, Declaration of Ian Ross, MD in Support of Petition for Inter Partes Review of U.S. Pat. No. 10,722,253, dated Feb. 2, 2022, 35 pages.
IPR2021-01466, Decision Granting Institution of *Inter Partes Review*, dated Mar. 14, 2022, 53 pages.
IPR2021-01466, Final Written Decision of U.S. Pat. No. 10,531,883, dated Mar. 10, 2023, 70 pages.
Judgment of Final Witten Decision received from Patent Trial and Appeal Board of U.S. Patent and Trademark Office for U.S. Pat. No. 10,722,253, entered on Sep. 6, 2023, 67 pages.
Decision of Denying Patent Owner's Request for Rehearing of Final Written Decision received from Patent Trial and Appeal Board of U.S. Patent and Trademark Office for U.S. Pat. No. 10,531,883, entered on Sep. 6, 2023, 16 pages.

\* cited by examiner

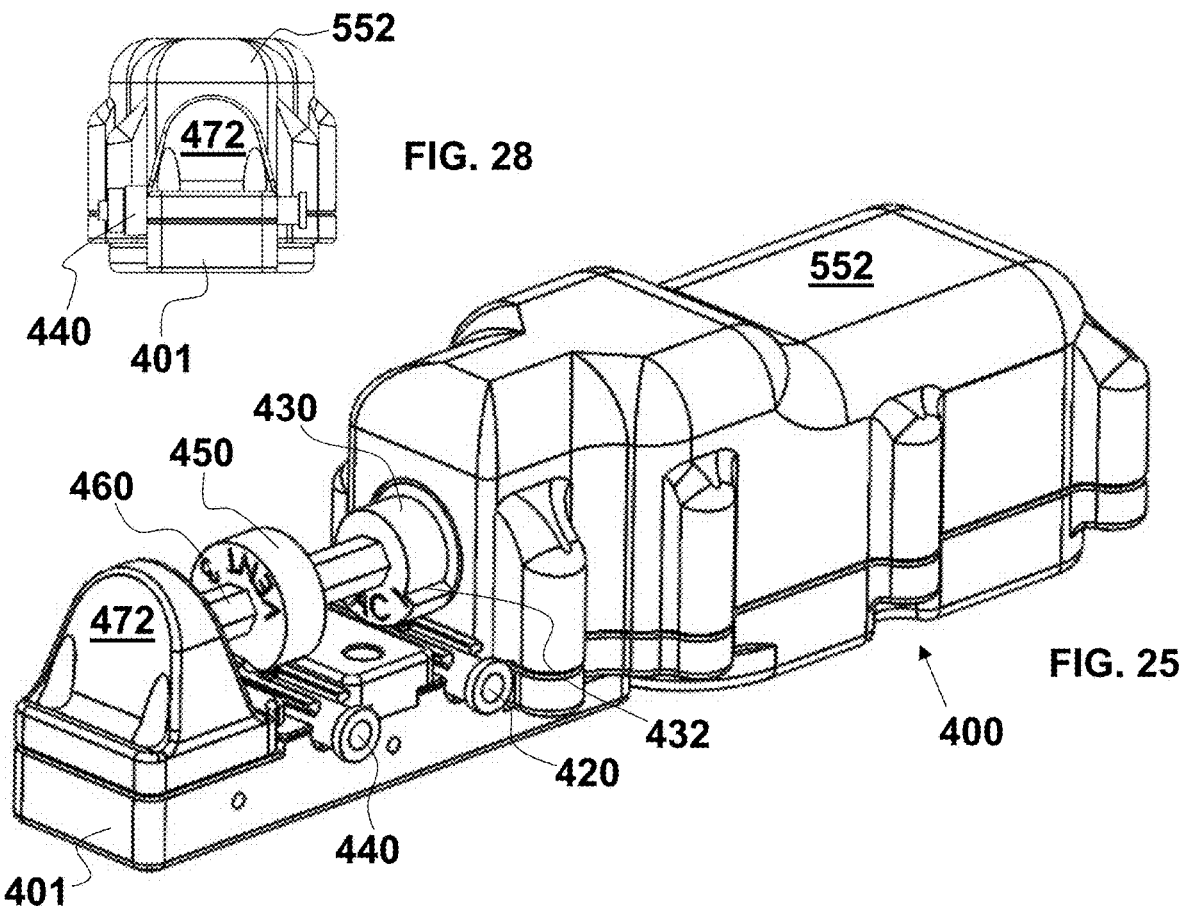
FIG. 28
FIG. 25
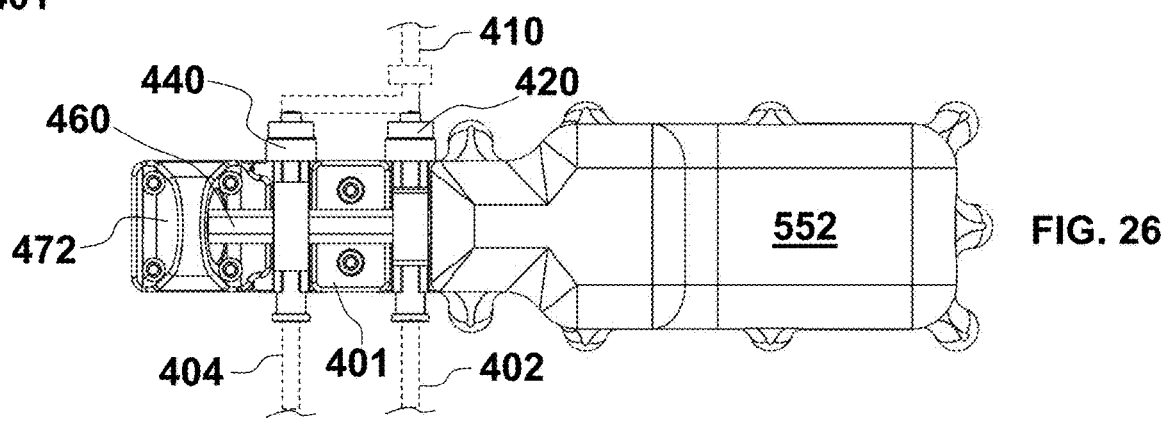
FIG. 26
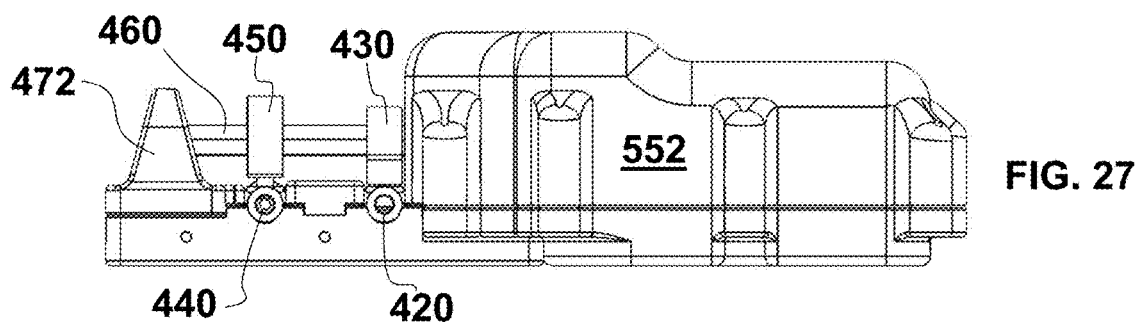
FIG. 27

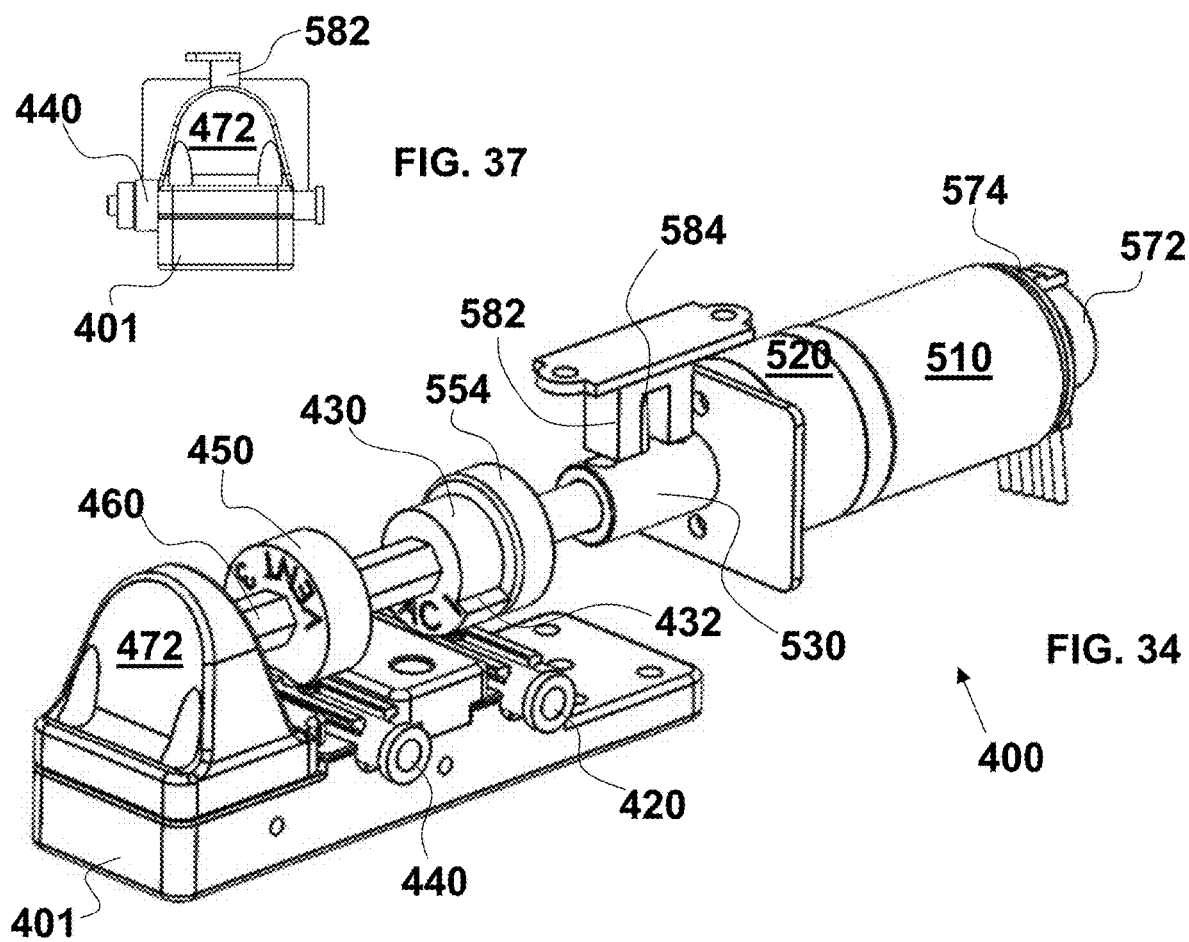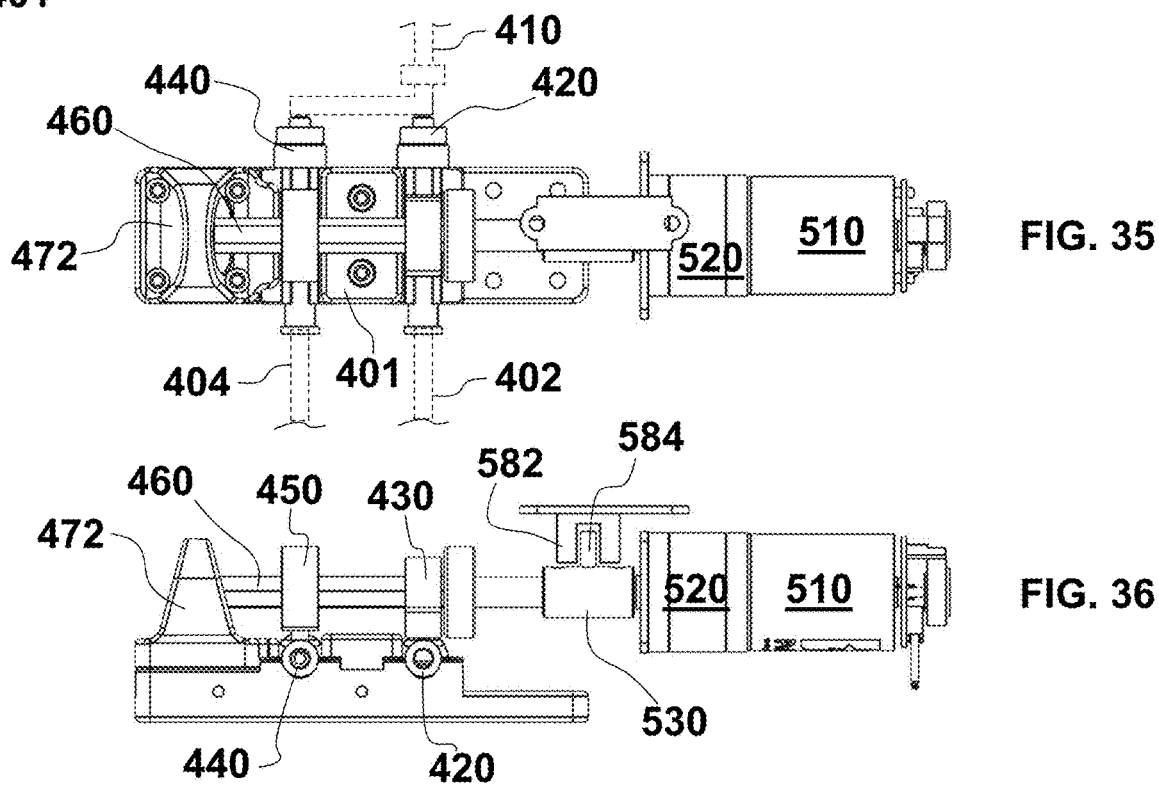

ASPIRATION THROMBECTOMY SYSTEM AND METHODS FOR THROMBUS REMOVAL WITH ASPIRATION CATHETER

CROSS-REFERENCE TO RELATED APPLICATIONS

This application is:
a continuation of U.S. patent application Ser. No. 16/681,564, filed on Nov. 12, 2019, which application is;
  a continuation of U.S. patent application Ser. No. 16/516,232, filed on Jul. 18, 2019, now U.S. Pat. No. 10,531,883, issued Jan. 14, 2020 (which application claims priority to U.S. Provisional Application Ser. Nos. 62/701,086, filed Jul. 20, 2018, and 62/750,011, filed Oct. 24, 2018); and
a continuing application, under 35 U.S.C. § 120, of international application No. PCT/US2019/042546, filed Jul. 19, 2019, which designated the United States, which international application claims the priority, under 35 U.S.C. § 119, of U.S. patent application Ser. No. 16/516,232, filed on Jul. 18, 2019 (which application claims priority to U.S. Provisional Application Ser. Nos. 62/701,086, filed Jul. 20, 2018, and 62/750,011, filed Oct. 24, 2018),
the entire disclosures of which are hereby incorporated herein by reference in their entireties.

STATEMENT REGARDING FEDERALLY SPONSORED RESEARCH OR DEVELOPMENT

Not Applicable

FIELD OF THE INVENTION

The present systems, apparatuses, and methods lie in the field of thrombus removal. The present disclosure relates to an aspiration thrombectomy system and methods for thrombus removal with aspiration catheter.

BACKGROUND OF THE INVENTION

Ischemic strokes are usually caused by a blood clot that blocks or plugs a blood vessel in the brain. This blockage prevents blood from flowing to the brain. Within minutes, brain cells begin to die, which, if not treated rapidly, causes brain damage or death. The costs associated with removing a clot are significant. Most treatments involve thrombectomy: the removal of the clot by aspiration, mechanical retrieval, or some combination thereof.

Removal by aspiration is effected by placing a source of vacuum, e.g., an aspiration or vacuum catheter, upstream of the clot and drawing the clot into or against the distal end of the catheter. Conceptually, aspiration is effective but some significant problems occur in practice. The basic configuration for an aspiration catheter includes a length of hollow catheter having a proximal end fluidically connected to a vacuum or suction pump. In this configuration, operation of the suction pump causes fluid and particulates at the distal end of the catheter to enter the distal opening of the hollow lumen and travel to the proximal end of the lumen near or into the suction pump. Conventional aspiration catheters are threaded through a balloon guide catheter. In one exemplary procedure, the balloon of the guide catheter is guided into the internal carotid artery of the brain. The balloon is inflated to occlude the vessel. The aspiration catheter is threaded through the balloon guide catheter and out the distal end of the guide catheter past the balloon. The distal end of the aspiration catheter is advanced to the clot that is occluding the brain vessel. Suction connected to the aspiration catheter is turned on to cause flow reversal. Ideally, this system aspirates the clot entirely out of the neurovasculature and to the proximal end of the aspiration catheter so that extraction and re-establishment of blood flow could be confirmed. In practice, however, this rarely occurs.

Thrombi are frequently of a larger diameter than the catheter being used to aspirate them. For aspiration to be successful, the thrombus must deform to conform to the inner diameter of the aspiration catheter. During conventional aspirations, it is common for applied vacuum to partially draw a thrombus into the distal opening of the aspiration catheter's lumen, thereby deforming some of the thrombus to the catheter's inner diameter. At this point, the thrombus becomes lodged completely within, partially within, or at the distal opening of the aspiration catheter, a condition that can be referred to as corked or corking. In effect, the distal end becomes a suction cup grasper for the clot. When this situation occurs, a surgeon's only option is to use the aspiration catheter as a fishing line to pull the clot back through the balloon guide and out of body. The other option is not viable, that is, reversing the suction to pressurize the clot and eject it forcibly and uncontrollably out of the distal opening of the aspiration catheter. Such action is dangerous to the patient for many reasons, the primary one being that forcibly and uncontrollably ejecting the clot may cause the clot to move further distally within the vessel in which it was originally lodged. That distal movement would not only cause the clot to be further within the vessel—i.e., in an even smaller diameter of the vessel than when it was originally lodged—but it could permanently lodge the clot into that vessel, making it impossible to remove, or it could burst the vessel. Those of skill in the art know that these situations are to be avoided because of the serious potential risks to the patient.

Even when the surgeon uses the aspiration catheter to fish out the clot, there is no assurance that the entirety of the clot will be removed. Pieces of the clot can break off during movement, when that occurs, the pieces re-embolize within the same vessel or within different vessels that might be even more difficult to remove.

When all or most of the clot is drawn out from the patient, it is difficult to confirm that the entire thrombus was removed. A significant disadvantage of current thrombus removal devices is the inability of a surgeon to ascertain thrombus capture/removal without the full withdrawal of a given therapeutic device from a patient's anatomy. Even systems capable of fully aspirating a given thrombus are problematic, because the reservoirs into which aspirated contents are deposited are located outside of the sterile field in an operating room setting. This location, outside the sterile field, makes it difficult or impossible for physicians operating aspiration catheters to easily visualize and appraise aspirated thrombus material.

To confirm thrombus removal can require the surgeon to attempt aspiration again. The aspiration and balloon guide catheters have to be cleaned out, access to distal anatomy has to be re-established, and, when the aspiration catheter finally is located back at the embolism site, the same issues may be present again with whatever embolus material remains. A disadvantage of these procedures is the significant increase in procedure time, which not only significantly increases the cost (as each minute in an operating room is expensive), it also increases the surgeon's stress, which decreases the success rate of the operation.

First-pass recanalization rate is a metric used to determine the efficacy of thrombectomy systems. Most current systems offer rates of between 30% and 60%. A system that increases the first-pass recanalization rate is valuable and desirable.

Even with an attempt to maintain vacuum pressure utilizing manual periodic cycling, prior art systems are not capable of avoiding positive pressures at the distal end of the catheter. Prior art systems are not able to react quickly enough to keep the distal end of the catheter from experiencing a positive pressure. When positive pressure exists at the distal end of the lumen, liquid from inside the lumen exits out from the distal end of the catheter in a distal direction. This is referred to as forward flow. The prior art do not have a fast enough reaction time to quell forward flow. Forward flow, therefore, can and does remove thrombi off of the distal end and risk sending thrombi further distally in the vasculature. Such systems cannot guarantee removing all forward flow eliminating positive pressure at the distal end of the catheter.

Thus, a need exists to overcome the problems with the prior art systems, designs, and processes as discussed above.

SUMMARY OF THE INVENTION

The systems, apparatuses, and methods described provide an aspiration thrombectomy system and methods for thrombus removal with an aspiration thrombectomy system that overcome the hereinafore-mentioned disadvantages of the heretofore-known devices and methods of this general type and that provide such features with increased first-pass recanalization rate by completely pulling the embolus out and, thereby, reducing the instance of aspiration catheter obstruction/clogging by the embolus.

The systems, apparatuses, and methods provide an aspiration thrombectomy system that completely vacuums up the clot so that clots are no longer dragged out of vasculature while half hanging out of a catheter tip. The aspiration thrombectomy system moves the vacuumed clot all the way to the proximal end of the vacuum channel and allows the surgeon to confirm recanalization of the vessel in which the clot formerly resided (for example, by injecting contrast through the catheter that remains in place after clot removal) and provides structure to indicate to the surgeon that the thrombus has been removed and that flow has been restored.

The systems, apparatuses, and methods provide an aspiration thrombectomy system that can be coupled with conventional aspiration catheters to significantly increase the efficacy of such catheter and pump systems. Vacuum level is indicated herein in two different ways:
1) as the absolute level of pressure, where a "high vacuum" approaches zero absolute pressure. This is the "absolute pressure" way of measuring vacuum. A perfect vacuum would be zero, and atmospheric pressure would be indicated by measuring the height of a column of mercury that can be supported by a standard atmosphere (760 mm Hg). Hence, lower values indicate an increased level of vacuum relative to the ambient atmospheric pressure.
2) The pressure relative to atmospheric pressure may be indicated. This way of measuring pressure relative to a standard atmospheric pressure is known as "gage pressure." The most common way of measuring pressure in the vacuum realm (below atmospheric pressure) is by using a gage calibrated so that one atmosphere reads zero (standard atmospheric pressure), and the highest possible level of vacuum would be indicated as "29.92 inches of mercury" Common mechanical vacuum gauges work this way, so this usage has become common.

Herein, the "gage pressure" is used as method of indicating vacuum level; i.e., "zero inches of mercury" means atmospheric pressure, no suction at all. A high number (e.g., 25" Hg) means a high level of vacuum suction. (The highest possible level of vacuum measured this way would be 29.92" Hg.) "Vacuum" as used herein is a condition below normal atmospheric pressure. In the instant application, the units of pressure for vacuum is pounds per square inch ("PSI").psi"), inches of mercury, or mmHg. Depending on the context of use of the word vacuum, a "high" vacuum is referred to herein as a low pressure that is lower than atmospheric pressure. Vacuum also refers to a negative pressure(s) and a pressure above atmospheric pressure is referred to as a positive pressure. In some instances, however, use of the word "high" with respect to pressure can mean a greater negative or can mean a greater positive based on the context. Likewise, use of the words "low" or "lower" with respect to pressure can mean a lesser negative or can mean a lesser positive based on the context Thrombi are frequently of a larger diameter than the catheter being used to aspirate them. In order for aspiration to be successful, the thrombus must deform to conform to the inner diameter of the aspiration catheter. During conventional aspirations, it is common for applied vacuum to partially draw a thrombus into the distal opening of the aspiration catheter's lumen. At this point, the thrombus becomes stuck with some of the thrombus resting within the catheter's inner diameter and some of the thrombus protruding from the distal end.

The systems, apparatuses, and methods provide an aspiration thrombectomy system with an unclogging structure and technique that temporarily halts vacuum at the distal end of the aspiration catheter, pushes the thrombus distally out of the lumen, and then re-applies vacuum—an occlusion-vacuum-pressure sequence of operation. Upon re-application of the vacuum, the thrombus accelerates back into the catheter and deforms to a diameter allowing it to be completely aspirated. Each halting of the vacuum, thrombus pushing, and reapplication of the vacuum is controlled by the surgeon.

The systems and methods operate an aspiration/suction catheter with a mechanism to stop the vacuum and then press the distal fluid column in reverse, i.e., a positive displacement without a check valve, referred to herein as a column shift. All functions can be controlled with a single handle, including vacuum shut off and column shift while limiting the amount and the force for the column shift. When the controller is actuated, a positive amount of exit flow is created without possibility of overshooting. The exiting movement of fluid is limited to a specific volume and/or pressure and is automatically and precisely controlled. It is the user who controls when the column shift occurs and when it returns. A trap is disposed at an exit to catch and display the thrombus. A vent can be opened to atmosphere to clear fluid in the trap and show what thrombus remains.

With the foregoing and other objects in view, there is provided, a vacuum catheter for removing an object from within a human vessel comprising a vacuum tube defining an interior vacuum channel comprising a proximal opening for receiving application of vacuum and a distal capture opening fluidically connected to the proximal opening, the distal capture opening configured to receive therein the object responsive to application of the vacuum, and comprising an intermediate section between the proximal opening and the distal capture opening, and a vacuum interruption controller comprising a body through which a portion of the intermediate section passes and an extrusion compressor movably disposed with respect to the body towards and away from the portion of the intermediate section such that, in a rest state, the extrusion compressor does not occlude the vacuum channel and, in an actuated state, the extrusion compressor first occludes the vacuum channel and then moves fluid disposed between the portion of the intermediate section and the distal capture opening a given distance distally towards the distal capture opening.

In accordance with another feature, there is provided a vacuum pump selectively applying vacuum to the proximal opening.

In accordance with a further feature, the vacuum tube has a proximal portion and which further comprises a catheter body surrounding the vacuum tube and configured to steer at least the proximal portion of the vacuum tube.

In accordance with an added feature, the vacuum tube has a proximal portion sized to fit within the Circle of Willis in a brain and the object is a blood clot adjacent the Circle of Willis.

With the foregoing and other objects in view, there is provided, a clot removal system comprising a catheter having a distal end and defining a lumen filled with a liquid column having a proximal portion and a distal portion, a controllable vacuum valve, a vacuum source fluidically connected to the vacuum valve, a controllable vent valve having a vent liquid input, a vent fluid source containing a vent liquid and fluidically connected to the vent valve to retain the vent liquid at the vent fluid input, a manifold connected to the catheter, to the vacuum valve, and to the vent valve, the manifold fluidically connecting the proximal portion of the liquid column in the lumen to the vacuum source through the vacuum valve and to the vent fluid source through the vent valve, a controller connected to the vacuum valve and the vent valve and configured to selectively open and close the vacuum valve and the vent valve such that, responsive to opening the vacuum valve, the vacuum source is fluidically connected to the liquid column in the lumen and, responsive to opening the vent valve, the vent fluid source is fluidically connected to the liquid column in the lumen, the controller configured to cyclically open and close the vacuum valve and the vent valve to change a level of vacuum at the distal end and prevent forward flow of the distal portion out from the distal end during each cycle.

With the objects in view, there is also provided a clot removal system comprising a catheter having a distal end and defining a lumen filled with a liquid column having a proximal portion and a distal portion, a controllable vacuum valve, a vacuum source fluidically connected to the vacuum valve, a controllable vent valve having a vent liquid input, a vent fluid source containing a vent liquid and fluidically connected to the vent valve to retain the vent liquid at the vent fluid input, a manifold connected to the catheter, to the vacuum valve, and to the vent valve, the manifold fluidically connecting the proximal portion of the liquid column in the lumen to the vacuum source through the vacuum valve and to the vent fluid source through the vent valve, a controller connected to the vacuum valve and the vent valve and configured to selectively open and close the vacuum valve and the vent valve such that responsive to opening the vacuum valve, the vacuum source is fluidically connected to the liquid column in the lumen and responsive to opening the vent valve, the vent fluid source is fluidically connected to the liquid column in the lumen, the controller configured to cyclically open and close the vacuum valve and the vent valve in a repeated cycle comprising a double-closed state in which the vacuum valve is closed and the vent valve is closed to change a level of vacuum at the distal end and prevent forward flow of the distal portion out from the distal end during each cycle, and a time of the double-closed state is no greater than approximately 30 ms.

With the objects in view, there is also provided a clot removal system comprising a catheter having a distal end and defining a lumen filled with a liquid column having a proximal portion and a distal portion, a vacuum source, a vent liquid source, and a vacuum and vent control system configured to cyclically connect or disconnect the vacuum source and the vent liquid source to change a level of vacuum at the distal end and substantially prevent forward flow.

With the objects in view, there is also provided a clot removal system comprising a catheter having a distal end and defining a lumen filled with a liquid column having a proximal portion and a distal portion, a vacuum source, a vent liquid source, and a vacuum and vent control system configured to cyclically fluidically connect to the proximal portion at least one of vacuum from the vacuum source, vent liquid from the vent liquid source, and neither the vacuum nor the vent liquid, and thereby change a level of vacuum at the distal end and substantially prevent forward flow.

In accordance with another feature, the controller is configured to cyclically open and close the vacuum valve and the vent valve in a repeated cycle comprising a double-closed state in which the vacuum valve is closed and the vent valve is closed.

In accordance with a further feature, a time of the double-closed state is no greater than 30 ms.

In accordance with an added feature, the controller is configured to cyclically open and close the vacuum valve and the vent valve in a repeated cycle comprising a vent-only state in which the vacuum valve is closed and the vent valve is open.

In accordance with an additional feature, a time of the vent-only state is no greater than 50 ms.

In accordance with yet another feature, the controller is configured to selectively open and close the vacuum valve and the vent valve cycle in a repeated cycle comprising a vacuum-only state in which the vacuum valve is open and the vent valve is closed, a first double-closed state in which the vacuum valve is closed and the vent valve is closed, a vent-only state in which the vacuum valve is closed and the vent valve is open, and a second double-closed state in which the vacuum valve is closed and the vent valve is closed.

In accordance with yet a further feature, a time between an opening of the vent valve and a closing of the vent valve is between approximately 10 ms and approximately 50 ms.

In accordance with yet an added feature, a period of the cycle is between approximately 6 Hz and approximately 16 Hz.

In accordance with yet an additional feature, a period of the cycle is between approximately 8 Hz and 12 Hz.

In accordance with again another feature, the change in the level of vacuum at the distal end is greater than approximately 15 inHg in no greater than approximately 50 ms.

In accordance with again another feature, the change in the level of vacuum at the distal end is greater than approximately 20 inHg and no greater than approximately 30 ms; and In accordance with again another feature, the change in the level of vacuum at the distal end is greater than approximately 25 inHg and no greater than approximately 20 ms.

In accordance with again an added feature, the lumen has an internal diameter of between approximately 0.038" and approximately 0.106" and the controller is configured to cyclically open and close the vacuum valve and the vent valve at a frequency of between 2 and 16 Hz.

In accordance with again an additional feature, the lumen has an internal diameter of between approximately 0.068" and approximately 0.088" and the controller is configured to cyclically open and close the vacuum valve and the vent valve at a frequency of between 2 and 16 Hz.

In accordance with still another feature, the controller is configured to cyclically open and close the vacuum valve and the vent valve in a repeated cycle and prevent forward flow of the distal portion out from the distal end during each cycle by regulating timing of the vent valve.

In accordance with still a further feature, the controller is configured to cyclically open and close the vacuum valve and the vent valve to retain a level of pressure at the distal end at less than physiological pressure.

In accordance with a concomitant feature, there is provided a shaft and the vacuum valve and the vent valve are mounted together on the shaft.

Operation of a ROAR process as described hereinbelow successfully removes thrombi for two reasons. First, the ROAR effect overcomes the static friction of a clot that is fixed or "stuck" on the catheter tip while under constant suction. The ROAR process provides an oscillating/alternating displacement that causes the clot to "shuttle" back and forth to overcome static frictional force. Second, there is a morcellation of the clot that overcomes different clot morphologies as well as overriding volume and diameter constraints of the small, fixed luminal volume dictated by the micro-anatomic environment.

The systems and methods described and shown herein react quickly enough to keep pressure at the distal end from going positive. By cycling the vacuum and vent valves at a sufficiently fast rate, a pressure measurement at a rate of one thousand samples per section at the distal end of the catheter lumen proves that the distal end of the ROAR catheter does not experience positive pressure and substantially quells forward flow. The timing between operating the vacuum and vent valves can be adjusted so that physical mechanisms that would cause distal end positive pressure can be avoided in both the open flow condition and in the corked condition.

In accordance with an exemplary embodiment, the distal portion of the liquid column exiting the distal end is limited to no more than approximately 2 microliters.

In accordance with an exemplary embodiment, a clot removal system comprises a catheter having a distal end and defining a lumen filled with a liquid column having a proximal portion and a distal portion, a vacuum source, a vent fluid source containing a vent liquid, and a vacuum and vent control system configured to cyclically fluidically connect to and disconnect from the proximal portion at least one of vacuum from the vacuum source and vent fluid from the vent fluid source, and thereby change a level of vacuum at the distal end and substantially prevent the distal portion of the liquid column from exiting the distal end.

In accordance with an exemplary embodiment, a clot removal system comprises a catheter having a distal end and defining a lumen filled with a liquid column having a proximal portion and a vacuum and vent control system configured to cyclically connect to and disconnect from the proximal portion vacuum and vent fluid to create therein a forward flow pressure pulse and thereby reverse flow in the liquid column and substantially prevent the forward flow pressure pulse from reaching the distal end.

In accordance with an exemplary embodiment, a clot removal system comprises a catheter having a distal end and defining a lumen filled with a liquid column having a proximal portion and a vacuum and vent control system configured to cyclically connect to and disconnect from the proximal portion vacuum and vent fluid to create therein a forward flow pressure pulse and, before the forward flow pressure pulse reaches the distal end, reverse flow in the liquid column and thereby substantially prevent the forward flow pressure pulse from reaching the distal end.

In accordance with an exemplary embodiment, a clot removal system comprises a catheter having a distal end and defining a lumen filled with a liquid column having a proximal portion and a vacuum and vent control system configured to cyclically connect to and disconnect from the proximal portion vacuum and vent fluid and thereby allow the liquid column to move and stop to create therein a forward flow pressure pulse and, before the forward flow pressure pulse reaches the distal end, alternate control to reverse flow in the liquid column and thereby control the forward flow pressure pulse by substantially preventing the forward flow pressure pulse from reaching the distal end.

In accordance with an exemplary embodiment, the controller is configured to change the level of vacuum at the distal end in a cycle while simultaneously preventing distal movement of the distal portion of the liquid column.

In accordance with an exemplary embodiment, the controller is configured to selectively open and close the vacuum valve and the vent valve cycle in a repeated cycle comprising a first state in which the vacuum valve is open and the vent valve is closed, a second state in which the vacuum valve is closed and the vent valve is closed, a third state in which the vacuum valve is closed and the vent valve is open, and a fourth state in which the vacuum valve is closed and the vent valve is closed.

In accordance with an exemplary embodiment, a clot removal system comprises a catheter defining a lumen filled with a liquid column from a proximal portion to a distal end and a water hammer controller configured to alternatively connect vacuum and/or fluid at atmospheric or body or lower pressure to the lumen, thereby allowing the liquid column to move and stop to create therein a water hammer and, before the water hammer reaches the distal end, alternate control to reverse flow and thereby control the water hammer by substantially preventing the water hammer from reaching the distal end.

In accordance with an exemplary embodiment, a clot removal system comprises a catheter with a lumen, a vacuum source, a controllable vacuum valve, a vent fluid source, a controllable vent valve, a manifold connected to the catheter, to the vacuum valve, and to the vent valve, and a controller controlling the vacuum valve and the vent valve.

In accordance with an exemplary embodiment, the controller is configured to modulate the vacuum valve and the vent valve in a cycle that, responsive to vacuum being applied to the catheter, the compliance of the catheter causes a reduction in volume such that, when the vacuum is closed and the vent is open, the compliance acts as a spring and the lumen ingests vent fluid in a distal direction and, before a momentum induced by the ingested fluid reaches the distal end of the catheter, the controller modulates the valves to reverse a direction and quell movement of the fluid of the fluid and prevent the fluid from exiting the distal end of the catheter.

In accordance with an exemplary embodiment, a clot removal system comprises a catheter having a lumen, a substantially incompressible connection tube having interior lumen with a proximal end and a distal end fluidically connected to the lumen, a vacuum source, and a vacuum/vent manifold comprising a manifold chamber having an output fluidically connected to the proximal end, a vacuum line fluidically connected to the manifold and to the vacuum source to present vacuum from the source to the manifold chamber, and a vent line fluidically connected to the manifold and to a fluid bath at atmospheric pressure.

In accordance with an exemplary embodiment, the clot removal system comprises a fixed cycle with plurality of pinch valves and plurality of cams mechanically coupled to the valves so that orientations of the cams cannot be changed.

In accordance with an exemplary embodiment, the time within which the forward flow pulse is quelled is no greater than approximately 20 ms.

In accordance with an exemplary embodiment, a clot removal system comprises a pulsatile vacuum controller configured to alternatively connect vacuum and/or fluid at atmospheric/body/slightly lower than body/slightly higher than body pressure to the lumen and thereby allow the liquid column to move and stop to create therein a forward flow pressure pulse and (before the forward flow pressure pulse reaches the distal end, alternating control to reverse flow and thereby) control the forward flow pressure pulse by substantially preventing the forward flow pressure pulse from reaching the distal end.

With the foregoing and other objects in view, there is provided, a clot removal system comprising a catheter having a proximal end and a distal end and defining a lumen configured to be filled with a liquid column having a proximal portion, a vacuum pump configured to supply vacuum, a vent container holding a vent liquid, a vent valve configured to fluidically communicate with the vent liquid in the vent container and with the proximal portion of the liquid column at the proximal end of the catheter, a vacuum valve configured to fluidically communicate with the vacuum from the vacuum pump and with the proximal portion of the liquid column at the proximal end of the catheter, and a controller configured to carry out a pre-determined pattern of opening and closing the vent and vacuum valves to change a level of vacuum at the distal end and, while changing the level of vacuum at the distal end, to substantially prevent forward flow of the liquid at a distal end of the liquid column.

With the objects in view, there is also provided a clot removal system comprising a catheter having a proximal end and a distal end and defining a lumen configured to be filled with a liquid column having a proximal portion, a vacuum pump configured to supply vacuum, a vent liquid container holding a vent liquid, a vent valve configured to fluidically communicate with the vent liquid in the liquid container and with the proximal portion of the liquid column at the proximal end of the catheter, a vacuum valve configured to fluidically communicate with the vacuum from the vacuum pump, and with the proximal portion of the liquid column at the proximal end of the catheter, and a controller configured to carry out a pre-determined cycle of opening and closing the vent and vacuum valves to change a level of vacuum at the distal end and, during each cycle, to substantially prevent forward flow of liquid at the distal end of the liquid column.

In accordance with another feature, the liquid at the distal end of the liquid column is one or more of albumin, d5W water, normal saline, half-normal saline, lactated Ringer's solution, and blood, and mixtures thereof.

In accordance with a further feature, there is provided a manifold comprising the vent valve, the vacuum valve, and an output and an extension line fluidically connecting the proximal end of the catheter to the output of the manifold.

In accordance with an added feature, a portion of the pre-determined pattern includes a time period where both the vent and vacuum valves are closed.

In accordance with an additional feature, the controller is configured to open and close the vent and vacuum valves in a repeated cycle comprising a double-closed state in which both the vent and vacuum valves are closed.

In accordance with yet another feature, a time of the double-closed state is no greater than 30 ms.

In accordance with yet a further feature, the controller is configured to open and close the vent and vacuum valves in a repeated cycle comprising a vent-only state in which the vacuum valve is closed and the vent valve is open, and a time of the vent-only state is no greater than 50 ms.

In accordance with yet an added feature, the controller is configured to repeatedly and periodically carry out the pre-determined pattern.

In accordance with yet an additional feature, the controller is configured to selectively open and close the vent and vacuum valves in a repeated cycle comprising a vacuum-only state in which the vacuum valve is open and the vent valve is closed, a first double-closed state in which the vacuum valve is closed and the vent valve is closed, a vent-only state in which the vacuum valve is closed and the vent valve is open, and a second double-closed state in which the vacuum valve is closed and the vent valve is closed.

In accordance with again another feature, the controller is configured to selectively open and close the vent and vacuum valves in a repeated cycle comprising a vacuum-only state in which the vacuum valve is open and the vent valve is closed, followed by a first double-closed state in which the vacuum valve is closed and the vent valve is closed and a time of the first double-closed state is no greater than 30 ms, followed by a vent-only state in which the vacuum valve is closed and the vent valve is open, followed by a second double-closed state in which the vacuum valve is closed and the vent valve is closed.

In accordance with again a further feature, a time between an opening of the vent valve and a closing of the vent valve is between approximately 10 ms and approximately 50 ms.

In accordance with again an added feature, a frequency of the cycle is between approximately 6 Hz and approximately 16 Hz.

In accordance with still another feature, a frequency of the cycle is between approximately 8 Hz and 12 Hz.

In accordance with still a further feature, the change in the level of vacuum at the distal end is one of greater than approximately 15 inHg and occurs in no greater than approximately 50 ms, greater than approximately 20 inHg and occurs in no greater than approximately 30 ms, and greater than approximately 25 inHg and occurs in no greater than approximately 20 ms.

In accordance with still an added feature, the lumen has a diameter of between approximately 0.038" and approximately 0.106" and the controller is configured to repeatedly and periodically carry out the pre-determined pattern of opening and closing the vent and vacuum valves at a frequency of between 2 and 16 Hz.

In accordance with still an additional feature, the lumen has an internal diameter of between approximately 0.068" and approximately 0.088" and the controller is configured to repeatedly and periodically carry out the pre-determined pattern of opening and closing the vent and vacuum valves at a frequency of between 6 and 12 Hz.

In accordance with another feature, the controller is configured to open and close the vent and vacuum valves in a repeated cycle of the pre-determined pattern and prevent forward flow of the distal portion out from the distal end during each cycle by regulating timing of the vent valve.

In accordance with a further feature, the controller is configured to open and close the vacuum valve and the vent valve in a repeated cycle of the pre-determined pattern to retain a level of pressure at the distal end at less than physiological pressure.

In accordance with an added feature, the controller is one of a mechanical valve controller and an electronic valve controller.

In accordance with a concomitant feature, there is provided a shaft and the vent and vacuum valves are cam-driven valves with respective cams mounted together on the shaft.

With the foregoing and other objects in view, there is provided, a clot removal system comprising a catheter comprising a proximal end, a distal end, and controller operating parameters and defining a lumen configured to be filled with a liquid column having a proximal portion, a vacuum source configured to supply vacuum, and a controller configured to carry out a control pattern of turning on and off the vacuum based upon the controller operating parameters and configured to receive the controller operating parameters in an automatic response to the catheter being operatively connected to at least one of the vacuum source and the controller and, responsive to the connection, to carry out the control pattern to change a level of vacuum at the distal end of the catheter.

With the objects in view, there is also provided a clot removal system comprising a catheter comprising a proximal end, a distal end, and controller operating parameters and defining a lumen configured to be filled with a liquid column having a proximal portion, a vacuum source configured to supply vacuum, a vacuum modulator configured to fluidically communicate with the vacuum from the vacuum source and with the proximal portion of the liquid column at the proximal end of the catheter, and a controller configured to carry out a control pattern of modulating the vacuum modulator based upon the controller operating parameters and configured to receive the controller operating parameters in an automatic response to the catheter being operatively connected to at least one of the vacuum modulator and the controller and, responsive to the connection, to carry out the control pattern to change a level of vacuum at the distal end of the catheter.

With the objects in view, there is also provided a clot removal system comprising a catheter comprising a proximal end, a distal end, and controller operating parameters and defining a lumen configured to be filled with a liquid column having a proximal portion, a vacuum source configured to supply vacuum, a vent container holding a vent liquid, a vent valve configured to fluidically communicate with the vent liquid in the liquid container and with the proximal portion of the liquid column at the proximal end of the catheter, a vacuum valve configured to fluidically communicate with the vacuum source and the proximal portion of the liquid column at the proximal end of the catheter, and a controller configured to carry out a control pattern of opening and closing the vent and vacuum valves based upon the controller operating parameters and configured to receive the controller operating parameters in an automatic response to the catheter being operatively connected to at least one of the vent valve, the vacuum valve, the vacuum source, and the controller and, responsive to the connection, to carry out the control pattern to change a level of vacuum at the distal end of the catheter.

With the objects in view, there is also provided a clot removal system comprising a catheter comprising a proximal end, a distal end, and controller operating parameters and defining a lumen configured to be filled with a liquid column having a proximal portion and a distal end, a vacuum source configured to supply vacuum, a vent container holding a vent liquid, a vent valve configured to fluidically communicate with the vent liquid in the liquid container and with the proximal portion of the liquid column at the proximal end of the catheter, a vacuum valve configured to fluidically communicate with the vacuum source and the proximal portion of the liquid column at the proximal end of the catheter, and a controller configured to carry out a control pattern to change a level of vacuum at the distal end of the catheter and, while changing the level of vacuum at the distal end of the catheter, to substantially prevent forward flow of the liquid at the distal end of the liquid column and configured to operate the vent and vacuum valves based upon the controller operating parameters in an automatic response to the catheter being operatively connected to at least one of the vent valve, the vacuum valve, the controller, and the vacuum source.

In accordance with another feature, the controller operating parameters are stored in the catheter and are provided to the controller responsive to the connection.

In accordance with a further feature, the catheter comprises an extension line having a first end connected to the catheter and a second end connected to at least one of the vacuum source and the controller and comprising the controller operating parameters and, responsive to the connection configured to provide the controller operating parameters to the controller and fluidically connecting the proximal end of the catheter with the vacuum source.

In accordance with an added feature, the controller is part of the vacuum source and the controller is configured to receive the controller operating parameters in the automatic response to the catheter being operatively connected to the vacuum source.

In accordance with an additional feature, the controller is separate from the vacuum source and the controller is configured to receive the controller operating parameters in the automatic response to the catheter being operatively connected to the controller.

In accordance with yet another feature, the extension line comprises additional controller operating parameters and, responsive to the connection is configured to provide the additional controller operating parameters to the controller.

In accordance with yet a further feature, the controller operating parameters comprise a catheter identifier and the controller is configured to receive the catheter identifier in the automatic response to the catheter being operatively connected to at least one of the vacuum source and the controller and, responsive to the connection, to carry out a pre-determined control pattern associated with the catheter identifier to change the level of vacuum at the distal end of the catheter.

In accordance with yet an added feature, the controller is part of the vacuum source and the controller is configured to receive the catheter identifier in the automatic response to the catheter being operatively connected to the vacuum source.

In accordance with yet an additional feature, the controller is separate from the vacuum source and the controller is configured to receive the catheter identifier in the automatic response to the catheter being operatively connected to the controller.

In accordance with again another feature, the controller operating parameters comprise a catheter identifier and the catheter comprises an extension line having a first end connected to the catheter and a second end connected to at least one of the vacuum source and the controller, comprising the catheter identifier, and, responsive to the connection, the extension line is configured to provide the catheter identifier to the controller and fluidically connects the proximal end of the catheter with the vacuum source.

In accordance with again a further feature, the controller is part of the vacuum source and the controller is configured to receive the catheter identifier in the automatic response to the extension line being operatively connected to the vacuum source.

In accordance with again an added feature, the controller is separate from the vacuum source and the controller is configured to receive the catheter identifier in the automatic response to the extension line being operatively connected to the controller.

In accordance with again an additional feature, the controller is configured to repeatedly and periodically carry out the control pattern.

In accordance with still another feature, the controller is one of a mechanical valve controller and an electronic valve controller.

In accordance with still a further feature, there is provided a control element operatively connected to the controller and, responsive to actuation of the control element, the controller carries out the control pattern.

In accordance with still an added feature, the controller is part of the vacuum source and the extension line fluidically connects the proximal end of the catheter to the vacuum source or the controller is separate from the vacuum source and is removably coupleable to the vacuum source and the extension line fluidically connects the proximal end of the catheter to the controller.

In accordance with still an additional feature, the operative connection of the catheter to the at least one of the vacuum source and the controller is an identification sub-assembly.

In accordance with another feature, the identification sub-assembly is disposed at the connection between the catheter and the extension line.

In accordance with a further feature, the operative connection of at least one of the catheter and the extension line to the at least one of the vacuum source and the controller is an identification sub-assembly.

In accordance with an added feature, the identification sub-assembly is at least one of an inductive sensor and sensed part, an RFID tag and reader, an NFC tag and reader, a 1-wire detection system, a 2-wire detection configuration, a Bluetooth low energy device, metallic touch pads, at least one passive resistor configuration, and at least one hall sensor.

In accordance with an additional feature, the identification sub-assembly is at least one of a manual user interface in which the user communicates to the controller which controller operating parameters to use with the catheter, a QR code and a QR code reader in which the QR code provided with the catheter communicates to the controller which controller operating parameters to use with the catheter, a bar code and a bar code reader in which the bar code provided with the catheter communicates to the controller which controller operating parameters to use with the catheter, and a punch-card and punch-card reader in which the punch-card provided with the catheter communicates to the controller which controller operating parameters to use with the catheter.

In accordance with yet another feature, the identification sub-assembly comprises a reader disposed at least one of at the vacuum source, at the controller as part of the vacuum source, and at the controller separable from the vacuum source.

In accordance with yet a further feature, the catheter comprises an extension line having a first end connected to the catheter and a second end opposite the first end and the operative connection of the catheter is an identification sub-assembly comprising a reader disposed at least one of, at the extension line, at the vacuum source, at the controller as part of the vacuum source, at the controller separate from the vacuum source, and at the controller separable from the vacuum source.

In accordance with yet an added feature, a manifold comprising the vacuum modulator and an output and an extension line fluidically connecting the proximal end of the catheter to the output of the manifold.

In accordance with yet an additional feature, there is provided an extension line operatively connected to at least one the vacuum modulator and the controller and fluidically connecting the proximal end of the catheter to at least one the vacuum modulator and the controller.

In accordance with again another feature, the operative connection of the catheter to the at least one of the vacuum modulator and the controller is an identification sub-assembly.

In accordance with again a further feature, a portion of the control pattern includes a time period where both the vent and vacuum valves are closed.

In accordance with again an added feature, the controller is configured to repeatedly and periodically carry out the control pattern with the vent and vacuum valves.

In accordance with again an additional feature, the controller is configured to open and close the vent and vacuum valves in a repeated cycle comprising a vent-only state in which the vacuum valve is closed and the vent valve is open, and a time of the vent-only state is no greater than 50 ms.

In accordance with still another feature, the lumen has a diameter of between approximately 0.038" and approximately 0.106" and the controller is configured to repeatedly and periodically carry out the control pattern of opening and closing the vent and vacuum valves at a frequency of between approximately 2 Hz and approximately 16 Hz.

In accordance with still a further feature, there is provided an extension line operatively connected to at least one of the vent valve, the vacuum valve, and the controller and fluidically connecting the proximal end of the catheter to at least one of the vent valve, the vacuum valve, and the controller.

In accordance with still an added feature, the operative connection of the catheter to the at least one of the vent valve, the vacuum valve, the vacuum source, and the controller is an identification sub-assembly.

In accordance with still an additional feature, the controller operating parameters comprises catheter identifiers, the catheter is one of a plurality of different catheters each having one of the catheter identifiers, and the controller is configured to store a plurality of pre-determined control patterns of opening and closing the vent and vacuum valves, each of the plurality of pre-determined control patterns being associated with one of the catheter identifiers and operate the vent and vacuum valves according to the pre-determined control pattern associated with the one catheter identifier in an automatic response to each of the catheters being operatively connected to the at least one of the vent valve, the vacuum valve, the controller, and the vacuum source.

In accordance with still an additional feature, the catheter is one of a plurality of different catheters each having a given set of the controller operating parameters and the controller is configured to receive the given set of the controller operating parameters and operate the vent and vacuum valves in the control pattern based upon the given set of controller operating parameters in an automatic response to each of the catheters being operatively connected to the at least one of the vent valve, the vacuum valve, the controller, and the vacuum source.

In accordance with still an additional feature, the change in the level of vacuum at the distal end of the catheter is one of greater than approximately 15 inHg and occurs in no greater than approximately 50 ms, greater than approximately 20 inHg and occurs in no greater than approximately 30 ms, and greater than approximately 25 inHg and occurs in no greater than approximately 20 ms.

In accordance with a concomitant feature, the controller is configured to open and close the vacuum and vent valves in a repeated cycle of the control pattern to retain a level of pressure at the distal end of the catheter at less than physiological pressure.

Although the systems, apparatuses, and methods are illustrated and described herein as embodied in an aspiration thrombectomy system and methods for thrombus removal with aspiration catheter, it is, nevertheless, not intended to be limited to the details shown because various modifications and structural changes may be made therein without departing from the spirit of the invention and within the scope and range of equivalents of the claims. Additionally, well-known elements of exemplary embodiments will not be described in detail or will be omitted so as not to obscure the relevant details of the systems, apparatuses, and methods.

Additional advantages and other features characteristic of the systems, apparatuses, and methods will be set forth in the detailed description that follows and may be apparent from the detailed description or may be learned by practice of exemplary embodiments. Still other advantages of the systems, apparatuses, and methods may be realized by any of the instrumentalities, methods, or combinations particularly pointed out in the claims.

Other features that are considered as characteristic for the systems, apparatuses, and methods are set forth in the appended claims. As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one of ordinary skill in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the systems, apparatuses, and methods of the invention that are regarded as novel, it is believed that the systems, apparatuses, and methods will be better understood from a consideration of the following description in conjunction with the drawing figures, in which like reference numerals are carried forward.

BRIEF DESCRIPTION OF THE DRAWINGS

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the systems, apparatuses, and methods. Advantages of embodiments of the systems, apparatuses, and methods will be apparent from the following detailed description of the exemplary embodiments thereof, which description should be considered in conjunction with the accompanying drawings in which:

FIG. 25 is a perspective view of an automatic aspiration thrombectomy system to be connected distally to an aspiration catheter and proximally to vacuum and vent lines and with a cam housing removed;

FIG. 26 is a fragmentary, top plan view of the aspiration thrombectomy system of FIG. 25 with diagrammatic illustration of the aspiration catheter and the vacuum and vent lines;

FIG. 27 is an elevational view of a proximal side of the aspiration thrombectomy system of FIG. 25;

FIG. 28 is an elevational view of a bearing side of the aspiration thrombectomy system of FIG. 25;

FIG. 34 is a perspective view of the aspiration thrombectomy system of FIG. 25 with the motor assembly housing removed;

FIG. 35 is a top plan view of the aspiration thrombectomy system of FIG. 26 with the motor assembly housing removed;

FIG. 36 is an elevational view of the aspiration thrombectomy system of FIG. 27 with the motor assembly housing removed;

FIG. 37 is an elevational view of the bearing side of the aspiration thrombectomy system of FIG. 28 with the motor assembly housing removed;

DETAILED DESCRIPTION OF THE EMBODIMENTS

Figure 1:
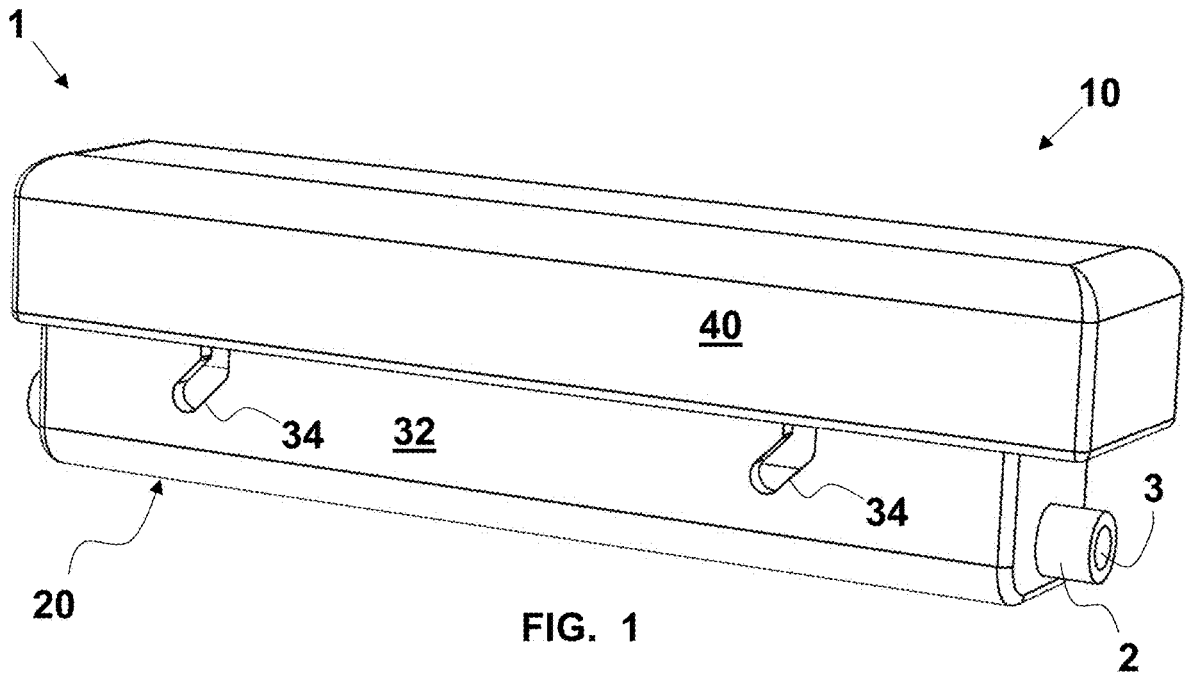
FIG. 1 is a fragmentary, perspective view of an exemplary embodiment of a controller for a thrombectomy aspiration catheter in an unactuated state.

As required, detailed embodiments of the systems, apparatuses, and methods are disclosed herein; however, it is to be understood that the disclosed embodiments are merely exemplary of the systems, apparatuses, and methods, which can be embodied in various forms. Therefore, specific structural and functional details disclosed herein are not to be interpreted as limiting, but merely as a basis for the claims and as a representative basis for teaching one skilled in the art to variously employ the systems, apparatuses, and methods in virtually any appropriately detailed structure. Further, the terms and phrases used herein are not intended to be limiting; but rather, to provide an understandable description of the systems, apparatuses, and methods. While the specification concludes with claims defining the features of the systems, apparatuses, and methods that are regarded as novel, it is believed that the systems, apparatuses, and methods will be better understood from a consideration of the following description in conjunction with the drawing figures, in which like reference numerals are carried forward.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Alternate embodiments may be devised without departing from the spirit or the scope of the invention. Additionally, well-known elements of exemplary embodiments of the systems, apparatuses, and methods will not be described in detail or will be omitted so as not to obscure the relevant details of the systems, apparatuses, and methods.

Before the systems, apparatuses, and methods are disclosed and described, it is to be understood that the terminology used herein is for the purpose of describing particular embodiments only and is not intended to be limiting. The terms "comprises," "comprising," or any other variation thereof are intended to cover a non-exclusive inclusion, such that a process, method, article, or apparatus that comprises a list of elements does not include only those elements but may include other elements not expressly listed or inherent to such process, method, article, or apparatus. An element proceeded by "comprises . . . a" does not, without more constraints, preclude the existence of additional identical elements in the process, method, article, or apparatus that comprises the element. The terms "including" and/or "having," as used herein, are defined as comprising (i.e., open language). The terms "a" or "an", as used herein, are defined as one or more than one. The term "plurality," as used herein, is defined as two or more than two. The term "another," as used herein, is defined as at least a second or more. The description may use the terms "embodiment" or "embodiments," which may each refer to one or more of the same or different embodiments.

The terms "coupled" and "connected," along with their derivatives, may be used. It should be understood that these terms are not intended as synonyms for each other. Rather, in particular embodiments, "connected" may be used to indicate that two or more elements are in direct physical or electrical contact with each other. "Coupled" may mean that two or more elements are in direct physical or electrical contact (e.g., directly coupled). However, "coupled" may also mean that two or more elements are not in direct contact with each other, but yet still cooperate or interact with each other (e.g., indirectly coupled).

For the purposes of the description, a phrase in the form "A/B" or in the form "A and/or B" or in the form "at least one of A and B" means (A), (B), or (A and B), where A and B are variables indicating a particular object or attribute. When used, this phrase is intended to and is hereby defined as a choice of A or B or both A and B, which is similar to the phrase "and/or". Where more than two variables are present in such a phrase, this phrase is hereby defined as including only one of the variables, any one of the variables, any combination of any of the variables, and all of the variables, for example, a phrase in the form "at least one of A, B, and C" means (A), (B), (C), (A and B), (A and C), (B and C), or (A, B and C).

Relational terms such as first and second, top and bottom, and the like may be used solely to distinguish one entity or action from another entity or action without necessarily requiring or implying any actual such relationship or order between such entities or actions. The description may use perspective-based descriptions such as up/down, back/front, top/bottom, and proximal/distal. Such descriptions are merely used to facilitate the discussion and are not intended to restrict the application of disclosed embodiments. Various operations may be described as multiple discrete operations in turn, in a manner that may be helpful in understanding embodiments; however, the order of description should not be construed to imply that these operations are order dependent.

As used herein, the term "about" or "approximately" applies to all numeric values, whether or not explicitly indicated. These terms generally refer to a range of numbers that one of skill in the art would consider equivalent to the recited values (i.e., having the same function or result). In many instances these terms may include numbers that are rounded to the nearest significant figure. As used herein, the terms "substantial" and "substantially" means, when comparing various parts to one another, that the parts being compared are equal to or are so close enough in dimension that one skill in the art would consider the same. Substantial and substantially, as used herein, are not limited to a single dimension and specifically include a range of values for those parts being compared. The range of values, both above and below (e.g., "+/−" or greater/lesser or larger/smaller), includes a variance that one skilled in the art would know to be a reasonable tolerance for the parts mentioned.

It will be appreciated that embodiments of the systems, apparatuses, and methods described herein may be comprised of one or more conventional processors and unique stored program instructions that control the one or more processors to implement, in conjunction with certain non-processor circuits and other elements, some, most, or all of the functions of the systems, apparatuses, and methods described herein. The non-processor circuits may include, but are not limited to, signal drivers, clock circuits, power source circuits, and user input and output elements. Alternatively, some or all functions could be implemented by a state machine that has no stored program instructions, or in one or more application specific integrated circuits (ASICs) or field-programmable gate arrays (FPGA), in which each function or some combinations of certain of the functions are implemented as custom logic. Of course, a combination of these approaches could also be used. Thus, methods and means for these functions have been described herein.

The terms "program," "software," "software application," and the like as used herein, are defined as a sequence of instructions designed for execution on a computer system or programmable device. A "program," "software," "application," "computer program," or "software application" may include a subroutine, a function, a procedure, an object method, an object implementation, an executable application, an applet, a servlet, a source code, an object code, any computer language logic, a shared library/dynamic load library and/or other sequence of instructions designed for execution on a computer system.

Herein various embodiments of the systems, apparatuses, and methods are described. In many of the different embodiments, features are similar. Therefore, to avoid redundancy, repetitive description of these similar features may not be made in some circumstances. It shall be understood, however, that description of a first-appearing feature applies to the later described similar feature and each respective description, therefore, is to be incorporated therein without such repetition.

Described now are exemplary embodiments. Referring now to the figures of the drawings in detail and first, particularly to FIGS. 1 to 13, there is shown a first exemplary embodiment of a one-handed controller 10 for an aspiration thrombectomy system 1 utilizing a vacuum tube 2. The controller 10 comprises a first handle part 20 and a second handle part 40. The first handle part 20 is connected to and holds the vacuum tube 2 and, therefore, is also referred to as a handle base. The second handle part 40 moves with respect to the first handle part 20 and, therefore, the second handle part 40 is also referred to as a compressor-actuator 40.

In an exemplary embodiment, the first handle part 20 has a distal tube anchor 22 and a proximal tube anchor 24. In this embodiment, the distal and proximal tube anchors 22, 24 are in the form of hollow tubes through which the vacuum tube 2 traverses. The distal and proximal tube anchors 22, 24 hold the vacuum tube 2 therein substantially without compressing the vacuum tube 2 (and thereby does not reduce or close the inner vacuum channel 3). The vacuum tube 2 can be of many materials, including latex, silicone, Pebax®, polyurethane, polyvinyl chloride, or other synthetic rubber. Exemplary sizes for the vacuum tube 2 have an inner diameter (I.D.) of approximately 0.055 to 0.095 inches. One exemplary embodiment for retaining the vacuum tube 2 is an adhesive that bonds the material of the vacuum tube 2 to the interior lumens of the tubular tube anchors 22, 24. In this exemplary embodiment, the vacuum tube 2 is fixed to the first handle part 20. In an alternative embodiment, the first handle part 20 is a clamshell having two first handle part halves (not illustrated) that open to receive the cylindrical vacuum tube 2 and, when closed thereupon, the tube anchors 22, 24 tightly grip the vacuum tube 2 therein substantially without closing or occluding the vacuum channel 3 of the vacuum tube 2. In one exemplary clamshell embodiment, the first handle part 20 is split horizontally at the dashed line in FIG. 2 with a hinge, allowing a portion of the vacuum tube 2 to be inserted into and removed from the distal and proximal tube anchors 22, 24. A lock secures the vacuum tube 2 therein until the user desires removal. The hinge is useful to allow the surgeon to reposition the controller 10 along the vacuum tube 2.

Figure 13:
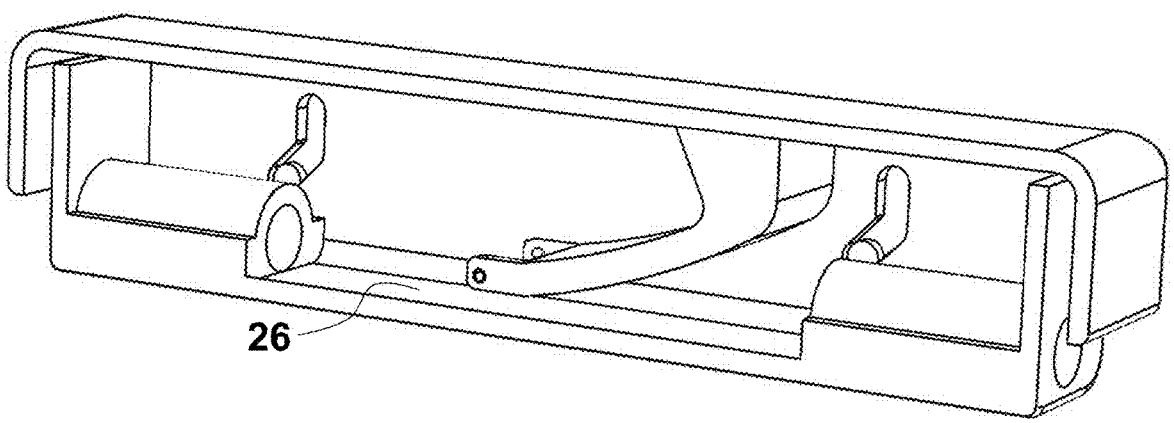
FIG. 13 is a longitudinal cross-sectional view of the controller of FIG. 9 with the compression roller and the aspiration catheter removed.

The exemplary embodiment of the distal and proximal tube anchors 22, 24 are separated from one another over a distance. Between the distal and proximal tube anchors 22, 24 of the first handle part 20 is a compression floor 26. When installed within the first handle part 20, the vacuum tube 2 lays against the compression floor 26 between the distal and proximal tube anchors 22, 24 substantially without closing or occluding the vacuum channel 3. FIG. 13 illustrates the compression floor 26 of first handle part 20 with the vacuum tube 2 removed.

The first handle part 20 has a hollow interior that defines a set of parallel lateral walls 32 on either side of the vacuum tube 2. The first handle part 20 comprises a compression cam assembly 30 that permits the second handle part 40 to move in two directions with respect to the first handle part 20. More specifically, in the exemplary embodiment, the compression cam assembly 30 comprises a set of slots 34 formed in the lateral walls 32 of the first handle part 20. As shown in the enlarged view of FIG. 3, these slots 34 have a vertical extent 35 and an angled extent 36. The vertical extent 35 has a vertical length and the angled extent 36 has a vector length that is comprised of a second vertical extent 37 and a horizontal extent 39. Accordingly, as explained below, the slots 34 provide a cam surface for movement of the second handle part 40 in the same shape as the slot 34.

In the exemplary embodiment, to contact the first and second handle parts 20, 40 together, the second handle part 40 has a hollow interior into which the first handle part 20 is inserted and projects. (In an alternative embodiment, the first handle part 20 has a hollow interior into which the second handle part 40 is inserted and projects.) A width between interior facing lateral surfaces of the hollow compartment of the second handle part 40 is approximately equal to the width of the exterior surfaces of the lateral walls 32 such that the second handle part 40 can move up and down on the first handle part 20 tightly but smoothly with little or substantially no friction. In comparison, the length between interior facing longitudinal surfaces of the hollow compartment of the second handle part 40 is greater than the length of the exterior surfaces of the longitudinal walls 38. The difference in length is sufficiently long enough to allow the second handle part 40 to move along the horizontal extent 39 longitudinally parallel with the vacuum tube 2 throughout the horizontal extent 39.

Figure 5:
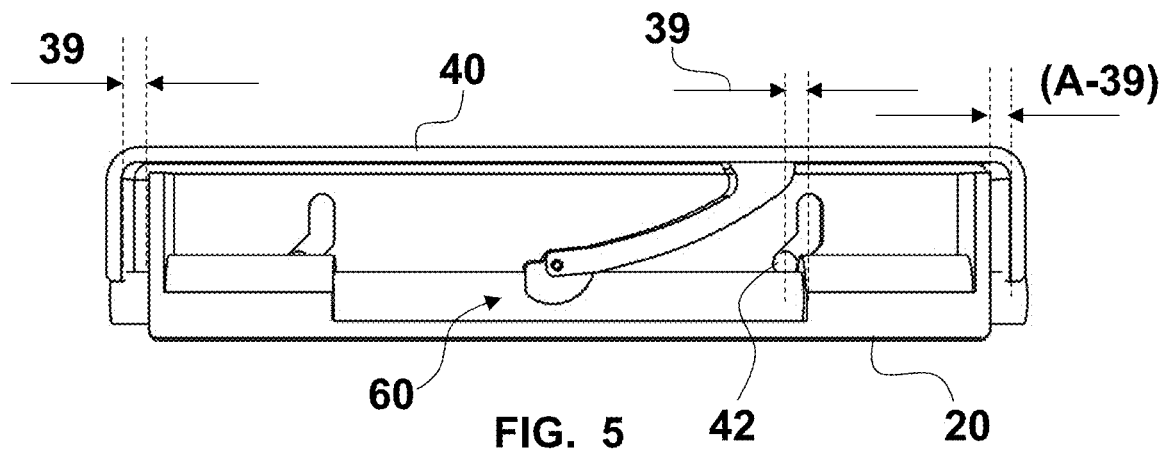
FIG. 5 is a fragmentary, longitudinal cross-sectional view of the controller of FIG. 1 in an actuated state.

Movement of the compressor-actuator 40 with respect to the handle base 20 follows the slots 34 by providing the compressor-actuator 40 with bosses 42 protruding from the interior facing surfaces of the lateral walls 42 of the hollow compartment of the compressor-actuator 40; one circular boss 42 is associated with each of the slots 34. In this way, movement of the compressor-actuator 40 is guided by and restricted by the shape of the slots 34. In an unactuated state of the controller 10, shown in FIGS. 1, 2, and 4, the bosses 42 reside at the end of the vertical extent 35, which in the exemplary embodiment is at the uppermost end of the slot 34. (It is noted that the embodiment shown in FIGS. 1 to 13 provide four slots 34 and four bosses 42. This number is merely exemplary. The cam surface of the slots 34, the extents 35, 36 of the slots 34, and the cam follower of the bosses 42 can take any form or shape that causes the controller to operate as described herein.) As seen most clearly in FIG. 4, a distance A between an interior of the proximal longitudinal wall 38 of the compressor-actuator 40 and an exterior of the proximal wall of the first handle part 20 is longer than the horizontal extent 39 (i.e., |A|>|39|). When the compressor-actuator 40 is fully actuated as shown in FIG. 5, the bosses 42 travel to the opposite (lowermost) end of the slot 34. The compressor-actuator 40, therefore, has traveled a vertical distance equal to the vertical movement of the bosses 42 within the vertical and angled extents 35, 36 and has traveled a horizontal distance equal to the horizontal extent 39. The exemplary embodiments of the first and second handle parts 20, 40 have the interior surface of the distal longitudinal wall of the compressor-actuator 40 touching the exterior surface of the distal longitudinal wall of the handle base 20, this touch being indicated with arrows B in FIG. 4 (i.e., |B|=0). When the compressor-actuator 40 is fully actuated, therefore, these two distal longitudinal walls separate to a distance equal to the horizontal extent 39. Likewise, the distance between an exterior surface of the proximal longitudinal wall of the handle base 20 and an interior surface of the proximal longitudinal wall of the compressor-actuator 40 shortens from A by a length equal to the horizontal extent 39 (i.e., (A-|39|)), which is illustrated in FIG. 5. Alternately, a four-bar linkage could be provided to join 20 and 40 to create the same motion as the cam slots and bosses.

What becomes apparent from movement of the compressor-actuator 40 following the slots 34 is how an extrusion compressor 50 connected to the compressor-actuator 40 operates during this movement. The exemplary embodiment of the extrusion compressor 50 in FIGS. 1, 2 and 4 to 13 has the extrusion compressor 50 project from an interior surface of a ceiling of the hollow compartment of the compressor-actuator 40 downwards towards the handle base 20. In particular, the extrusion compressor 50 projects downwards towards the compression floor 26 of the handle base 20. The extrusion compressor 50 has a base 52 attached to the second handle part 40. A flex arm 54 projects from the base 52 and extends towards the compression floor 26. In the exemplary embodiment, the flex arm 54 is thinner than the base 52. A material from which the base 52 and flex arm 54 are made is not substantially rigid and, therefore, responsive to moving downwards to have a portion of the extrusion compressor 50 touch the compression floor 26 before the entire vertical movement of the compressor-actuator 40 is complete, the flex arm 54 flexes. Example materials for the base 52 and flex arm 54 include ABS, polycarbonate and Nylon®, polypropylene, polyurethane, or other thermoplastic or thermoplastic elastomer and/or fiber filled ABS, polycarbonate and Nylon®. At a distal end of the flex arm 54 is a gear flange 56 shaped to hold thereat a compression roller 60. The gear flange 56 has axle ports in which an axle 62 of the compression roller 60 resides. When installed between the interior sides of the gear flange 56, the compression roller 60 becomes fixed to the gear flange 56 in all directions except for rotational movement of the compression roller 60 about a rotation axis 64 of the roller 60; in other words, the roller 60 is allowed to rotate about the axis 64.

It is noted that the extrusion compressor 50 shown is an exemplary embodiment. Different mechanical structures performing the same function can be used. For example, the base 52 and flex arm 54 can be replaced with a single beam that is hinged to the ceiling of the interior hollow of the compressor-actuator 40 and biased with a bias device (e.g., a spring) towards the compression floor 26 such that the point of the compression roller 60 touches the vacuum tube 2 as shown in FIG. 2 enough to grip the vacuum tube 2 but substantially not reduce the cross-sectional area of the vacuum channel 3.

Figure 6:
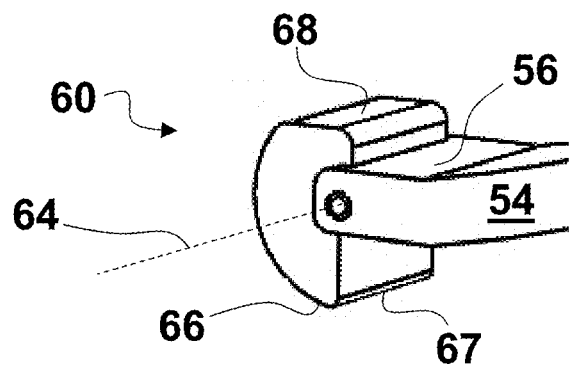
FIG. 6 is a fragmentary, enlarged, perspective view of a portion of an extrusion compressor of the controller of FIG. 1.
Figure 7:
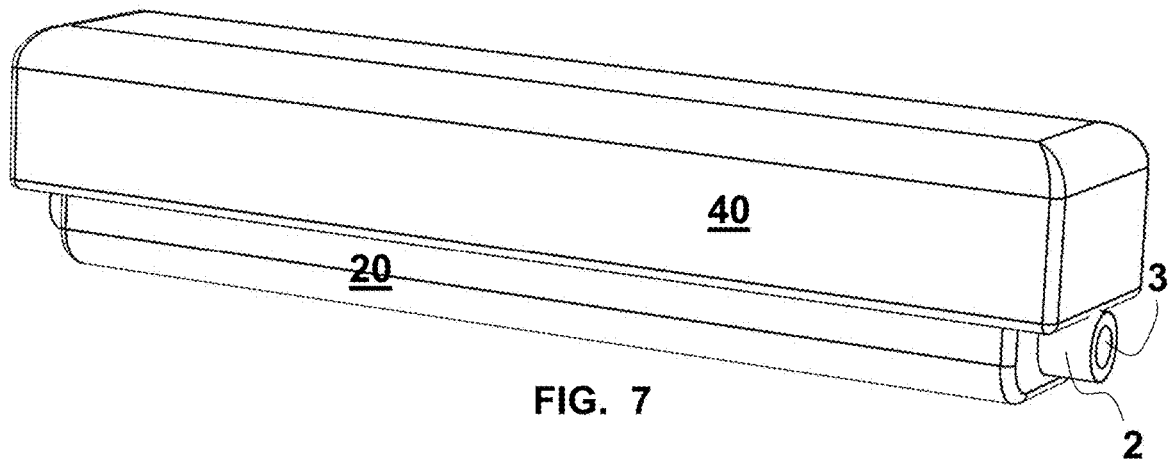
FIG. 7 is a fragmentary, perspective view of the controller of FIG. 1 in the actuated state.
Figure 8:
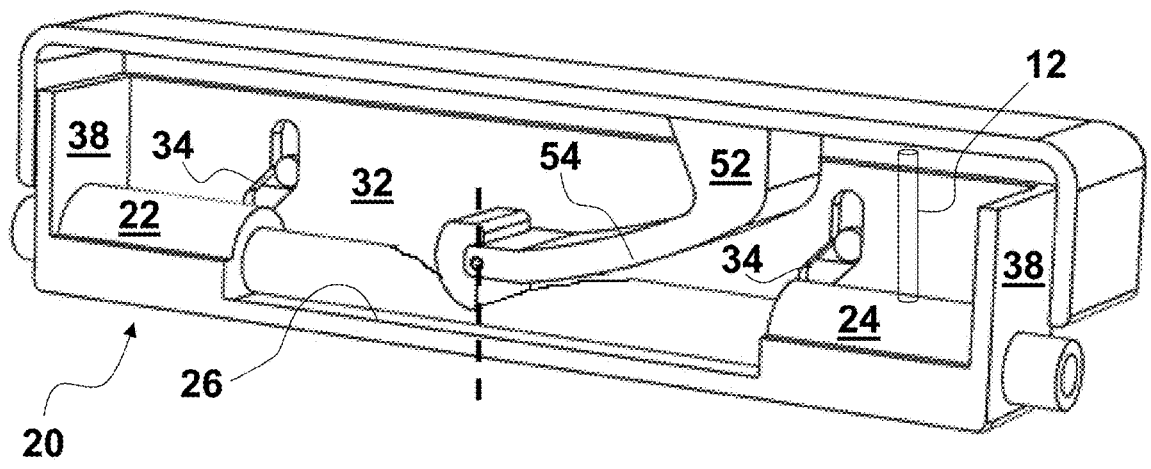
FIG. 8 is a fragmentary, perspective and partially longitudinal cross-sectional view of the controller of FIG. 7.

Rotation of the roller 60 is dependent upon how the roller 60 moves towards the vacuum tube 2 and along the vacuum tube 2. In this regard, the compression roller 60 has an exterior contact surface 66 that contacts the vacuum tube 2 in various ways when the compressor-actuator 40 is moved towards the handle base 20. As shown in FIG. 6, a longitudinal cross-section of the exterior surface 66 is approximately in the shape of a nautilus (alternatively, the shape can be cylindrical). The exterior surface 66 has a contact point 67, which is in contact with the exterior surface of the vacuum tube 2 in the unactuated state of the compressor-actuator 40 as shown in FIG. 2 (the vacuum channel 3 is unoccluded with a substantially patent and open cross-ssection). As the compressor-actuator 40 is actuated, the compressor-actuator 40 travels along the vertical extent 35. This moves the contact point 67 towards the compression floor 26. When the compressor-actuator 40 has travelled along the entirety of the vertical extent 35, as shown in FIGS. 7 and 8, the contact point 67 has moved against the vacuum tube 2 to occlude the vacuum channel 3 completely. At the stage where the bosses 42 are at this transition point from the vertical extent 35 to the angled extent 36, the contact point 67 is as far towards the compression floor 26 as it can move in that direction—because the thickness of the vacuum tube 2 prevents further movement of the contact point 67 towards the compression floor 26.

Figure 9:
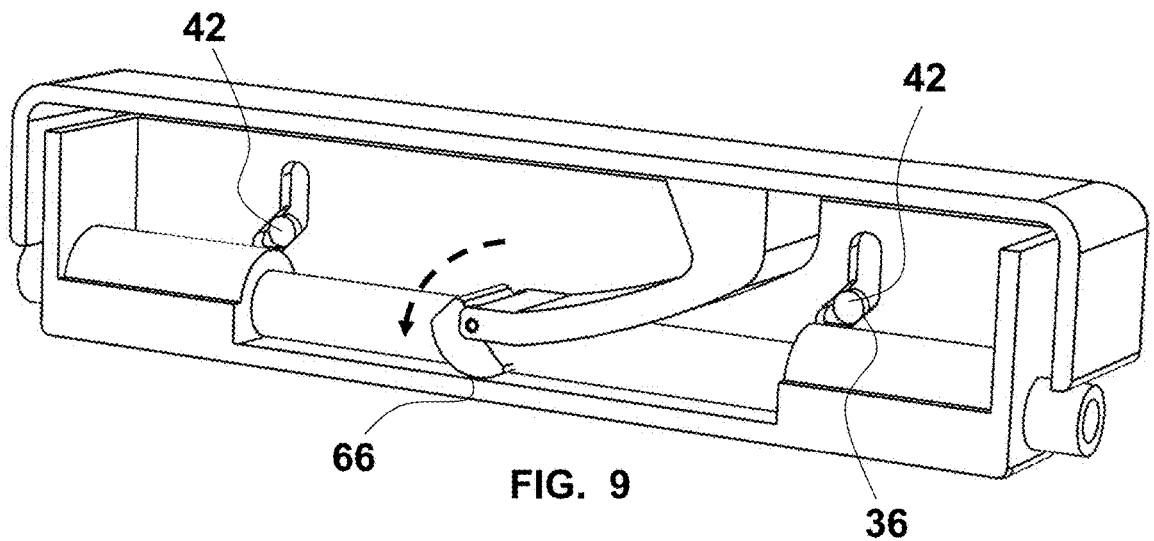
FIG. 9 is a fragmentary, perspective and longitudinal cross-sectional view of the controller of FIG. 1 in an intermediate actuated state with the compression roller occluding the aspiration catheter and partially rolled to cause fluid column shift.
Figure 10:
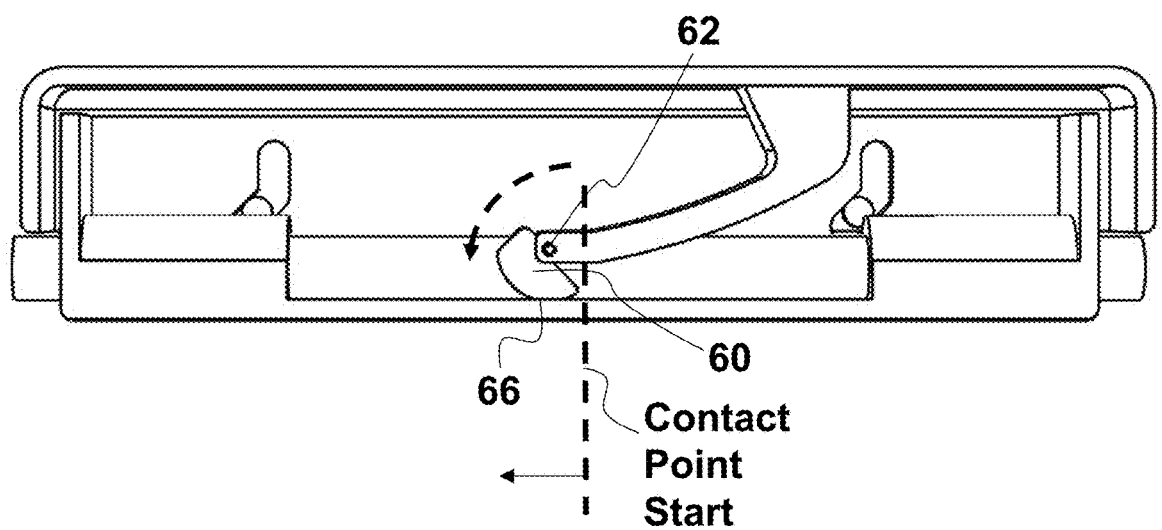
FIG. 10 is a fragmentary, longitudinal cross-sectional view of the controller of FIG.
Figure 11:
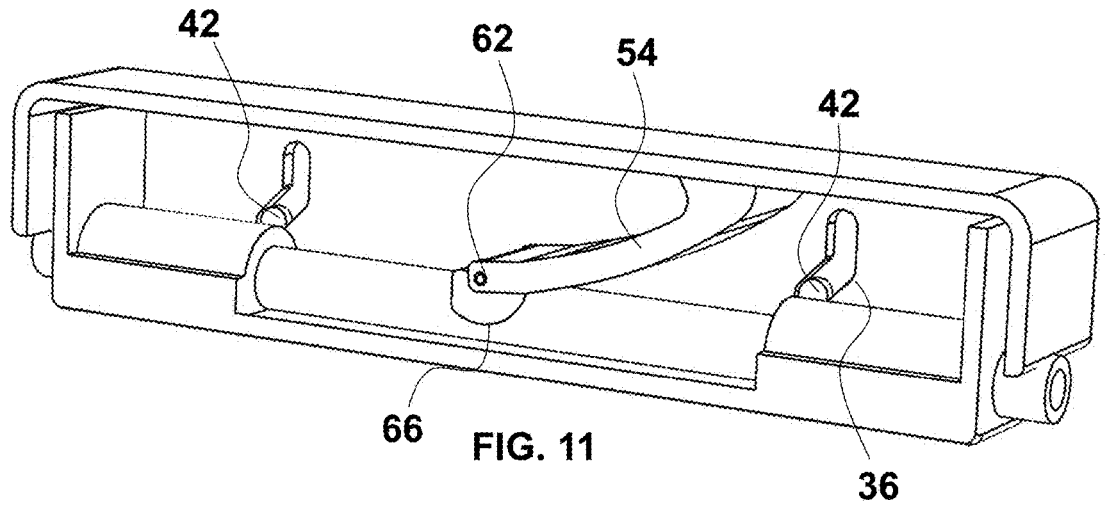
FIG. 11 is a fragmentary, perspective and longitudinal cross-sectional view of the controller of FIG. 1 in the actuated state with the compression roller occluding the aspiration catheter and fully rolled to cause fluid column shift.
Figure 12:
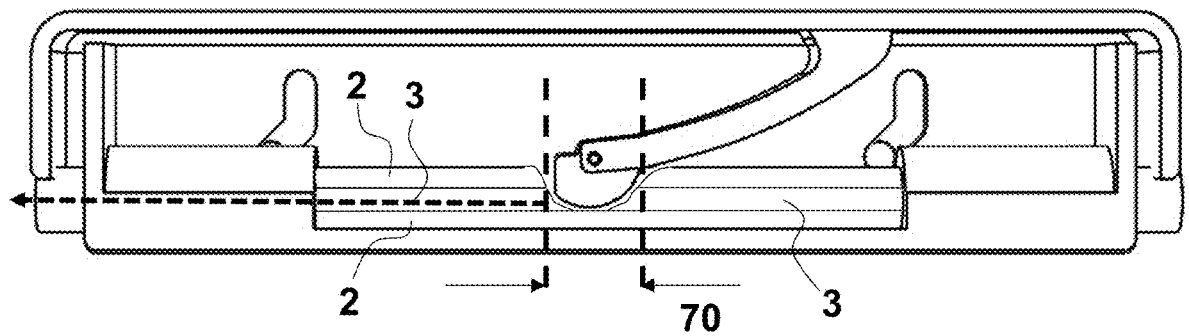
FIG. 12 is a fragmentary, longitudinal cross-sectional view of the controller of FIG. 11.

In a procedure where the vacuum tube 2 is used in a thrombectomy, the vacuum channel 3 will be filled with a fluid, i.e., blood. When the vacuum channel 3 is completely occluded, the blood that fills up the vacuum channel 3 from the contact point 67 of the compression roller 60 distally to the distal end of the vacuum channel 3 defines a column of fluid, which fluid is not compressible. The controller 10 is configured to apply the extrusion compressor 50 and the compression roller 60 to move this column of fluid a shift distance 70 in the distal direction. An exemplary volume of the shift distance is approximately 0.001 ml to approximately 1.0 ml, in particular, approximately 0.1 ml to approximately 0.5 ml. An exemplary length of the shift distance 70 is approximately 0.5 mm to approximately 30 mm, in particular, approximately 0.5 mm to approximately 15 mm. To effect such a movement, the compressor-actuator 40 is moved further in the direction towards the handle base 20, which means that that the bosses 42 travel along and through to the end of the angled extent 36. Because the contact point 67 is already as far towards the compression floor 26 as it can move in that direction (i.e., when the bosses 42 are at the transition point from the vertical extent 35 to the angled extent 36), the extrusion compressor 50 has no other way to move than to flex the flex arm 54 and/or to roll the compression roller 60. The contact surface 66 of the compression roller 60 is shaped to roll (counterclockwise in the views of FIGS. 2 and 8 to 12) against an upper surface of the vacuum tube 2. FIGS. 9 and 10 illustrate the rolling start of the compression roller 60 at a point where the bosses 42 are approximately halfway to the distal end of the slot 34 within the angled extent 36. (It is noted that limitation of the computer software that generates FIGS. 9 to 12 do not allow for displaying a realistic view of how the vacuum tube 2 compresses as the compression roller 60 rotates. These figures, therefore, illustrate an approximation of the compression roller 60 rolling on and over the shift distance 70 of the vacuum tube 2.) The contact point 67 of the compression roller 60 is offset from the rotation axis 64 towards the contact surface 66. This forms an over center, or toggle, such that the initial rolling motion of the compression roller must first force the contact point 67 over the center of the rotation axis 64. In such a configuration, not only does the compression roller 60 roll once the bosses 42 of the compression-actuator 40 start traveling in the angled extent 37, but there is also a tactile feedback transmitted to the compression-actuator 40 once the axle 62 moves slightly forward. This feedback, when felt by the user, indicates to the user that the contact surface 66 of the compression roller 60 has rolled onto a portion of the vacuum tube 2 and, as it moves along the vacuum tube 2, squeezes that portion to translate the fluid column in the distal direction of the vacuum tube 2. With complete movement of the compression-actuator 40 towards the handle base 20 as shown in FIGS. 11 and 12, the compression roller 60 has completed its defined rotation over the vacuum tube 2 and, in doing so, has squeezed a segment of the vacuum channel 3 from proximal to distal over the length to shift the fluid column distally to a length equal to the shift distance 70.

Figure 2:
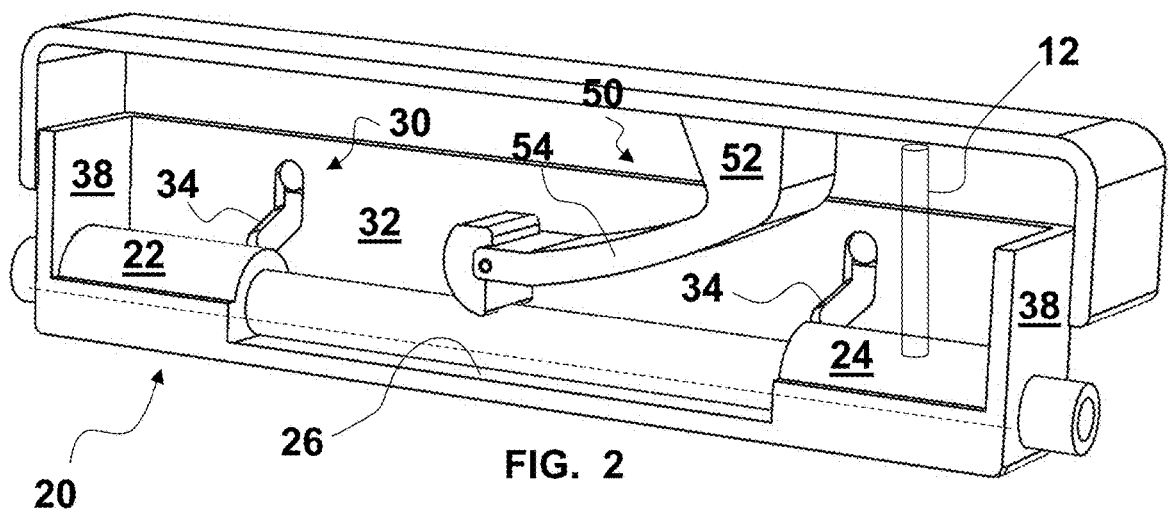
FIG. 2 is a fragmentary, perspective, longitudinal cross-sectional view of the controller of FIG. 1.
Figure 3:
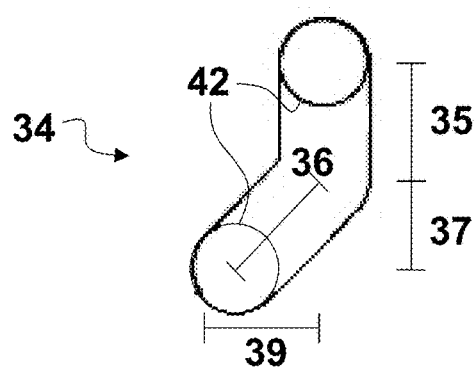
FIG. 3 is an enlarged, diagrammatic, side elevational view of a compression cam assembly of the controller of FIG. 1.
Figure 4:
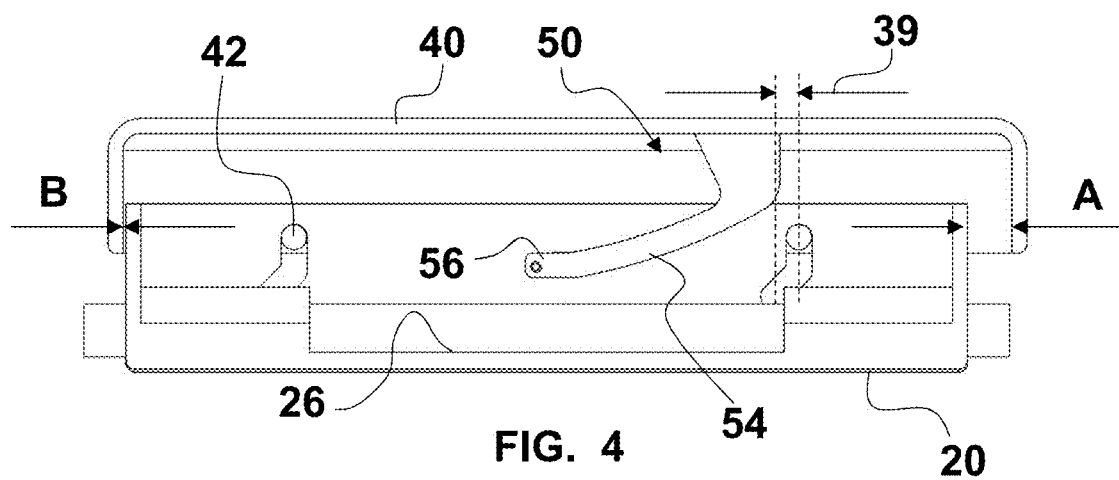
FIG. 4 is a fragmentary, longitudinal cross-sectional view of the controller of FIG. 1 with a compression roller removed.

To return the controller 10 to the initial, unactuated state shown in FIGS. 1 and 2, for example, a bias device 12 is interposed between any surface of the interior hollow of the compression-actuator 40 and any surface of interior hollow of the handle base 20. In the exemplary embodiment shown in FIGS. 2 and 8, the bias device 12 is disposed between the surface of the ceiling within the interior hollow of the compression-actuator 40 and an upper surface of the proximal tube anchor 24. This configuration for the bias device 12 is merely exemplary and any return spring or similar mechanical device can be placed and used. When the user releases pressure on the compression-actuator 40, the flex arm 54 and/or the bias device 12 causes the compression-actuator 40 to return to the initial, unactuated state. This action rolls the compression roller 60 in the opposite direction (i.e., the progression from FIG. 11 to FIG. 9 to FIG. 8). As the distal end of the vacuum channel 3 experiences positive pressure from the patient and also from the increase in volume as the crushed tube rebounds, the fluid column retreats proximally back into the vacuum channel 3 and, when the compression roller 60 releases from the vacuum tube 2 to cease occluding the vacuum channel 3, vacuum being placed in the vacuum channel 3 from a vacuum pump 80 proximal to the controller 10 automatically reestablishes and draws the fluid column through the segment of the vacuum tube 2 within the controller 10.

As set forth herein, the vacuum tube 2 is sized to lay against the compression floor 26 on one side and to have the point of the compression roller 60 touch the outer surface of the vacuum tube 2 just slightly enough to grip the vacuum tube 2 but substantially not reduce the cross-sectional sectional area of vacuum channel 3. In an embodiment where the vacuum tube 2 is not fixed within the handle base 20, the compression roller 60 is provided with a non-illustrated bias device that biases the compression roller 60 rotationally into a position shown in FIG. 2. This bias compensates in a situation where the vacuum tube 2 is not touching the compression roller in the unactuated position of the compressor-actuator 40.

Figure 14:
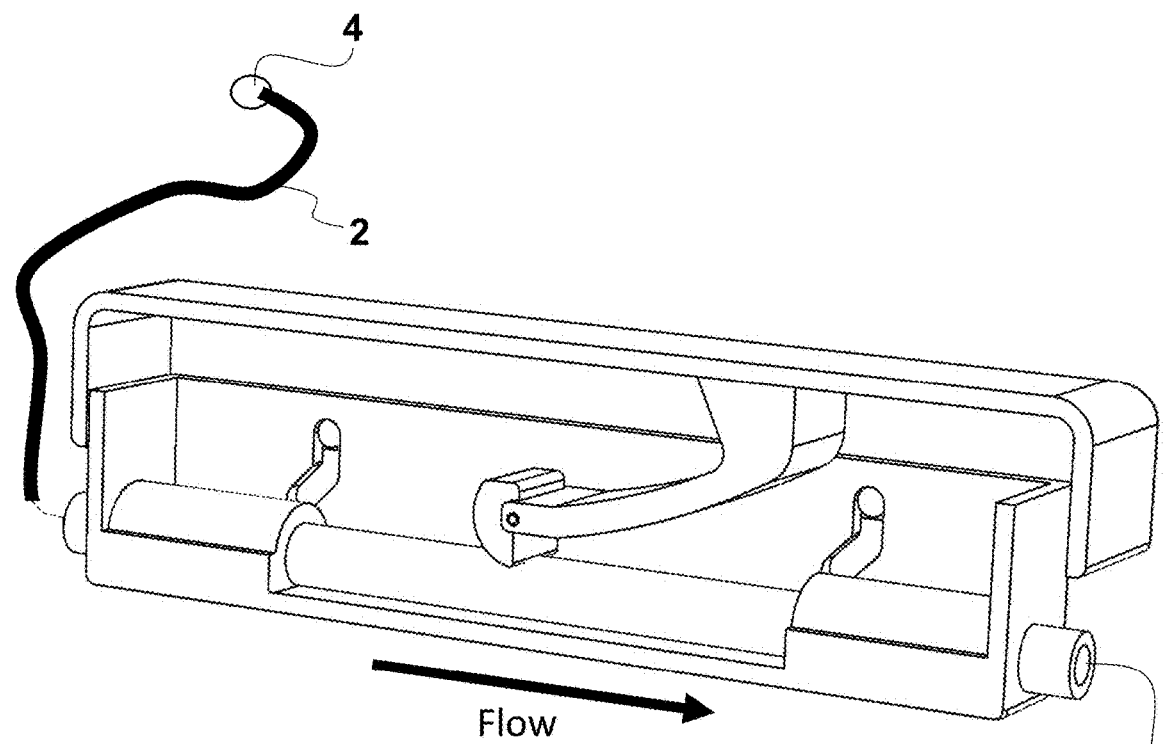
FIG. 14 is a fragmentary, perspective and longitudinal cross-sectional view of the controller of FIG. 1 in the unactuated state and diagrammatically connected to a distal portion of the aspiration catheter with a thrombus lodged in a distal opening of a vacuum channel.
Figure 15:
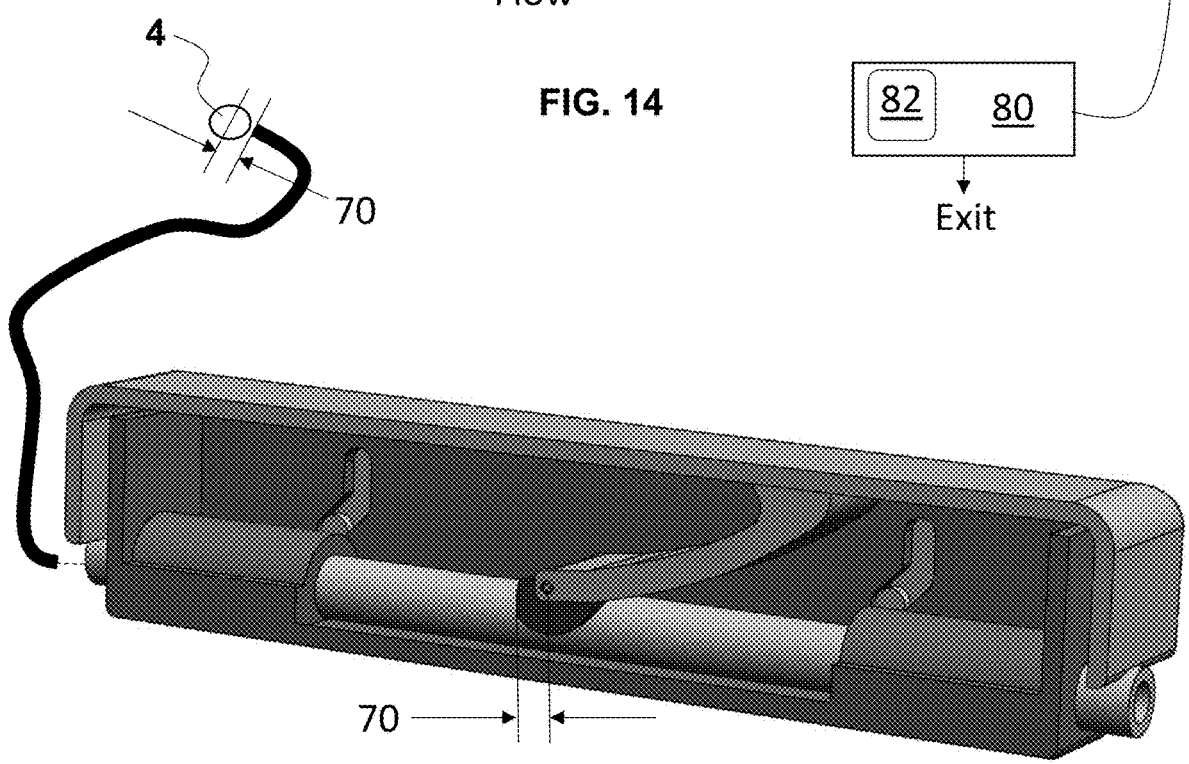
FIG. 15 is a fragmentary, perspective and longitudinal cross-sectional view of the controller of FIG. 12 in the actuated state with the column shift that distally dislodges the thrombus from the distal opening of the vacuum channel.

With a configuration as described, the controller 10 is to be used with a vacuum tube 2 that is or is part of a thrombectomy aspiration catheter. Such use is described with regard to FIGS. 14 and 15, in which the vacuum lumen 3 is shown as being an aspiration controller that, distal to the controller 10, is threaded through vasculature and up to a thrombus 4, which in the form of a blood clot, that has corked within or at the distal opening of the vacuum channel 3. On the proximal side of the controller 10, the vacuum channel 3 is fluidically connected to the vacuum pump 80. As indicated above, thrombi typically are trapped at the end of an aspiration catheter and removing the entire catheter from the patient when that occurs is not desirable. The inventors have discovered that removal of the catheter can be prevented using the controller 10. More particular, when the distal end of the vacuum tube 2 is clogged by a thrombus, the controller 10 is actuated to occlude all flow through the vacuum channel 3. This occurs by the first movement of the compressor-actuator 40 towards the handle base 20. The controller 10 is actuated to cause the fluid column to shift distally to the shift distance 70. This imparts a controlled reversal of flow to the fluid column within the vacuum channel 3 that slightly translates the thrombus to a prescribed shift distance 70 distally relative to the distal opening of the vacuum channel 3. During a third and final phase, the user releases actuation of the controller 10 to reset the fluid column within the vacuum channel 3 and, once again, allows the fluid to flow freely. The inventors have discovered that such movement causes either a repositioning of the thrombus or a deformation of the thrombus or both and that this movement allows the thrombus to pass entirely into and through the vacuum channel 3 where such passage was not possible before.

Figure 24:
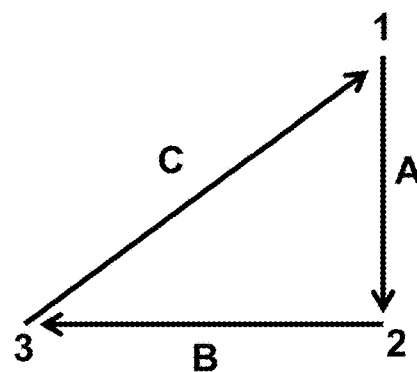
FIG. 24 is a cycle flow diagram of the operation of exemplary embodiments of the controller with the vacuum booster and the thrombus trap.

Operation of the controller 10 is explained with regard to the system cycle diagram of FIG. 24.

State 1: Normal aspiration is occurring. The vacuum channel 3 is not occluded. The controller 100 is in a rest state where the vacuum pump 80 is connected to the vacuum channel 3.

Transition A—Occlusion: Thrombus 4 occludes distal end of vacuum channel 3. Unclogging controller 10 actuates to occlude vacuum channel 3 and stop vacuum flow distal of the controller 10.

State 2: Flow through the vacuum channel 3 has stopped.

Transition B—Unclogging: Controller 10 continues actuation to cause reverse flow in vacuum channel 3 for a metered volumetric column shift.

State 3: Flow reversal stops.

Transition C—Return Column Shift: Controller 10 is reversed to return column and accelerate thrombus 4 into catheter tip by reconnecting the vacuum pump 80 to the vacuum channel 3.

Return to State 1 and Repeat: Normal aspiration occurs.

The inventors further discovered that greater accelerations of the thrombus into the catheter provide proportionally quicker aspirations. A magnitude of the thrombus' impact velocity, and therefore its kinetic energy, when it impacts the aspiration catheter's distal tip, affects the amount of the thrombus that is deformed to fit within the diameter of the vacuum channel 3. When a catheter is extended to a thrombus that is lodged in a vessel, e.g., a vessel within the brain, the controller 10 is not needed until the thrombus 4 is stuck at the distal opening of the vacuum channel 3. Thus, the thrombus does not have any distance to move in order to accelerate towards the opening of the vacuum channel 3. Imparting the shift distance to the thrombus as described maximizes the kinetic energy of the thrombus at the point when it impacts the catheter's tip. The thrombus' acceleration (and therefore its kinetic energy) are generated by a pressure differential between intracranial pressure and the effective aspiration pressure at the catheter's tip. For the thrombus to accelerate, both it and the fluid column within the catheter system must attain a velocity. After catheters are occluded, the fluid velocity within the catheter is substantially zero. In conventional catheter architecture, the pressure that attempts to accelerate this fluid column is provided solely by an external vacuum pump. Significantly, however, this pressure is reduced by head losses in the tubing connecting the vacuum pump to the catheter's proximal end. Accordingly, conventional catheters must be fished out of the vasculature entirely because the thrombus is corked within the distal opening of the vacuum channel.

This disadvantage is removed by the controller 10. After the distal opening of the vacuum channel 3 is occluded by the thrombus, the fluid velocity within the catheter is substantially zero. The controller 10 is used to unclog the vacuum channel 3 and displace the thrombus 4 distally out from the distal opening. Then, the controller 10 re-applies vacuum. Upon re-application of vacuum, the fluid column accelerates and the thrombus 4 accelerates back into the vacuum channel 3. With such acceleration, the thrombus is deformed to a diameter allowing it to be aspirated. With one or just a few applications to displace the thrombus by the shift distance 70 with the controller 10, the vacuum channel 3 becomes unclogged and the thrombus 4 accelerates sufficiently to be completely aspirated through and out of the vacuum tube 2. With the controller 10, the head losses in the tubing are minimized, thereby allowing the thrombus to accelerate to a much greater extent than in conventional product architectures.

Figure 16:
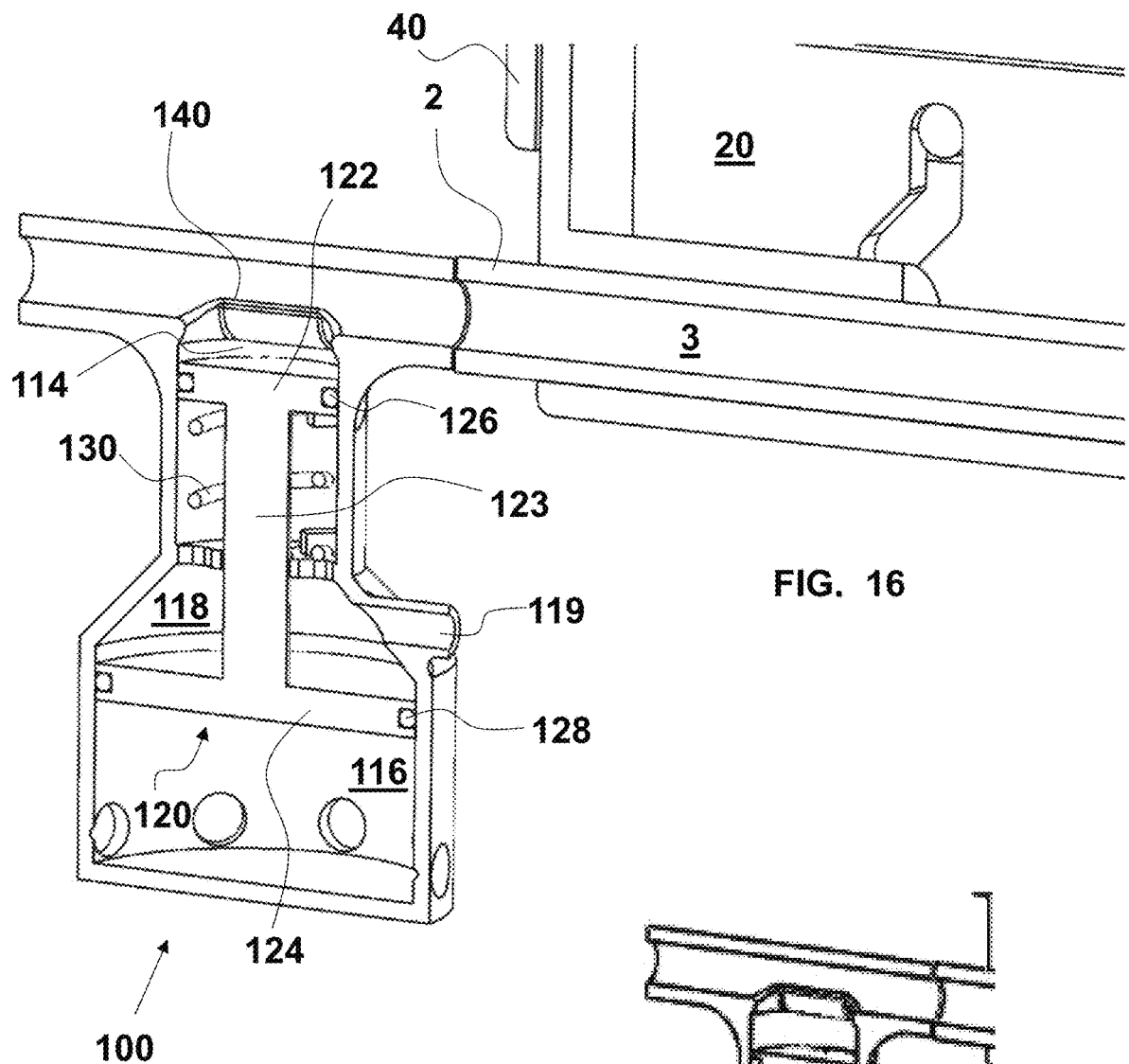
FIG. 16 is a fragmentary, enlarged, perspective and longitudinal cross-sectional view of a distal portion of the controller of FIG. 1 and an exemplary embodiment of a vacuum booster disposed between the controller and a distal extent of the aspiration catheter with the vacuum booster in an energized state.

Realizing that acceleration of the thrombus proximally is a desirable trait, it becomes possible to enhance acceleration in the proximal direction when deactuation of the controller 10 occurs to re-establish vacuum. To maximize the acceleration of the thrombus and the fluid column within the vacuum channel 3 for the purpose of maximizing the thrombus' kinetic energy upon its impact with the distal tip of the vacuum tube 2, a vacuum booster 100, illustrated in FIG. 16, is fluidically connected to the vacuum channel 3 of the vacuum tube 2. In general, the vacuum booster 100 applies suction to the fluid column in a region of the aspiration catheter's proximal end to maximize acceleration of the catheter's fluid column at a user-selected time. This exemplary embodiment of the vacuum booster 100 comprises a booster body 110 defining a plunger bore 112, a plunger 120 housed within the bore 112, and a bias device 130. The plunger bore 112 is shaped to define a vacuum chamber 114 and an ambient chamber 116. In the exemplary embodiment, the vacuum chamber 114 is cylindrical and has a first inner diameter and the ambient chamber 116 is cylindrical and has a second inner diameter larger than the first inner diameter. The vacuum chamber 114 has a volume that is smaller than a volume of the ambient chamber 116.

Figure 23:
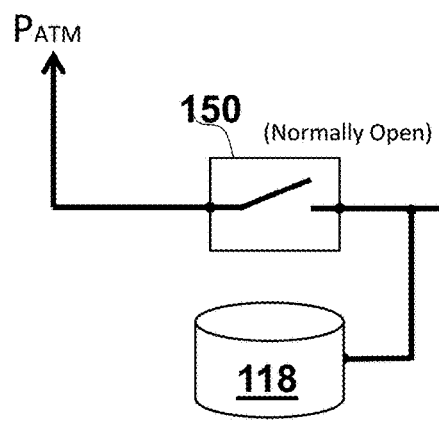
FIG. 23 is a vacuum circuit diagram of an exemplary embodiment of a vacuum booster and vacuum booster control device.

The plunger 120 has a vacuum piston 122 and an ambient piston 124, which is connected to the vacuum piston 122 through a rod 123. In the exemplary embodiment, the vacuum piston 122 has a diameter substantially equal to the first inner diameter of the vacuum chamber 114 and is able to move within the vacuum chamber 114. The ambient piston 124 has a diameter substantially equal to the second inner diameter of the ambient chamber 116 and is able to move within the ambient chamber 116. Between the vacuum piston 122 and the ambient piston 124 is a pressure chamber 118 in which is located the rod 123 connecting the two pistons 122, 124 together, for example, in the shape of an asymmetric dumbbell. To seal the pressure chamber 118 off from both the vacuum chamber 114 and the ambient chamber 116, a vacuum seal 126 is disposed between the vacuum piston 112 and the wall of the vacuum chamber 114 and an ambient seal 128 is disposed between the ambient piston 124 and the wall of the ambient chamber 116. The booster body 110 defines the pressure chamber 118 and a pressure port 119 that fluidically connects the pressure chamber 118 to a boost control valve or switch 150. This connection is illustrated diagrammatically in FIG. 23.

Figure 17:
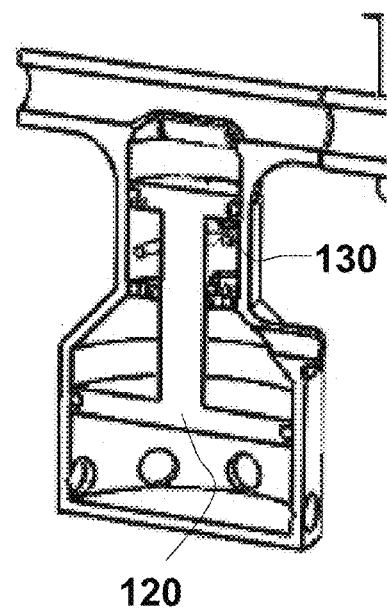
FIG. 17 is a fragmentary, enlarged, perspective and longitudinal cross-sectional view of the controller and the vacuum booster of FIG. 16 with the vacuum booster in a relaxed state.
Figure 18:
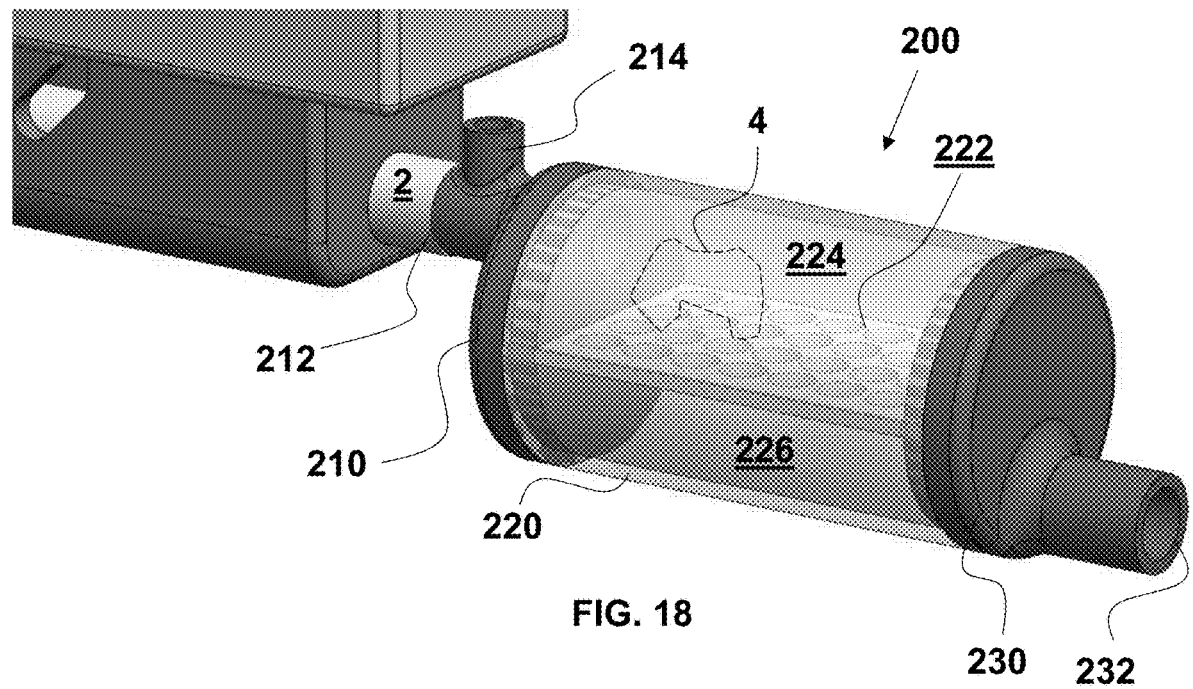
FIG. 18 is a fragmentary, enlarged, perspective and partially transparent view of a proximal portion of the controller of FIG. 1 and an exemplary embodiment of a thrombus trap.
Figure 19:
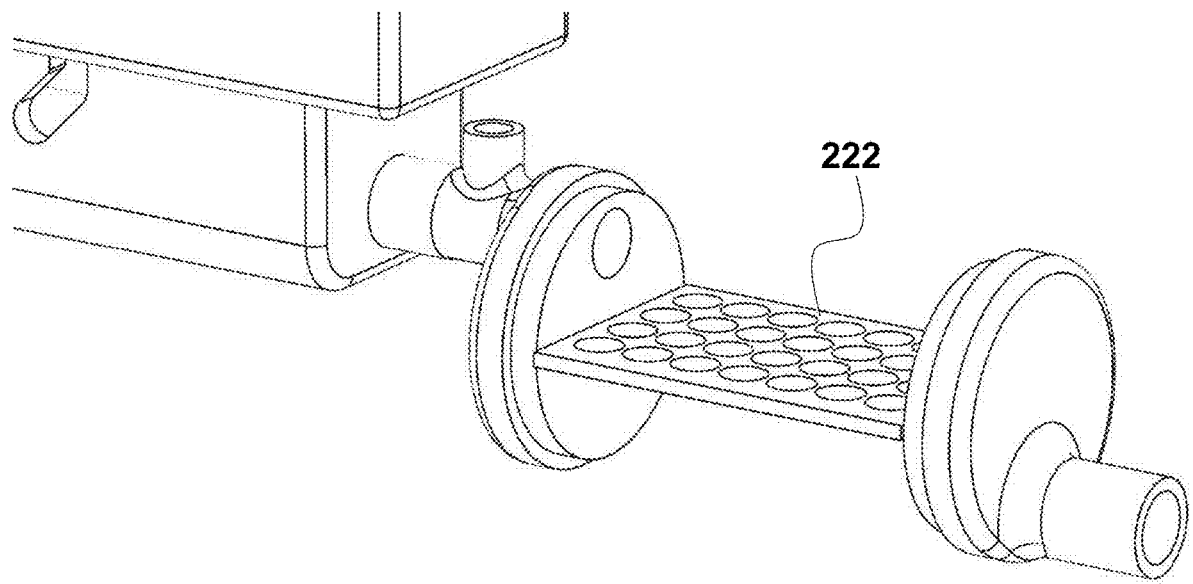
FIG. 19 is a fragmentary, enlarged, perspective view of the controller and thrombus trap of FIG. 18 with the intermediate shell of the thrombus trap removed.
Figure 20:
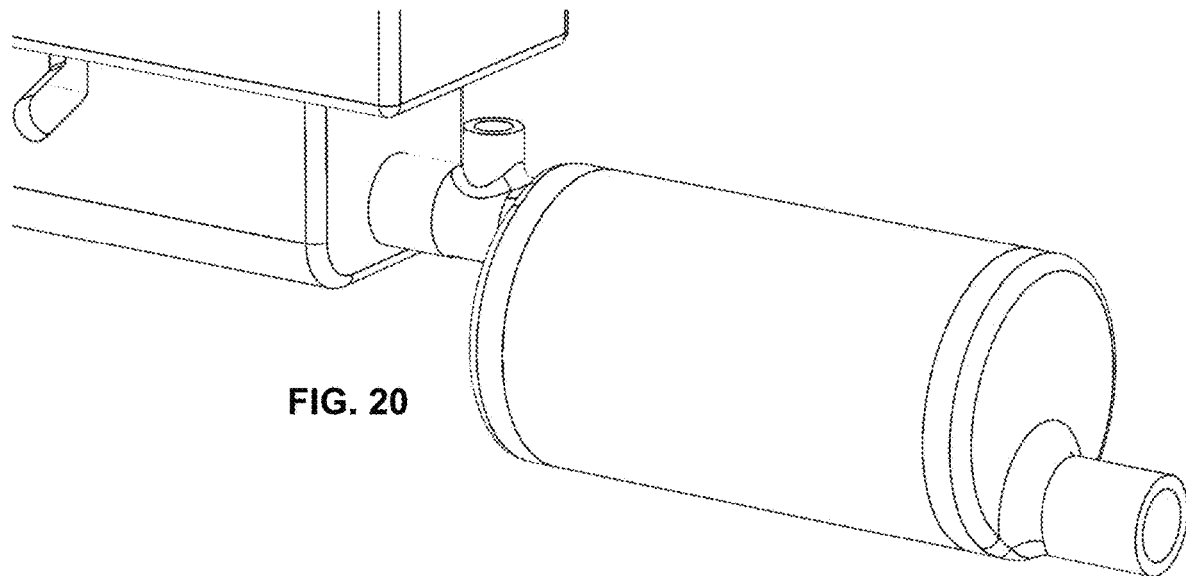
FIG. 20 is a fragmentary, enlarged, perspective view of the controller and thrombus trap of FIG. 18.

The vacuum chamber 114 operatively communicates with the vacuum channel 3 at a connection 140. The plunger 120 and the bias device 130 are disposed such that, when the bias device 130 is in a relaxed state, the vacuum piston 122 is at a given distance from the connection 140 to the vacuum channel 3; this relaxed state is illustrated in FIG. 17. In the relaxed state, the spring is at a steady state—there is no potential energy stored in the spring. With regard to pressure, in the relaxed state, both the pressure chamber 118 and the ambient chamber 116 are at ambient pressure, i.e., they are substantially equal. When the plunger 120 is moved towards the vacuum channel 3 into an energized state (which is shown in FIG. 16), the bias device 130 (e.g., in the form of a spring that is stretched) thereby stores strain energy that is directed to move the plunger 120 away from the connection 140. Such movement, when it occurs, creates suction within the vacuum chamber 114 and the vacuum channel 3 that communicates with the vacuum chamber 114.

To actuate the embodiment of the pneumatically actuated vacuum booster 100, the pressure chamber 118 is connected to the vacuum pump 80 (the vacuum source) through a relatively high impedance conduit 152. The pressure chamber 118 is also connected to the boost control valve 150, which is connected to ambient pressure but is normally open to prevent flow from the pressure chamber 118 to the environment (Patm). When the vacuum booster 100 is in a cocked state (FIG. 16), the boost control valve 150 is open (as shown) and, as such, the vacuum pump 80 is able to significantly lower pressure within the pressure chamber 118. When the boost control valve 150 is actuated (i.e., connecting the pressure chamber 118 to the ambient environment), pressure equalization occurs between the pressure chamber 118 and the ambient chamber 116. An impedance of a connection between the pressure chamber 118 and the boost control valve 150 is designed to be substantially less than the impedance between the pressure chamber 118 and the vacuum pump 80 such that, upon actuation of the boost control valve 150 (i.e., closure), rapid pressure equalization is possible.

Operation of the vacuum booster 100 is explained with regard to the system cycle diagram of FIG. 24.

State 1: Normal aspiration is occurring. The vacuum channel 3 is not occluded. The controller 100 is in a rest state where the vacuum pump 80 is connected to the vacuum channel 3. The vacuum booster 100 is in the cocked state. The thrombus trap 200 is operating without bleed purge.

Transition A—Occlusion: Thrombus 4 occludes distal end of vacuum channel 3. Unclogging controller 10 actuates to occlude vacuum channel 3 and stop vacuum flow distal of the controller 10.

State 2: Flow through the vacuum channel 3 has stopped.

Transition B—Unclogging: Controller 10 continues actuation to cause reverse flow in vacuum channel 3 for a metered volumetric column shift.

State 3: Flow reversal stops.

Transition C—Vacuum Boost: Vacuum booster 100 actuated to re-initiate flow in nominal direction and accelerate thrombus 4 into catheter tip. Shortly before, at the same time, or shortly thereafter, controller 10 opens vacuum channel 3 to reinitiate vacuum of pump 80 for fluid flow and aspiration of thrombus 4 into thrombus trap 200. Simultaneously or thereafter, controlled purging or automatic purging of thrombus trap 200 occurs allowing inspection of thrombus 4.

Return to State 1 and Repeat: Vacuum booster 100 and self-purging trap 200 are de-actuated. Normal aspiration occurs.

During the occlusion and column shift phases in the operation of the controller 10, the plunger 120 is held in the energized state, with the plunger 120 raised to place the vacuum piston 122 closer to the connection 140. During or immediately upon the end of the reversal phase, the plunger 120 is released, generating suction within the locally communicating lumen of the vacuum channel 3 and thereby accelerating the fluid column proximally in the vacuum direction. What fluid is begin drawn into or towards the vacuum chamber has an effect on the efficiency of the vacuum booster 100. More specifically, if the fluid arrives only from downstream of the vacuum booster 100 when actuated, then the fluid column will not accelerate proximally as desired. When the controller 10 occludes the vacuum channel 3, fluid into and towards the vacuum chamber 114 will arrive substantially from upstream of the vacuum channel 3, thereby accelerating the fluid column in the desired direction. In an intermediate stage where fluid arrives from both upstream and downstream, the downstream portion can be limited, for example, by placing a non-illustrated check valve between the thrombus trap 200 and the connection 140, in particular, between the connection 140 and the controller 10. The check valve can be external or can use the occlusive function of unclogging handle.

The following description summarizes the forces in a pneumatic embodiment of the vacuum booster 100. In an un-cocked state of the plunger 120, the pressure chamber 118 and the ambient chamber 116 are at ambient pressure and the bias device 130 is in substantially in the relaxed state, storing little or no strain energy. In a cocked state of the plunger 120, the pressure chamber 118 is caused by the boost control valve 118 to be at a significantly lower pressure than the ambient chamber 116. The geometries of the chambers 114, 116, 118 and the pistons 122, 124, and the characteristics of the bias device 130 are selected such that, in this configuration, a force created by the pressure difference across the ambient (larger) piston is significantly greater than the force required to expand the spring. As such, when the given pressures are held, the piston and spring system translates upwards into a "cocked" position. When the vacuum booster 100 is actuated, the pressure chamber 118 is allowed to rapidly equalize to ambient pressure. With no net force input from the ambient piston 124 (the larger of the two pistons), any motion of the piston and spring system are now caused by the actions of the bias device 130 and the pressure differential across the smaller, vacuum piston 122. The geometries of the chambers 114, 116, 118 and the pistons 122, 124, and the characteristics of the bias device 130 are selected such that the bias device's restoring force in the cocked configuration is much higher than an opposing force caused by the pressure difference across the smaller vacuum piston 122, which is disposed between ambient pressure and a pressure within the vacuum channel 3. As such, when the vacuum booster 100 is actuated and the pressure chamber 118 is allowed to equalize to ambient pressure, the piston and spring system energetically drives "downwards", generating a negative displacement and a dramatic pressure decrease within the vacuum chamber 114 and thereby the vacuum channel 3 of the aspiration device.

As indicated herein, current thrombus removal devices are not able to inform the surgeon that the thrombus has been removed without full withdrawal of the device from a patient's anatomy. Surgeons do not have an ability to view the reservoirs into which aspirated contents are deposited, not only because the reservoirs are located outside of the sterile field in an operating room setting, but also because the removed thrombus is present within a significant quantity of blood contained in the reservoir.

To overcome an inability to visualize the thrombus actually retrieved, a visualization-aiding thrombus trap 200 is provided and shown in FIGS. 18 to 21. The thrombus trap 200 is placed in-line with the aspiration system, in particular, the vacuum channel 3. In the exemplary embodiment, the thrombus trap 200 is within the catheter operator's immediate vicinity between the aspiration catheter and the vacuum source, in particular, between the controller 10 and the vacuum pump 80, so that the surgeon can see the thrombus trap 200 during use of the controller 10. In use, all aspirated material flows through the thrombus trap 200.

The thrombus trap 200 comprises a container having an inflow section 210 having an input orifice 212 fluidically connected to the vacuum channel 3, a transparent intermediate trap section 220 in which the thrombus is trapped, and an outflow section 230 fluidically connected to the vacuum pump 80. In operation, aspirated material and fluid travel from the vacuum channel 3 past the controller 10 through the inflow section 210 and into the trap section 220. The trap section 220 contains a trap filter 222 that is, in an exemplary embodiment, a screen or a filter through which all aspirated flow must pass. The filter 222 is configured to stop and capture thrombus material therein but allow the passage of air and fluid with minimal impedance therethrough and, thereby out of the outflow section 230 to the vacuum pump 80 and any associated vacuum pump reservoir 82. In the exemplary embodiment of FIGS. 18 to 22, the filter 222 is in the form of a grating or screen having orifices sufficiently large enough for fluid and air to pass therethrough but sufficiently small enough to substantially prevent the thrombus from passing across the filter 222 from an inflow or trap chamber 224 of the trap section 220 to an outflow chamber 226 of the trap section 220. As used herein, the term "filter" includes any structure that is able to separate fluid from particulate matter by allowing the fluid to pass through the structure while preventing the particular matter from passing through. Other exemplary embodiments of the filter 222 include perforated polymer, textile, or sintered semi-permeable polymer. The outflow section 230 has an output orifice 232 that fluidically connects the outflow chamber 226 to the vacuum pump 80 for directly receiving the vacuum generated.

The container of the thrombus trap 200 is sealed when closed and in use during a surgical procedure. In an exemplary embodiment, the thrombus trap 200 can be taken apart and opened for removal of the thrombus out of the trap chamber 224 and inspection by the surgeon or pathologist, as well as for sterilization when the thrombus trap 200 is reusable.

It is noted that when a thrombus 4 is captured in the trap chamber 224, whether or not vacuum is still being applied, the trap chamber 224 is also filled with blood. Thus, the thrombus 4 cannot be visualized even if the entirety of the thrombus trap 200 is transparent for viewing inside by a user. To assist with visualization of the thrombus 4 contained within the trap chamber 224, the thrombus trap 200 is configured to temporarily purge itself of fluids that visually impede inspection of captured thrombus material. In an exemplary embodiment, therefore, the inflow section 212 is formed with an intake bleed valve 214 fluidically connected to the vacuum channel 3 and to the trap chamber 224. The bleed valve 214 is configured to operate in a closed mode, in which any flow of air and/or fluid through the bleed valve 214 and into the trap chamber 224 (or vacuum channel 3) is fully restricted, and a bleed mode, in which the bleed valve 214 intakes a fluid, in particular, ambient air. (Alternatively, if desired, in the bleed mode, the bleed valve 214 can intake a clear liquid such as saline.) During the closed mode operation, the exit of the bleed valve 214 is closed and aspirated materials are unhindered to flow through the thrombus trap 200 from the input orifice 212 and out the output orifice 232 away towards the vacuum source, leaving aspirated thrombus and other solid matter in the trap chamber 224. Accordingly, when the surgeon has captured a thrombus 4 in the trap chamber 224 during a thrombectomy procedure, the surgeon can immediately visualize that thrombus 4 by setting the bleed valve 214 into the bleed mode, which, due to a relatively larger size of the bleed valve's 214 input opening and to a decreased resistance to the vacuum by opening to ambient air, causes the vacuum pump to draw ambient air rapidly into the trap chamber 224 and thereby evacuate all fluid from the trap chamber 224. During inspection, the bleed valve 214 can be configured to occlude the fluidic connection between the trap chamber 224 and the vacuum channel 3. Actuation of the bleed valve 214 can be separate from the controller 10 or mechanically connected to the controller 10 so that, when the controller 10 is in an unactuated state where aspiration is occurring, a bleed switch on the controller can activate the bleed valve 214. The rapid inflow of air into the trap chamber 224 is directed by the descending pressure gradient between the outside environment and the relatively low pressure existing within the volume existing between the trap chamber 224 and the vacuum pump 80. As such, while the bleed 214 valve is open, airflow displaces fluids from the volume of the thrombus trap 200, leaving the volume mostly full of transparent air, instead of opaque blood. This temporary transparency allows for easier inspection of the material caught by the filter 222. The surgeon then can view the thrombus 4 unobstructed within the trap chamber 224. During this examination, the control of the bleed valve 214 (which can be a mechanical or a processor-based controller) can cause the vacuum pump 80 to reduce vacuum or to shut off completely, at least until the surgeon is ready to continue the thrombectomy procedure if continuation is desired. When the bleed valve 214 is set back to the closed mode and re-connection of the trap chamber 224 to the vacuum channel 3 occurs, normal aspiration resumes. Alternatively the bleed valve can be connected to a fluid flush line such as a saline drip bag.

Inspection of the thrombus 4 may be enhanced by providing the thrombus trap 200 with optical filters optimized for visual contrast, transparent trap enclosures as described, built-in magnification or visualization systems, lighting, and/or sensor-based thrombus-detection methods.

Figure 21:
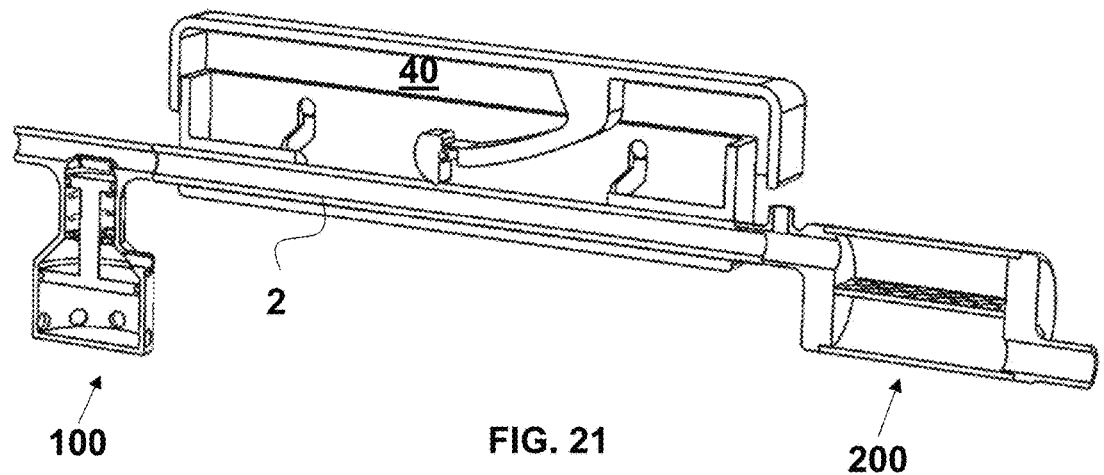
FIG. 21 is a fragmentary, perspective and longitudinal cross-sectional view of the controller of FIG. 16, and the thrombus trap of FIG. 18.

In the exemplary configuration, the vacuum booster 100 is disposed upstream of the thrombus trap 200 and is on a side of controller 10 opposite the thrombus trap 200 as shown in FIG. 21. Accordingly, to maintain efficacy of the thrombus trap 200 as a terminus for all aspirated thrombi 4, vacuum booster configurations that might entrap or significantly damage or macerate the thrombus are less desirable. One exemplary embodiment of a gentler vacuum booster 200, instead of the piston design of FIGS. 16 and 17, couples a section of the tubing of the vacuum tube 2 having a deformable interior volume with a mechanical actuation mechanism. This mechanism is able to collapse and expand the interior cross-section of a length of the vacuum channel 3 to provide an increase or a decrease in pressure along that length. Another mechanical embodiment for the vacuum booster having no pneumatic actuation takes energy for vacuum boost from energy imparted by actuation of the controller 10 or from a separate energy input. For example, as user depresses a lever in the controller 10 that occludes flow and temporarily causes the column shift, the lever's motion also cocks and releases a spring-loaded piston that creates the vacuum boost. Another exemplary embodiment of the vacuum booster places a screen between the vacuum chamber 114 of the vacuum booster 100 and the vacuum channel 3 of the aspiration system. This screen allows fluid communication between the two interior volumes but occludes particulate matter from entering the piston bore defined by the vacuum chamber 114. A further exemplary embodiment that guards against clogging/accidental maceration of the thrombus alters the piston configuration of FIGS. 16 and 17 by having the connection 140 be a flexible diaphragm mechanically disposed between the surface of the vacuum piston 122 and the opening into the vacuum channel 3. The diaphragm can be contained in and cross the actual opening of the vacuum channel 3, for example. Such a membrane transmits volumetric displacement while excluding all flow. The membrane can be separate from the vacuum piston 122, fluidically coupled thereto, or attached. In each of these configurations, the volume through which the fluid column flows is unhindered to prevent entrapping or damaging the thrombus 4 when traveling thereby, whether the vacuum booster 100 is in an energized state or a resting state.

Both the vacuum booster and the blood-purging clot trap rely on the timely and controlled application of either vacuum or ambient pressures to specific parts of the device, namely the bleed valve 214 of the thrombus trap 200 or the plunger 120 of the vacuum booster 100. The self-unclogging thrombectomy aspiration catheter described and shown herein can be provided with additional features actuated by the same user input as the self-unclogging function, e.g., at or by the controller 10, but which serve to either open or occlude additional conduits for vacuum or atmospheric pressure air that control device features such as the self-purging thrombus trap 200 and/or the vacuum booster 100.

The vacuum channel 3 of the vacuum tube 2 (and any other tubing within the catheter) can be coated with a hydrophobic coating, such as carnauba wax, for example, to decrease head loss during aspiration.

With an appropriate pressure sensor (for example, a piezoelectric diaphragm transducer, an electromagnetic diaphragm transducer, a strain-gage diaphragm transducer, or a MEMS pressure integrated circuit transducer), the controller 10 can determine when the vacuum channel 3 is clogged by a thrombus and automatically perform the unclogging procedures described herein. In an exemplary embodiment, a computer connected to the sensor can detect a pressure drop and lack of flow associated with a thrombus clog in or at the vacuum channel 3. When the clog is detected, the sensor triggers the sequence that halts application of vacuum in the vacuum channel 3 and carries out the column shift sequence. With respect to visualization of the thrombus 4 in the device, another exemplary embodiment of a sensor includes an optical sensor that detects the presence of the thrombus in either or both of the distal opening of the vacuum channel 3 and the thrombus trap 200. In the latter configuration, the optical sensor associated with the trap section 220 detects when the thrombus 4 is present and cause purging of fluid by opening the bleed valve 214.

As set forth herein, the vacuum tube 2 can be made from various materials. Some materials for the vacuum tube 2 have a relatively lower compression strength, such as latex, silicone, and other synthetic rubbers. Other materials for the vacuum tube 2 have a relatively higher compression strength, such as Pebax®, polyurethane, and polyvinyl chloride. Because the vacuum tube 2 within the controller 10 is subject to expansion when positively pressured in the vacuum channel 3 and is subject to contraction when negative pressured, this flexible attribute of the material from which the vacuum tube 2 is made could possibly contribute to a less effective column shift. In order to reduce these effects of pressure (both positive and negative) on the vacuum tube 2, the vacuum tube 2 can be reinforced with a braid or coil or other mechanical structure to support the portion of the vacuum tube 2 within the controller 10 against pressure changes. Where the vacuum tube 2 is made from a material with a relatively lower compression strength, the section of the vacuum tube 2 that resides within the controller 10 is made as short as possible to minimize the expansion/contraction effects.

Figure 22:
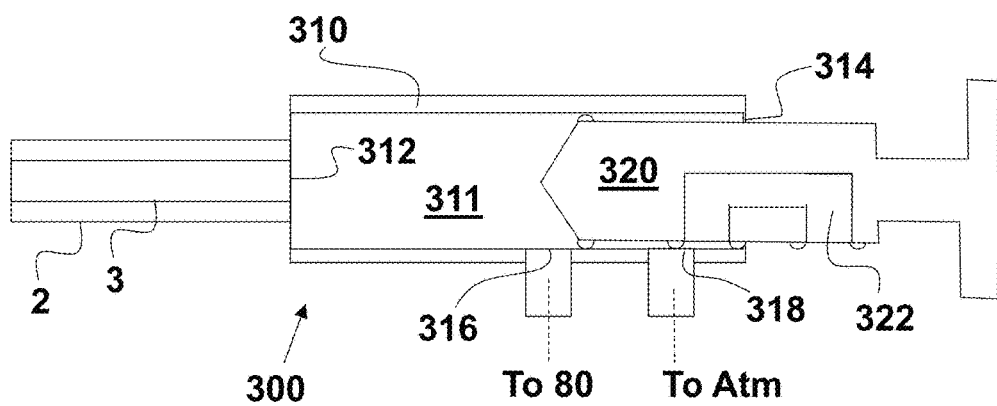
FIG. 22 is a fragmentary, longitudinal cross-sectional view of an exemplary embodiment of a volume changing controller.
Figure 29:
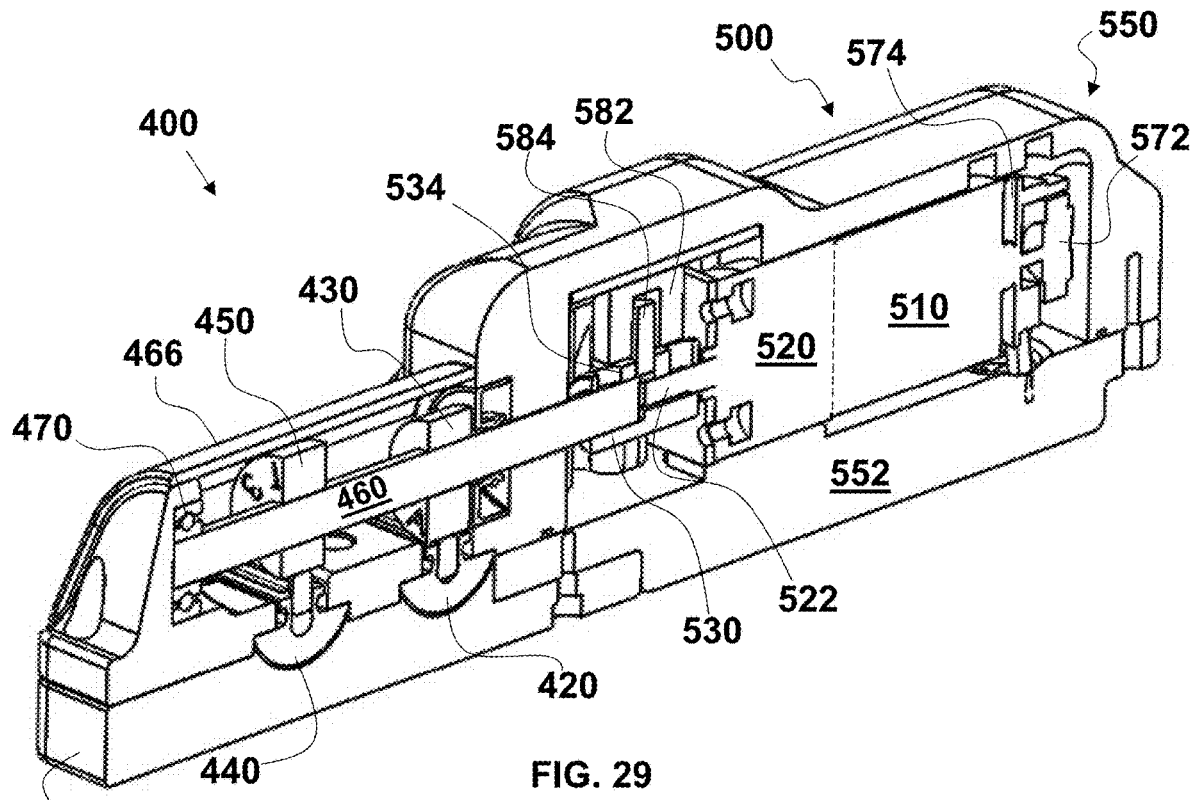
FIG. 29 is a perspective and longitudinally cross-sectional view of the aspiration thrombectomy system of FIG. 25 with a vacuum valve in a closed state, a vent valve in an open state, and a flag of a positional reset assembly in a zero reset state.

An alternative embodiment to the controller 10 of FIG. 1, which indirectly operates on the vacuum channel 3 through the compression roller 60, is shown in FIG. 22. In the exemplary embodiment of FIG. 22, the extrusion compressor is replaced with a volume changing controller 300 that is directly fluidically connected to the vacuum channel 3 of the vacuum tube 3. The volume changing controller 300 has a barrel body 310 with an interior 311 defining an input orifice 312 fluidically connected to the vacuum channel 3. The barrel body 310 also defines a plunger orifice 314, a pump orifice 316, and a purge orifice 318. A plunger 320 sealably connects to the interior 311 of the barrel body 310 movably towards and away from the input orifice 314. When in the position shown in FIG. 22, vacuum applied by the vacuum pump 80 is connected to the distal opening of the vacuum channel 3 for aspiration of material. When a thrombus becomes clogged at the distal opening, the surgeon presses the plunger 320 inwards. In a first portion of the inwards motion, a surface of the plunger 320 seals off the pump orifice 316 to stop the application of vacuum to the vacuum channel 3. In a second portion of the inwards motion, the plunger 320 moves all fluid contained within the interior 311 and the vacuum channel 3 distally to cause the column shift. Reversal of the plunger reverses the column shift and reapplies vacuum to the vacuum channel 3.

The plunger 320 can also be used to control purging of the thrombus trap 200. The plunger is provided with a purge conduit 322. When the plunger 320 is placed in a purge position, the plunger 320 closes off the vacuum channel 3 from the vacuum pump 80 and fluidically connects the pump orifice 316 to the purge orifice 318 through the purge conduit 322. In this position, a fluid connected to the purge orifice, e.g., ambient air, is drawn through the purge conduit 322, through the purge orifice 318, and into the thrombus trap 200.

Operation of the volume changing controller 300 is explained with regard to the system cycle diagram of FIG. 24.

State 1: Normal aspiration is occurring. The vacuum channel 3 is not occluded. The volume changing controller 300 is in a rest state where the vacuum pump 80 is connected to the vacuum channel 3.

Transition A—Occlusion: Thrombus 4 occludes distal end of vacuum channel 3. Controller 300 actuates (plunges) to occlude vacuum channel 3 and stop vacuum flow distal of the controller 300.

State 2: Flow through the vacuum channel 3 has stopped.

Transition B—Unclogging: Controller 300 continues to plunge to cause reverse flow in vacuum channel 3 for a metered volumetric column shift.

State 3: Flow reversal stops.

Transition C—Return Column Shift: Controller 300 is reversed to return column and accelerate thrombus 4 into catheter tip by reconnecting the vacuum pump 80 to the vacuum channel 3.

Return to State 1 and Repeat: Normal aspiration occurs.

FIGS. 25 to 41 illustrate an exemplary embodiment of an aspiration thrombectomy system 400 operating with an automatic, rapid, and repeated onset of pressure change. An aspiration catheter 410 is diagrammatically indicated in FIG. 26 leading from distal orifices of a pair of valves 420, 440, which in this exemplary embodiment are pinch valves 420, 440. One of these valves is a pinch valve 420 to control vacuum flow and is connected between the aspiration catheter 410 and the aspiration pump (e.g., vacuum pump 80). The other of these valves is a pinch valve 440 to control vent flow and is connected to a supply of vent liquid. In an exemplary embodiment, the vent liquid can be any of albumin, d5W water, normal saline, half-normal saline, and lactated Ringer's solution, to name a few. The vent liquid can also be any other biocompatible fluid such as contrast media or tissue plasminogen activator (tPa). With such fluids, the catheter 410 can perform different functions. For example, switching the vent liquid to contrast media after it is believed that a clot has been successfully removed allows the surgeon to inject that media into the vessel to confirm removal of the clot. This is significant because the catheter 410 changes from the aspiration function to the contrast injection function without any significant movement within the vasculature. With standard aspiration catheters where a clot becomes lodged in the distal end, the entire catheter needs to be removed from the patient and, if contrast needs to be injected at the site, the catheter needs to be reintroduced through the vasculature just to perform this visualization. The vent liquid can be at atmospheric pressure or at a higher or lower than atmospheric pressure.

In an exemplary configuration, these valves 420, 440 are mounted to a base 401. Operatively associated with the pinch valves 420, 440 are respective cams, a vacuum cam 430 and a vent cam 450. These cams 430, 450 are connected to a cam shaft 460. A first shaft end 462 of the cam shaft 460 is fixedly connected to a shaft bearing 470 in a freely rotatable manner. The shaft bearing 470 has a bearing body 472 mounted to the base 401. A second shaft end 464 of the cam shaft 460 is connected to a shaft drive assembly 500. The shaft drive assembly 500 comprises a motor 510, a transmission or gear box 520, a shaft coupler 530, and a motor controller assembly 550.

The transmission 520 has an output shaft 522. To connect the transmission 520 to the cam shaft 460, a first coupler end 532 of the shaft coupler 530 is connected to the output shaft 522 and a second coupler end 534 of the shaft coupler 530 is connected to the second shaft end 464. In this manner, rotation of the motor 510 corresponds to a rotation (at the same or different speed based upon the gearing of the transmission 520) of the cam shaft 460 with a corresponding rotation of the vacuum and vent cams 430, 450.

Figure 30:
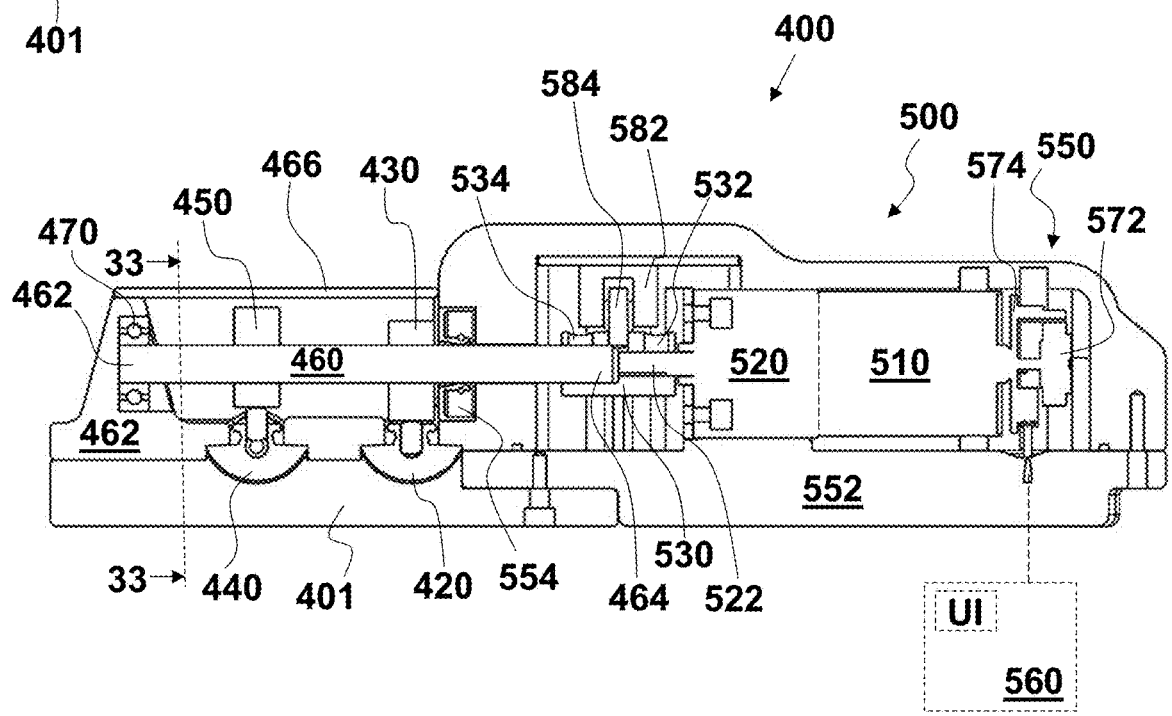
FIG. 30 is a longitudinally cross-sectional view of the aspiration thrombectomy system of FIG. 29.

Control of the motor 510 originates from the motor controller assembly 550, which comprises a controller 560, a positional encoder 570 and a positional reset assembly 580. In an exemplary embodiment, the controller 560 is a microcontroller that has a user interface (UI) comprising user inputs that include, for example, control buttons to operate the aspiration thrombectomy system 400 in various states, examples of which are described in further detail below. The controller 560 with the UI is illustrated diagrammatically in FIG. 30. To isolate parts from fluid, in the exemplary embodiment, the motor 510, the transmission 520, the shaft coupler 530, and the motor controller assembly 550, 560, 570, 580 are contained in a motor assembly housing 552. The connection of the motor assembly housing 552 to the cam shaft 460 is sealed fluidically with a shaft seal 554. Similarly, the cams 430, 450, the cam shaft 460, and the shaft bearing 470 are covered with a cam housing 466. The controller 560 is indicated in FIG. 30 as separate from the motor assembly housing 552 (either wired or wireless) but it can also be integrated into or attached to the motor assembly housing 552. In a wireless configuration, the controller 560 can be an app on a computer or smartphone, for example, with all of the UI being available through a touchscreen.

The vacuum and vent cams 430, 450 are fixed rotationally to the cam shaft 460. These cams 430, 450 have various cam profiles to operate the valves 420, 440. It is desirable to know the exact rotational position of the cams 430, 450 and, therefore, cam shaft 460, so that the controller 560 can set the valves 420, 440 in whatever state that is desired. Because the motor 510 rotates freely and can end its rotation at any rotational position, it is desirable to know the exact rotational position of the cam shaft 560 at all given times. Accordingly, the motor controller assembly 550 includes the positional encoder 570 associated with the motor 510. With this association, the controller is provided with information on the exact rotational state of the cam shaft 460 and, therefore, the cams 430, 450. The positional encoder 570 comprises an encoder disk 572 and an encoder circuit 574. The encoder 570 is able to detect and report out to the controller 560 the current relative rotational position of the motor 510 at any point in time.

Those of skill in the art know that the motor 510 and/or the positional encoder 570 can drift in use. To account for and correct any drift, the motor controller assembly 550 comprises the positional reset assembly 580. This positional reset assembly 580 assigns a single rotational position of the cam shaft 460 as a reset point and every time that position crosses a zero-line the positional encoder resets the position of the motor 510 to zero, which in turn allows the system to know the absolute position of the cam shaft 460. In an exemplary embodiment, the positional reset assembly 580 comprises a photodiode 582 and a flag or interrupter 584. As shown in FIG. 30, the flag 584 is fixed to the shaft coupler 530. The photodiode 582 is placed at the path of the flag 584 so that the flag 584 interrupts the photodiode 582 once for each rotation of the cam shaft 460. This exemplary embodiment allows for immediate correction of any skipped steps of the encoder 570.

Figure 31:
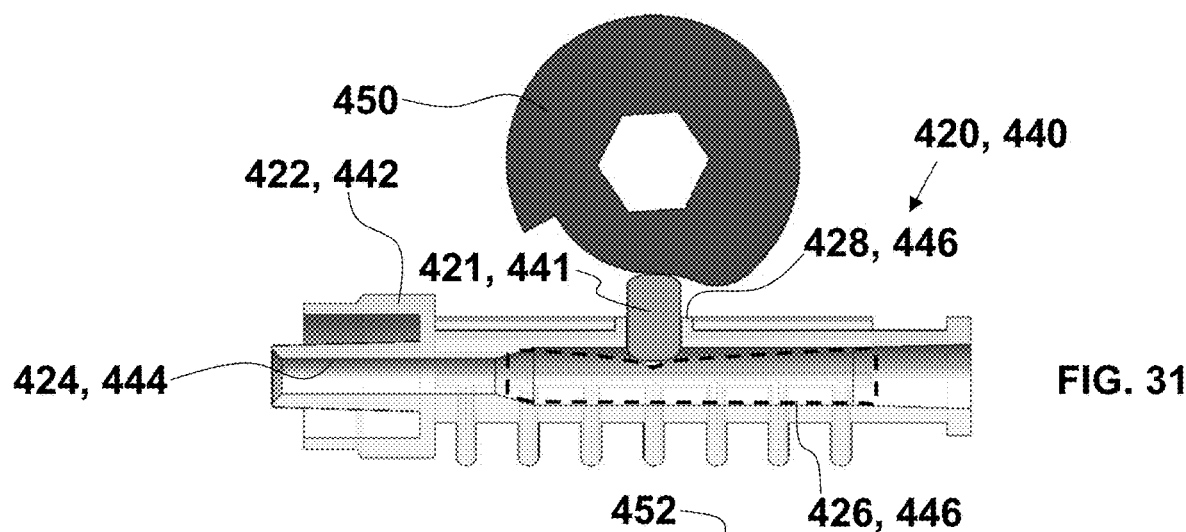
FIG. 31 is an enlarged cross-sectional view of a valve and cam set of the aspiration thrombectomy system of FIG. 25 with the cam in a rotational position to set an intermediate closing of the valve.
Figure 32:
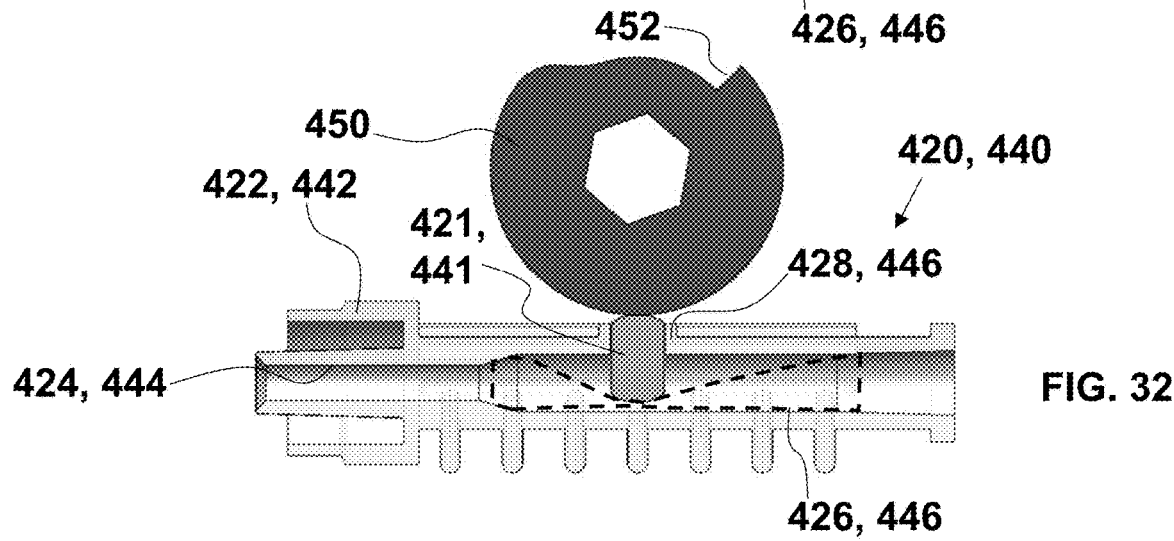
FIG. 32 is an enlarged cross-sectional view of the valve and cam set of FIG. 31 with the cam in a rotational position to close the valve.
Figure 33:
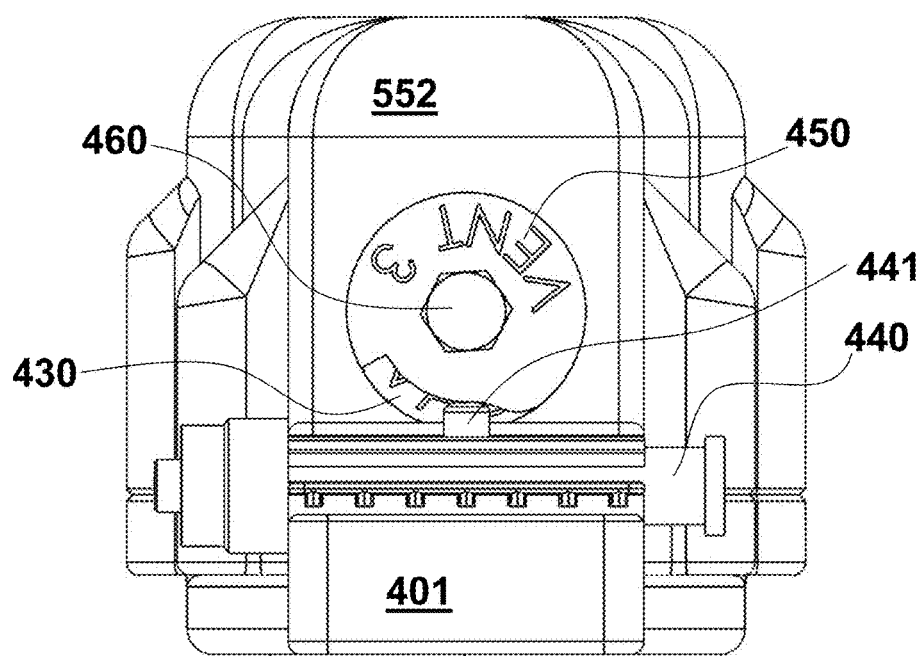
FIG. 33 is a cross-sectional view of the aspiration thrombectomy system of FIG. 25 along section line 33-33 in FIG. 30 with the cam housing removed.
Figure 41:
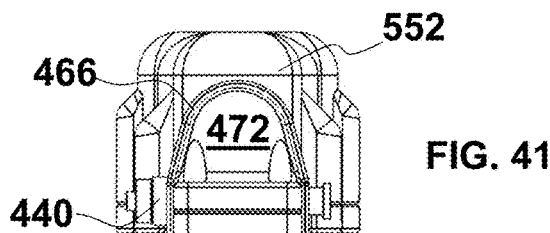
FIG. 41 is an elevational view of the bearing side of the aspiration thrombectomy system of FIG. 28 with the cam housing.
Figure 38:
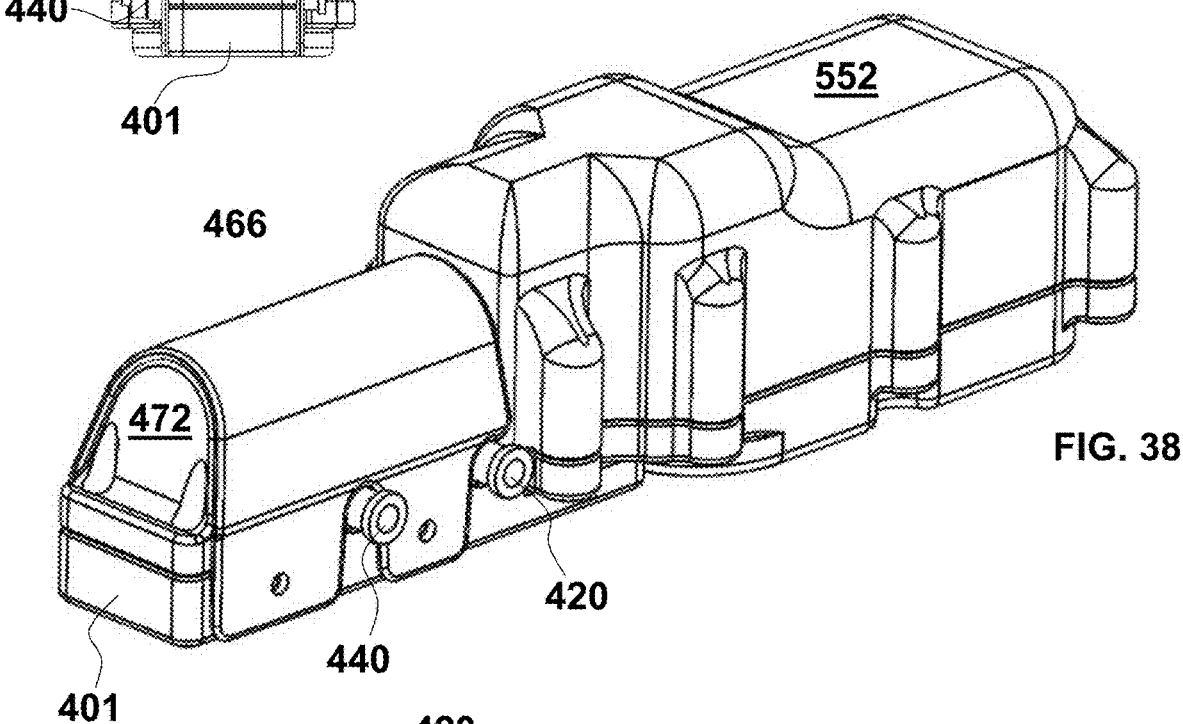
FIG. 38 is a perspective view of the aspiration thrombectomy system of FIG. 25 with the cam housing.
Figure 39:
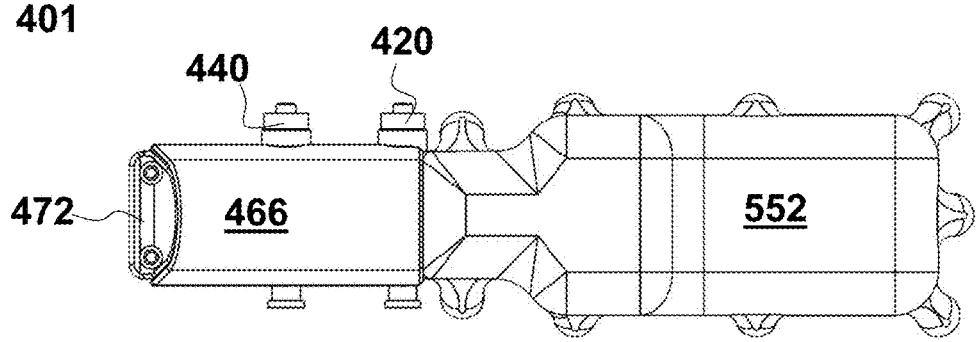
FIG. 39 is a top plan view of the aspiration thrombectomy system of FIG. 26 with the cam housing.
Figure 40:
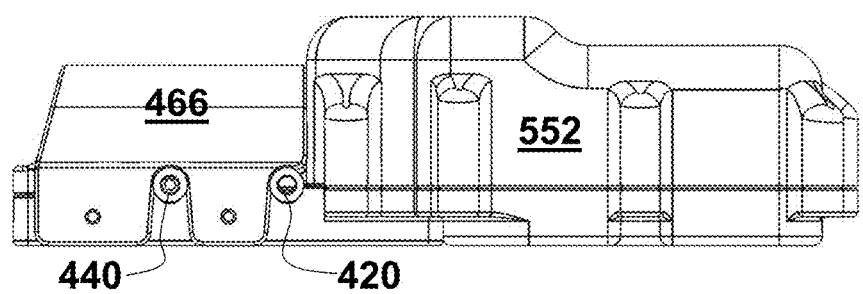
FIG. 40 is an elevational view of the aspiration thrombectomy system of FIG. 27 with the cam housing.
Figure 42:
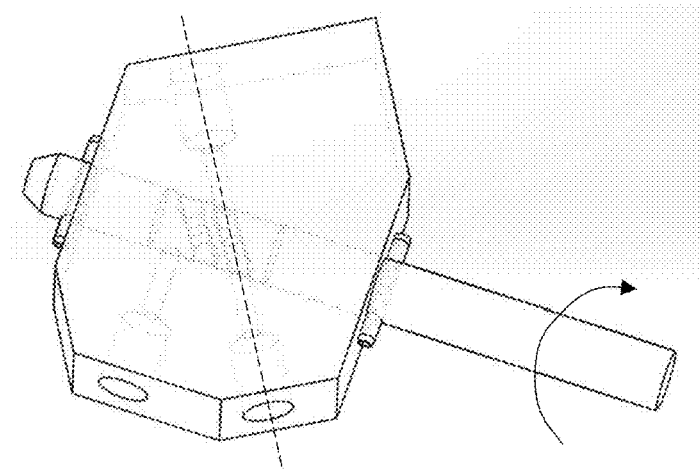
FIG. 42 is a fragmentary, partially hidden, perspective view of an exemplary embodiment of a rotational pintle valve to be employed with the aspiration thrombectomy system in a first valve state.
Figure 43:
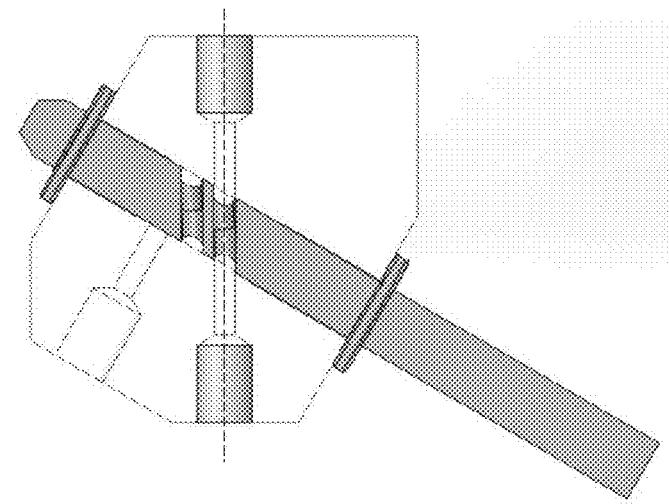
FIG. 43 is a fragmentary, cross-sectional view of the valve of FIG. 42.
Figure 44:
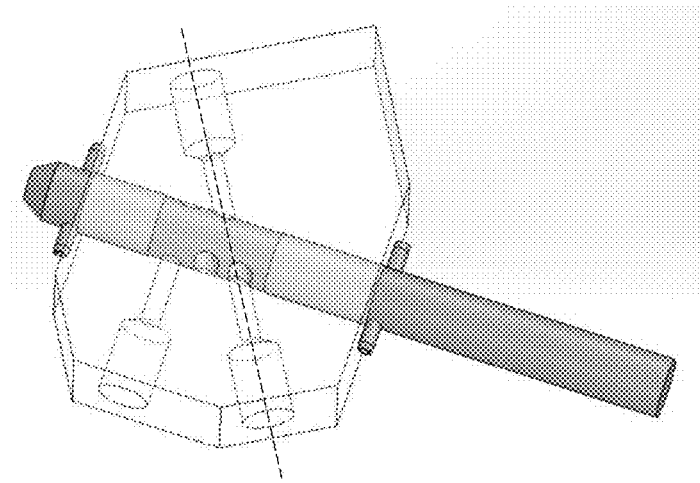
FIG. 44 is a fragmentary, partially hidden, perspective view of the valve of FIG. 42.
Figure 45:
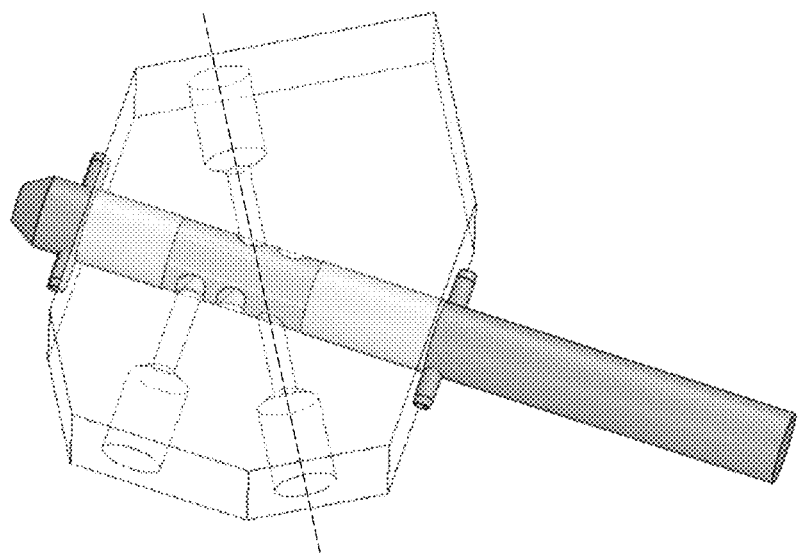
FIG. 45 is a fragmentary, partially hidden, perspective view of the valve of FIG. 42 in a second valve state.
Figure 46:
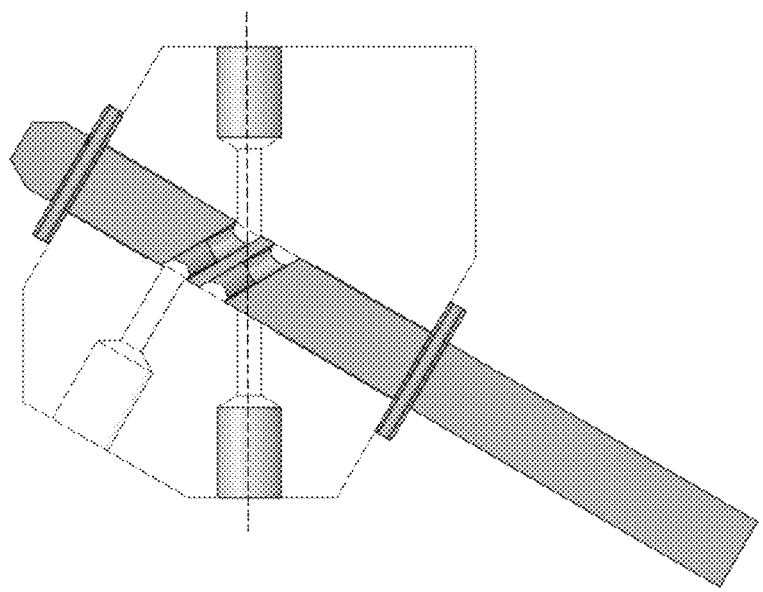
FIG. 46 is a fragmentary, cross-sectional view of the valve of FIG. 45.

The exemplary embodiment of the pinch valves 420, 440 is explained with regard to FIGS. 31 to 33 using the vent pinch valve 440. Each valve 420, 440 comprises a valve body 422, 442 defining a vacuum or vent lumen 424, 444. An elastomeric tube 426, 446 is secured within the lumen 424, 444 at each end of the tube 426, 446. Exemplary embodiments for this connection include but are not limited to fusing, compression sealing, and fixation with an adhesive. Accordingly, the tube 426, 446 spans an extent of the lumen 424, 444 with an intermediate portion of the tube 426, 446 unattached to the lumen 424, 444. A lumen of the tube 426, 446 fluidically connects a distal end of the lumen 424, 444 (to the left of FIGS. 31 and 32) to the proximal end of the lumen 424, 444 (to the right of FIGS. 31 and 32). The intermediate section of the valve body 422, 442 defines a follower connection in which is movably secured a cam follower 421. A first end of the cam follower 421 is biased against the outer surface of the cam 430, 450 with a non-illustrated bias device or is simply trapped in place. The opposing second end of the cam follower 421 rests against the intermediate portion of the tube 426, 446. Accordingly, when moved by the cam 430, 450 towards the tube 426, 446, as shown in FIG. 32, the cam follower 421 fluidically seals off the lumen of the tube 426, 446 and, when allowed to return away from the tube 426, 446, as shown in FIG. 31, the cam follower 421 opens the lumen of the tube 426, 446. In the exemplary embodiment, the cam follower 421 is pill-shaped but it can be formed in any shape to provide the function of closing off the tube 426, 446.

Both a vacuum line 402 and a vent line 404 are connected through the selectively openable valves 420, 440 to a proximal end of the aspiration catheter 410. In operation, the vacuum cam 430 and the vent cam 450 push down on the respective cam followers 421, which pinch down the short sections of tubing 426, 446, each respectively fluidically connected to the vacuum line 402 and the vent line 404. When the vacuum line 402 is open and the vent line 404 is closed, vacuum is drawn on the aspiration catheter 410. When the distal end of the catheter 410 is clogged with a clot, the closure raises a vacuum level within the catheter 410 to full (the greatest current vacuum generated by the vacuum pump). This closure creates a delta in pressure between the internal lumen of the catheter 410 and the environment external to the catheter 410, which change squeezes down the body of the catheter 410 both radially and longitudinally (e.g., the diameter and length become incrementally smaller). This change also draws out a small volume of liquid from within the lumen of the catheter 410. In an exemplary embodiment, the volume is approximately 0.2 ml. The end effect is the creation of a spring-like force within the catheter 410 that wants to expand the catheter 410 back to its steady state, but when the vacuum line 402 is closed off, that cannot happen. Thus, the vacuum is stored as potential energy until the vent line 404 is opened (as can be seen in FIG. 26, for example, the vacuum and vent lines 402, 404 are connected together distal of the valves 420, 440). When the vent line 404 is opened, there is an in-rush of fluid because of the pressure delta. This rush of fluid balances the radial force of the catheter 410 and draws in fluid to create a distally directed momentum in the column of fluid residing in the catheter 410 distal of the valves 420, 440. The momentum causes a small amount of fluid to move through a distal portion of the catheter 410 and create a small distal movement of the clot that is stuck in the distal opening at the end of the catheter 410. Once the clot is no longer stuck at the distal opening, it is able to be moved proximally into and through the catheter 410 with subsequent vacuum imparted to the catheter 410. Repeated selective actuation of vacuum and venting macerates the clot at the distal opening, thereby reforming it into a state where it can be completely drawn into the lumen of the catheter 410 and out of the vasculature. The flow of fluid forward in this exemplary embodiment is intentional, which is in contrast to other exemplary embodiments herein where substantially no forward flow occurs.

The system 400 can be operated in various modes to remove clots in the vasculature. Rotation of the cams are measured in degrees, a full rotation being 360° of movement. In a first exemplary embodiment, the vacuum cam 430 is configured to establish vacuum in the catheter 410 through approximately 220° of rotation. The vent cam 450 is configured to have venting on through approximately 80° of rotation. The configuration of the cams 430, 450 stop both venting and vacuum between each respective application of vacuum and venting, for example, with a 30° rotation. This configuration, therefore results in operation states according to Table 1 below.

TABLE 1

| State | Vacuum | Venting | Cam Angle |
|-------|--------|---------|-----------|
| Off   | 0      | 0       | 0 to +30  |
| Vac   | 1      | 0       | +30 to +250 |
| Off   | 0      | 0       | +250 to +280 |
| Vent  | 0      | 1       | +280 to 0 |

As soon as the vent is opened, there is an in-rush of fluid to balance out the vacuum pressure, then the vent line 404 is closed and the vacuum line 402 is opened, suddenly causing a rapid decrease in pressure that serves to forcefully pull the clot to the catheter. It is desirable, therefore, to close both vacuum and vent lines before resuming vacuum.

In another exemplary embodiment, the vacuum cam 430 is configured to establish vacuum in the catheter 410 through approximately 220° of rotation. The vent cam 450 is configured to have venting on through approximately 80° of rotation. Thus, there is created, in a desirable second exemplary configuration, a pause between vacuum draw in the catheter and venting of the catheter and another pause between venting of the catheter and resuming vacuum draw in the catheter. In this exemplary configuration, the pause can be through approx. 30° of rotation. To create a purge state, where vacuum and venting occur simultaneously, the vent cam 450 has a small inwards depression in a position of the vent cam 450 that occurs during a long vacuum-on stage (e.g., between +30° to +250°). The extent of the venting is configured to not provide a significant change in pressure or change in the vacuum energy but, instead, is configured to create a single rotation position of the cams 430, 450 where the motor control assembly 550 can stop rotation of the cam shaft 460 in that orientation where both the vacuum line 402 and the vent line 404 are connected to the catheter 410, which allows the user to purge out any air that might be present in the system (e.g., in the vacuum line 402, the vent line 404, and/or the catheter 410). The extent of the depression can be such that it only partially opens the vent to reduce the amount of vent liquid that is drawn in during this purge state. This purging can be a known position of the cam rotation and is placed in that position to ensure that all lines in the system 400 are cleared of air. Such a configuration results in operation states according to Table 2 below.

TABLE 2

| State | Vacuum | Venting | Cam Angle |
|-------|--------|---------|-----------|
| Off   | 0      | 0       | 0 to +30  |
| Vac   | 1      | 0       | +30 to +120 |
| Purge | 1      | 1       | +120 to +140 |

TABLE 2-continued

| State | Vacuum | Venting | Cam Angle |
|-------|--------|---------|-----------|
| Vac   | 1      | 0       | +140 to +250 |
| Off   | 0      | 0       | +250 to +280 |
| Vent  | 0      | 1       | +280 to 0 |

A third alternative configuration for operation of the system 400 can include a full-time vacuum with a pulsed venting including the operating states according to Table 3 below.

TABLE 3

| State | Vacuum | Venting | Cam Angle |
|-------|--------|---------|-----------|
| Vac   | 1      | 0       | 0 to +120 |
| Purge | 1      | 1       | +120 to +150 |
| Vac   | 1      | 0       | +150 to 0 |

An opposite configuration to the states of Table 3 can including a full-time venting with a vacuum overlap.

A fourth alternative configuration for operation of the system 400 can include a vacuum during venting, which configuration includes the operating states according to Table 4 below.

TABLE 4

| State | Vacuum | Venting | Cam Angle |
|-------|--------|---------|-----------|
| Purge | 1      | 1       | 0 to +30 |
| Vac   | 1      | 0       | +30 to +250 |
| Off   | 0      | 0       | +250 to +280 |
| Vent  | 0      | 1       | +280 to 0 |

An opposite configuration to the states of Table 3 can include a full-time venting with a vacuum overlap.

A fifth alternative configuration for operation of the system 400 can include a venting during vacuum, which configuration includes the operating states according to Table 5 below.

TABLE 5

| State | Vacuum | Venting | Cam Angle |
|-------|--------|---------|-----------|
| Off   | 0      | 0       | 0 to +30 |
| Vac   | 1      | 0       | +30 to +250 |
| Purge | 1      | 1       | +250 to +280 |
| Vent  | 0      | 1       | +280 to 0 |

In further alternative configurations, there can be a variation overlapping of venting and vacuum, which would delete one or more of the OFF states in any of the state tables above.

The cam-driven valves 420, 440 allow the positional encoder driven motor to create positions for vacuum, venting, off, and purge. The motor controller assembly 550 allows the cams 420, 440 to be controlled by any frequency, e.g., they can be set to move through the various states at any given speed, for example, at 4 Hz. The frequency at which the motor runs may be more appropriate to run at lower frequencies such as 0.5 Hz, 1 Hz, or 2 Hz. Alternatively, it may be more effective to run at higher frequencies such as 8 Hz, 12 Hz, or 16 Hz. The motor control assembly 550 can also dynamically change the rate of cam shaft 460 rotation to sweep the frequency of rotation. In exemplary embodiments, the step in speed is in a range from 1 Hz to approximately 4 Hz, the change in increment is between approximately 0.25 seconds to approximately 5 seconds, and the range of rotation is between approximately 2 Hz to approximately 12 Hz. One example for the step, increment, and range is 2 Hz and 1 second increments in the following progression 2 Hz/4/6/8/10/12/10/8/6/4/2/ . . . . Another example is 4 Hz with 0.5 sec increments in the following progression 4 Hz/8/12/8/4/ . . . . In exemplary embodiments, the system uses the higher frequencies in the 8 Hz to 12 Hz range, which has been observed to have less movement of the proximal end of a clot stuck at the distal end of the catheter 410. Alternatively, further increments can be used to sweep the frequency through complex forms, such as sine, sawtooth, stepped, and pulsing variations.

In an exemplary alternative to the pinch valves 420, 440, the valves can be solenoid-driven pinch valves or voice coil actuators. In another exemplary alternative, a rotational pintle valve can be used, as shown in FIGS. 42 to 46. The first valve state shown in FIGS. 42 to 44 can, for example, be a vacuum-on/vent-off state and the second valve state shown in FIGS. 45 and 46 can be a vacuum-off/vent-on state.

It has been determined that the most rapid onset of vacuum and venting is desirable. To create this rapid onset, the cams 430, 450 start vacuum and venting, respectively, with a cliff 452 in the shape of the cam 430, 450. Sudden creation of vacuum creates a rapid decrease of pressure inside the catheter 410, which draws the clot aggressively against the distal end of the catheter 410. Venting, as described above, creates a distal momentum that unsticks the clot and repetition of the vacuum and venting causes mechanical maceration of the clot at the distal opening until the clot completely enters the lumen of the catheter 410 and is removed from the vasculature. Therefore, the instant system 400 can be described as a Rapid Onset Aspiration Repeater or ROAR.

The control carried out by the motor controller assembly 550 has a selection of user-actuated buttons. In an exemplary embodiment, one button causes both vacuum and venting to be shut off, i.e., off operation. One button causes vacuum to occur in a continuous manner, i.e., manual control. One button causes venting to occur in a continuous manner, i.e., manual control. One button causes the cam shaft 460 to rotate the cams 430, 450 to the position in which the vacuum and vent lines 402, 404 can be purged, i.e., the purge function. One button causes the system to run or pulse repeatedly according to a desired set of states (e.g., according to any of Tables 1 to 5) along with a selection of any number of sets for step, increment, and range. As such, if the surgeon desires to use the system 400 as a simple thrombectomy device, the surgeon can just use the vacuum button. In this condition, the encoder 570 assists to have the cam shaft 460 to rotate to a position in which vacuum is open. The vacuum pump runs with a fully open vacuum until the surgeon releases the button. If the surgeon wants to purge or inject contrast, for example, then the surgeon can use the vent button to have the encoder 570 assist to rotate the cam shaft 460 to a position in which the vent is open. Likewise, the off button rotates the cam shaft 460 to a position where the cams 430, 450 close both the vacuum and vent lines 402, 404. The purge button causes rotation of the cam shaft 460 to a position where the cams 430, 450 allow simultaneous vacuum and venting.

In an exemplary embodiment of the run or ROAR mode, rotation of the cam shaft 460 is between approximately 0.5 Hz and approximately 25 Hz, further, approximately 6 Hz and approximately 16 Hz, in particular, between approximately 8 Hz and approximately 12 Hz. In this exemplary ROAR cycle, the cam shaft 460 is rotated for between approximately 10 seconds and approximately 30 seconds and, during that time, the motor controller assembly 550 causes the motor 410 to sweep through frequencies between approximately 2 Hz and approximately 12 Hz.

As set forth above, the elastomeric tube 426, 446 is attached to distal and proximal locations of the valve lumen 424, 444. Compliance in the system 400 distal of the vacuum valve (described above as including reduction of the diameter and/or length of the catheter 410 as well as compliance of the tube 426, 446) when vacuum is applied to the catheter 410 and a clot is stuck at the distal end determines how much fluid is drawn out when the system 400 is under full vacuum and, conversely, how much fluid rushes back into the system 400 when that state is released. In other words, with a greater amount of compliance distal of the valves 420, 440, momentum imparted to the stuck clot by the column of fluid increases. It is desirable to have a minimal amount of momentum transfer from the fluid column to the stuck clot to unstick the clot sufficiently so that the next vacuum cycle macerates the clot against the distal end of the catheter 410 and causes it to enter the lumen of the catheter 410 and be removed from the vessel. To minimize this compliance (which is fixed for a given catheter 410), this tube 426, 446 is made as short as possible to still allow valve operation by the cam follower. Compliance as used herein refers to mechanical compliance of the catheter 410 and the tube 426, 446; it does not refer to any air that might be in the system 400, which air is purged before use as set forth herein. This desire for a reduction in compliance is one reason the valving system is connected directly to the proximal end of the catheter 410. This close connection minimizes overall compliance. In an exemplary embodiment, the valving system can be located away from the catheter 410 and, in such a case, substantially non-compliant tubing is desired. This configuration may experience lower performance due to the excess compliance.

To determine the status of a clot at the distal end of the catheter 410, the system 400 is put in the ROAR mode. If there are no sensors associated with the system 400, a surgeon cannot distinguish the situation when a clot is corked during ROAR or not. The surgeon has to turn off ROAR and visualize whether the catheter is corked (in which nothing is being drawn in by the catheter 410) or is not corked (in which blood is being drawn into the catheter 410). With the different situations of aborting pulse based on flow and pulsing until not corked, it is hard to know when a clot is corked.

The vent line 404 is connected to a vent liquid reservoir (not illustrated), which can contain for example, any of albumin, d5 water, normal saline, half-normal saline, and lactated ringers. When a fluid is used to vent the system 400, as described above, all air can be purged out of the system 400. Additionally, knowing that a given amount of vent liquid is used at various stages of clot removal can allow the user to correlate removal of a clot into the catheter after being stuck at the distal end to a rate of vent liquid use. In other words, the amount of vent liquid is different when the clot corked from when it is not corked. Thus, a user or a sensor can look at or measure vent liquid use to determine to turn off the system. If the catheter 410 is aspirating without obstruction (uncorked), then a significant flow of blood will exit the system 400. If the catheter 410 is aspirating while corked, then no blood will appear at the vacuum exit. During a ROAR operation and the catheter 410 is uncorked, the user/sensor will detect some blood at the vacuum exit. Finally, during the ROAR operation when the catheter 410 is corked, the vacuum exit will receive some fluid that is a combination of both blood and vent liquid and, in this state, the flow rate of the vent liquid can indicate if the catheter is corked or uncorked.

If a surgeon visualizes free flow during vacuum and see a captured clot (for example, in the thrombus trap 200), then the surgeon has the ability to perform a contrast injection with the catheter 410 to confirm revascularization without moving or removing the aspiration catheter 410. This is in contrast to current state-of-the-art aspiration catheters where the catheter removes the clot by holding the clot corked on the end and the surgeon retracts the entire catheter to drag out the corked clot. The increased ability of a smaller diameter catheter to be able to fully ingest or secure a better grip on the clot by drawing a greater amount of it into the catheter is a significant benefit. Many clots are deep enough into the anatomy that it is difficult to get large catheters to the site of the clot. If a smaller diameter catheter can have increased effectiveness through ROAR than a greater number of clots can be accessed and retrieved.

It is noted that one desirable goal to achieve with the system 400 is to fully ingest a clot and bring it back a standard aspiration canister (in a typical thrombectomy end reservoir) or into the thrombus trap 200. When using a standard aspiration canister and the thrombus trap 200, the system 400 can use the vent liquid to flush the thrombus trap 200 through the intake bleed valve 214 instead of using air. This allows retention of vacuum pressure in the aspiration canister.

Figure 47:
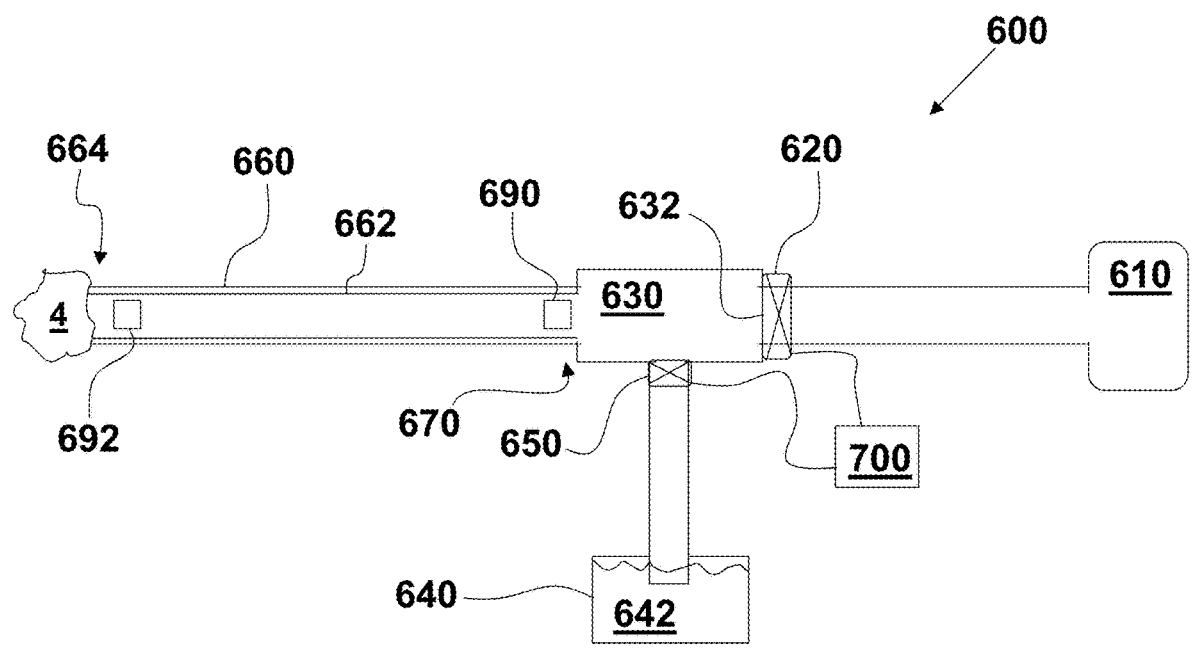
FIG. 47 is a diagrammatic, cross-sectional view of an exemplary embodiment of an aspiration thrombectomy system.

Turning now to embodiments that create maceration but without the forward flow, FIG. 47 illustrates diagrammatically an exemplary embodiment of an aspiration thrombectomy system 600 that operates in a ROAR mode. The system 600 comprises a vacuum source 610 fluidically connected to an input of a controllable vacuum valve 620. (Parts of the vacuum source 610, such as the collection canister, are not illustrated in FIG. 47 for reasons of clarity but are detailed below.) The vacuum valve 620 is fluidically connected to a vacuum input 632 of a manifold 630. The connection can be direct or through a conduit, such as silicone tubing. A vent fluid source or reservoir 640 containing a vent liquid 642 is fluidically connected to a controllable vent valve 650. The vent liquid 642 can be, for example, any of albumin, d5 water, normal saline, half-normal saline, and lactated ringers, to name a few. As used herein, "controllable" means that the device is able to be selected between various states, the selection including analog and/or digital switching. One exemplary embodiment is a digital switching between an open position and a closed with a single command (e.g., a change of bit 1/0). The entire working channel of the aspiration thrombectomy system 600 is to be free from air or other gaseous bubbles during use.

The vent fluid source 640 has a sufficient amount of vent liquid in the reservoir that will not end during a given surgical procedure and this prevents any possibility of air entering the system. If the vent fluid source 640 is flexible, such as with fluid supplied by a parenteral fluid containment bag or an intravenous therapy bag, the gas-free container will shrink as the vent liquid 642 is used. If the vent fluid source 640 is inflexible and has an air or gas pocket, as in a replaceable/removable and sterilizable container, the conduit that transfers the vent liquid 642 from the vent fluid source 640 to the vent valve 650 is at a level within the reservoir to keep the input of that conduit submerged within the vent liquid 642 throughout a given procedure.

A ROAR catheter 660 defines a working lumen 662 fluidically connecting a distal end 664 thereof to a proximal manifold connector assembly 670 at a proximal end of the ROAR catheter 660, which assembly 670 is described in greater detail below. The ROAR catheter 660 is configured to operate in relatively small vessels. Thus, in an exemplary embodiment, the lumen has an internal diameter of between approximately 0.038" and approximately 0.106" and, in particular, an internal diameter of between approximately 0.068" and approximately 0.088". The proximal manifold connector assembly 670 fluidically connects the lumen 662 to the interior of the manifold 630 and, thereby, the manifold 630 fluidically connects the lumen 662 to the vacuum source 610 through the vacuum valve 620 and to the vent fluid source 640 through the vent valve 650. In use within a vessel, the lumen 662 is filled with a liquid column having a proximal portion and a distal portion. Depending on the context used with respect to the catheter 660, the proximal and distal portions of the liquid column can be a given amount (e.g., less than 20 microliters or less than 5 microliters), can be a given length (e.g., a few mm or cm) or it can be an instance of the column that is approximated by using statistical flow analyses. For example, when discussing whether a distal portion of the fluid column exits the distal end of the lumen 662, that distal portion is a measurable distance at the distal end of the liquid column equal to an instance of liquid present at the plane of the lumen distal exit. In the realm of statistical analysis in this example, the distal portion is a last distal finite element in a finite element analysis (FEA) of the liquid column. Here, the system 600 is used to substantially prevent forward flow. The term "forward flow" is used herein to define an amount of liquid in the lumen 662 that exits the distal end 664 in a distal direction. Forward flow is defined as greater than 6 microliters of fluid (approximately 1 mm of catheter length of ID 0.071"=5.7 µL). Less forward flow is also included in this definition. For example, the amount of forward flow can be restricted to no greater than 2 microliters or, in a particularly beneficial embodiment, forward flow is approximately zero microliters. In each case, no forward flow means that substantially no liquid exits the distal end 664 in the distal direction.

Operation of the aspiration thrombectomy system 600 occurs through a controller 700, which can be an analog controller or a digital controller. Examples of the analog controller are shown in FIGS. 25 to 46. An example of a digital controller is described in further detail below. One exemplary configuration for a digital controller is a microcontroller manufactured by Microchip Technology, Inc. The controller 700 is operatively connected to each of the vacuum valve 620 and the vent valve 650 (and to a vacuum motor as described below). The controller 700 selectively opens and closes the vacuum and vent valves 620, 650 such that, when the vacuum valve 620 is opened, the vacuum source 610 is fluidically connected to the liquid column in the lumen 662 and, when the vent valve 650 is opened, vent liquid 642 is fluidically connected to the liquid column in the lumen 662. The timing of these valves is significant so that the controller 700 can change a level of vacuum at the distal end 664 and prevent the distal portion of the liquid column in the lumen 662 from exiting the distal end 664—substantially no forward flow. There are two significant actions that contribute to forward flow when operating the valves 620, 650: compliance of the catheter system and the water hammer effect. Each will be discussed in turn. Exemplary configurations of the vacuum and vent valves is shown in FIGS. 25 to 36 in FIGS. 42 to 46. Configurations for the valves include spool valves, pinch valves, rotary valves, and rotary valve having a pintel design.

To explain timing of the valves to eliminate forward flow, reference is first made to the system depicted in the diagram of FIG. 47. It is noted that the ROAR catheter 660 is a flexible body and, therefore, it has compliance both in the radial direction and in the longitudinal direction. When the distal end 664 is corked with a thrombus (as shown in FIG. 47), vacuum is being applied to the lumen 662. Compliance of the catheter 660, therefore, causes reduction in the diameter of the catheter and reduction in the length of the catheter. When the catheter 660 corked, no flow occurs in the lumen. By having pressure lower than atmosphere within the lumen 662, the catheter 660 shrinks and reduces (shortens radially and longitudinally). This shrinkage acts like a spring squeezing down on the lumen in the catheter—in other words, it is a storage of potential energy. If the vacuum source is then cut off (e.g., the vacuum valve 620 is closed) and the vent valve 650 is opened to the vent fluid source 640, then the catheter 660 elongates and acts as a piston pulling against the vent liquid 642. Further, the vent liquid 642 is at a higher pressure (e.g., atmospheric pressure or slightly elevated by having a higher physical position than the patient) than the fluid in the lumen 662. Consequently, an amount of the vent liquid 642 enters through the vent valve 640 into the manifold 630 and then into the lumen 662 through the proximal manifold connector assembly 670. As the vent liquid 642 flows in and the catheter 660 expands to its normal or free steady state, momentum is created in the fluid column directed towards the distal end 664, referred to herein as a pressure pulse or pressure wave. In other words, a "pressure pulse" or "pressure wave" is momentum within a column of fluid that can act to move a distal portion of the fluid column in the catheter lumen distally out from a distal end of the catheter. This term relates to a given cycle of the vacuum and vent valves 620, 650 and is not limited to a single pressure transmission with that cycle. A pressure pulse, therefore, can include multiple pressure differentials with a given cycle of the vacuum and vent valves 620, 650. Thus, by adjusting a timing of the vacuum and vent valves to match a compliance and length of a particular catheter system (which can include the catheter and also the manifold and valves and other lumens in line with the catheter), a ROAR effect can be achieved for that catheter. In particular, one way to achieve the ROAR effect and prevent forward flow of the distal portion out from the distal end during each cycle is by regulating a timing of the vent valve 650.

Prior art aspiration thrombectomy systems periodically open and close a vacuum valve. Fluid rushes into the distal end of the catheter while the vacuum valve is open and vacuum is being applied to the fluid column. When the vacuum valve is closed, liquid rushing proximally through the lumen stops by hitting the closed vacuum valve. This causes pressure to build at the vacuum valve and create a bounce-back wave that carries momentum distally towards the distal end and ejects an amount of fluid distally from the distal end of the catheter. This action is referred to as a water hammer effect. The prior art repetitively opens and closes that vacuum valve. Thus, an amount of liquid ejects in a periodic manner out of the distal opening in those devices. This forward flow phenomena is undesirable in the area of thrombus removal because, when liquid is allowed to eject from the distal end and the physician is causing the distal end to approach the thrombus, the liquid could or will move the thrombus further distally, or it could break the thrombus up to allow arterial pressure to push the broken pieces further downstream, e.g., into smaller brain arterial vessels.

It would be, therefore, desirable to entirely prevent any distally directed pressure pulse reaching the distal end of the aspiration catheter in a thrombus aspiration removal system. As described herein, the system 600 has a response to the water hammer effect that is tuned to achieve a maximum water hammer effect without causing forward flow, which response achieves the most effective engagement and disruption of the thrombus.

Proximal and distal pressure measurement devices 690, 692 are illustrated diagrammatically in FIG. 47. In this exemplary embodiment, the proximal pressure measurement device 690 is adjacent or within the proximal manifold connector assembly 670 and/or within the proximal portion of the fluid column, and the distal pressure measurement device 692 is adjacent or within the distal end 664 or within the distal portion of the fluid column. An exemplary embodiment for measurement devices 690, 692 include a pressure transducer manufactured by TransducersDirect.com.

Measurement in the fluid column of the catheter 660 at or adjacent the manifold 630 and adjacent the distal end 664 reveals a time delay in travel of the pressure pulse—the pressure rises at the manifold 630 first and then pressure rises at the distal end 664 later. By knowing the time delay and the distance between the sensors, the speed of the wave can be calculated. By knowing the distance from the most distal sensor to the tip of the catheter 660, the time it will take for the wave to travel to the distal tip can be calculated. This information can be used by the controller to time the valves properly to stop the pressure pulse. If the pressure pulse is allowed to travel all the way to the distal end 664, then a distal portion of the fluid column in the lumen 662 will exit the distal end 664, e.g., forward flow. If, during this time, the distal end 664 is corked with a thrombus 4, that pressure pulse could or will eject the thrombus 4 distally. Alternatively, if the distal end 664 is approaching a thrombus 4, any pressure pulse exiting the distal end 664 could or will move the thrombus 4 further distally. Movement of the thrombus 4 in a distal direction before or after it has been captured and corked at the distal end 664 of the catheter 660 is to be avoided. Therefore, the pressure pulse needs to be reversed or stopped before that pressure pulse reaches a point where it could move the thrombus 4 either further downstream or off of the distal end 664 in the distal direction. Such reversal is referred to herein as "quelling" the pressure pulse.

Operation of the aspiration thrombectomy system 600 with the ROAR effect does not produce the same results as prior art catheters. When operated with the distal end 664 unobstructed, the vacuum valve 620 and the vent valve 650 are periodically opened and closed. Fluid rushes into the distal end 664 of the catheter 660 and into the canister of the vacuum source 610 while the vacuum valve 620 is open and vacuum is being applied to the fluid column. When the vacuum valve 620 is closed, the sudden stop of flow creates the pressure wave generated as described above due to the water hammer effect from the closing of the vacuum valve 620. The controller 700 is timed to control the vacuum and vent valves 620, 650 to create the ROAR effect even when the distal end 664 is open to vasculature and, therefore, any distally directed pressure pulse in the aspiration thrombectomy system 600 is quelled so that substantially no forward flow occurs during a thrombus retrieval procedure. Through experimentation, net flow of liquid at the distal end 664 remains positive in the proximal direction—in other words, while operating with the ROAR effect in the corked or un-corked state, liquid either moves through the distal end 664 towards the vacuum source (when un-corked) or does not flow at all (when corked). In both circumstances, substantially no liquid exits the distal tip 610.

To accomplish the ROAR effect, the change in the level of vacuum at the distal end is at least approximately 15 inHg, further, at least approximately 20 inHg, and, in particular, at least approximately 25 inHg. A time for the change in the level of vacuum from low to high or from high to low at the distal end is no greater than approximately 50 ms, further, no greater than approximately 30 ms, and, in particular, no greater than approximately 20 ms. This change can be referred to as a maximum pressure delta. Various combinations of these variables include a change in the level of vacuum of approximately 15 inHg and a time for that of no greater than 50 ms, or the change in the level of vacuum of approximately 20 inHg and a time for that change of no greater than 30 ms, or the change in the level of vacuum of approximately 25 inHg and a time for that change of no greater than 20 ms.

Figure 48:
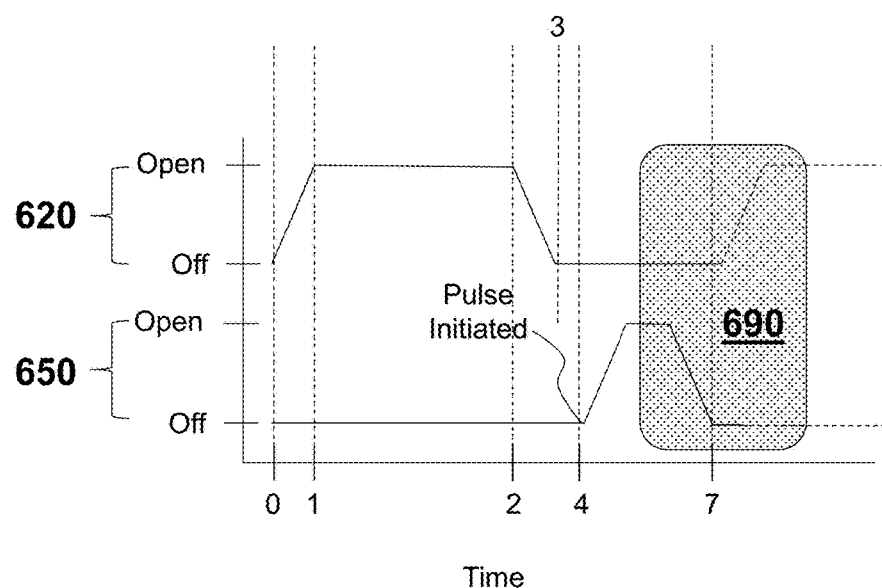
FIG. 48 is a graph of an exemplary embodiment of a waveform for operating the system of FIG. 47 with a ROAR process to quell pressure pulses.

The ROAR catheter 660 is operated to quell all pressure pulses in an exemplary embodiment according to the graph of FIG. 48. The state of the vacuum valve 620 is shown in the waveform at the top of the graph and the state of the vent valve 650 is shown in the waveform at the bottom of the graph. The repetitive cycle starts at time 0 with the valve starting to open in this exemplary embodiment. At time 1, the vacuum valve 620 is fully open and the vent valve 650 is closed. Vacuum continues until time 2, when the vacuum valve 620 starts to close. Closing of the vacuum valve 620 is not instantaneous and, therefore, the vacuum valve waveform decreases at a sharp angle and is fully closed at time 3. After the vacuum valve 620 is closed, at time 4, the vent valve 650 starts to open. This closing of the vacuum valve 620 initiates a water hammer and the closing of the vacuum valve 620 and subsequent opening of the vent valve 650 causes vent liquid 642 to enter the manifold 630 (and possibly the proximal end of the lumen 662). The potential energy stored in the compliant catheter 660 is also allowed to release due to the change in pressure from the negative pressure generated by the vacuum source 610 to the relatively larger pressure (e.g., arterial) existing in the vent fluid source 640. This combination of events initiates a pressure pulse at time 2 that travels distally through the lumen 662 towards the distal end. If there was no further change in the valves 620, 650, then liquid in the column will eject out from the distal end 664, i.e., forward flow. However, as shown in FIG. 48, after a relatively short vent-open time compared to the vacuum-on time, the vent valve 650 is closed (at time 7) and, shortly thereafter, the vacuum valve 620 is opened. This means that, while the pressure wave is travelling distally along the length of the lumen 662 of the catheter 660, when the vent valve 650 is closed to turn the vent liquid 642 off and the vacuum valve 620 is opened to turn vacuum back on (time 0 of the repeating waveform), switching of these valves 620, 650 causes vent liquid 642 to cease entering the manifold 630 and to move the fluid in the manifold 630 and in the lumen 662 proximally into the collection canister 612 of the vacuum source 610 (see, e.g., FIG. 55). Thus, a reverse momentum is imparted within the fluid column. This reverse momentum is sufficiently large enough to prevent the pressure pulse from ever reaching a point where the distal portion of fluid in the lumen 662 exits the distal end 664—thereby quelling the pressure pulse and preventing forward flow. The ROAR effect, therefore, retains a level of pressure at the distal end at less than or equal to physiological pressure. The area 690 of the two waveforms shown in FIG. 48 includes a time at which the pressure pulse has been quelled. The waveforms repeat in a periodic manner to continue the distal-then-proximal momentum pulse without ever allowing the distal portion to exit the distal end 664 of the catheter 660. The rapid change in pressure at the catheter tip from near full vacuum to nearly zero vacuum pressure is the ROAR effect. Under the ROAR effect, pressure at the distal end 664 can rise to just short of being arterial pressure and reversal of that rise is, then, started due to the reestablishment of vacuum. This allows the aspiration thrombectomy system 600 to approach a thrombus 4 without imparting distal movement to the thrombus 4 and to retain the corked thrombus 4 at the distal end 664 without any distal movement of the thrombus 4 caused by a change in pressure within the fluid column.

Figure 49:
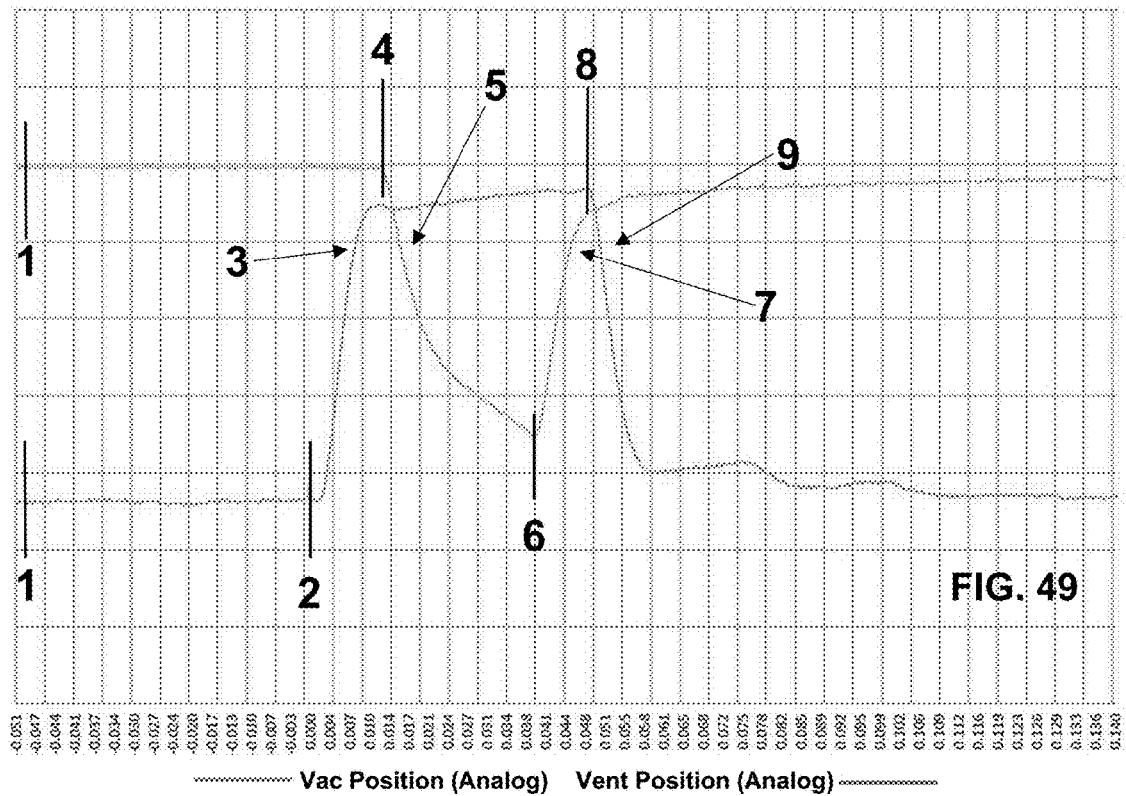
FIG. 49 is a graph illustrating an exemplary embodiment of one cycle of a waveform operation of a vacuum valve and a vent valve of the system of FIG. 47.

Another exemplary embodiment for creating the ROAR effect with the catheter 660 utilizing the vacuum valve 620 and the vent valve 650 is shown in the waveforms of FIG. 49, which are repeated at an exemplary rate of between approximately 1 Hz and approximately 250 Hz, further, between approximately 2 Hz and approximately 20 Hz, still further, between approximately 4 Hz and approximately 12 Hz, in particular, between approximately 6 Hz and approximately 8 Hz. At time 1, the vacuum valve 620 is in the open/on position and the vent valve 650 is in the closed/off position. At approximately time 2, the vacuum valve 620 starts transitioning to the closed/off position. At approximately time 3, the vacuum valve 620 is closed/off. At time 4, the vent valve 650 starts to open and at approximately time 5, the vent valve 650 is fully open. The vent valve 650 remains open while the vacuum valve 620 is closed until time 6, at which the vent valve 650 starts to close. The vent valve 650 is closed at approximately time 7. The vacuum valve 620 starts to open at time 8 and is partially open at approximately time 9. The vacuum valve 620 is full open when near the bottom extent of the curve in the graph. This process is repeated periodically, which in this example is at 10 Hz.

In what is referred to herein as static aspiration, the distal end 664 of the catheter 660 is pushed against a thrombus 4 while suction is applied to the catheter 660. The lower pressure in the catheter 660 creates a force on the clot 4 equal to a pressure differential across the clot 4 multiplied by the area of the inner diameter of the catheter 660. It is this force that "sticks" the clot 4 to the distal end 664 of the catheter 660 in an attempt to retrieve the clot 4 entirely.

In the ROAR cycle, suction is applied to the clot by rapidly opening a valve, causing a rapid rise in vacuum pressure. The source of suction is then turned off and a vent fluid source is rapidly opened. This relieves the vacuum present in the catheter 660, which again rapidly changes the pressure applied to the clot. The vent valve 650 is then rapidly closed and the vacuum valve 620 is rapidly opened. This cycle is repeated multiple times per second. For example, the period for repetition is between approximately 2 Hz and approximately 16 Hz, in particular, between approximately 8 Hz and approximately 12 Hz. The rapid drop of pressure across the clot 4 when the vacuum valve 620 is opened causes the clot 4 to accelerate into the lumen 662 of the catheter 660. The release of vacuum pressure when the vent valve 650 is opened causes the clot 4 to rebound back from the catheter 660. When the vacuum is applied again, the clot 4 once again accelerates towards the catheter 660. These accelerations and rebounds cause the distributed mass of the clot 4 to oscillate. The large internal accelerations of the distributed mass from the oscillation creates internal forces in the clot 4 that are high enough to exceed the tensile strength of the clot 4 and cause it to fail. The torn pieces of clot 4 are then aspirated all the way through the catheter 660 and into the vacuum collection canister 612. To maximize forces in the clot, the pressure differential across the clot and the rate at which this differential pressure is applied is maximized. The higher the rate at which this force is applied to the clot, the higher the internal acceleration of the distributed mass of the clot, and thus the higher the internal forces within the clot, and thus the higher the likelihood of the clot to tear. The times for the pressure change in both the up and down directions are about 20 ms either way. At 8 Hz, for example, each cycle is 125 ms and at 12 Hz each cycle is 83 ms. The greater the frequency of the cycle, the greater the number of these impacts that the catheter can have to interact with the clot. Using higher frequencies is, therefore, better, but only up to a point where there is not enough time to cause an effective enough pressure delta within each cycle.

Figure 50:
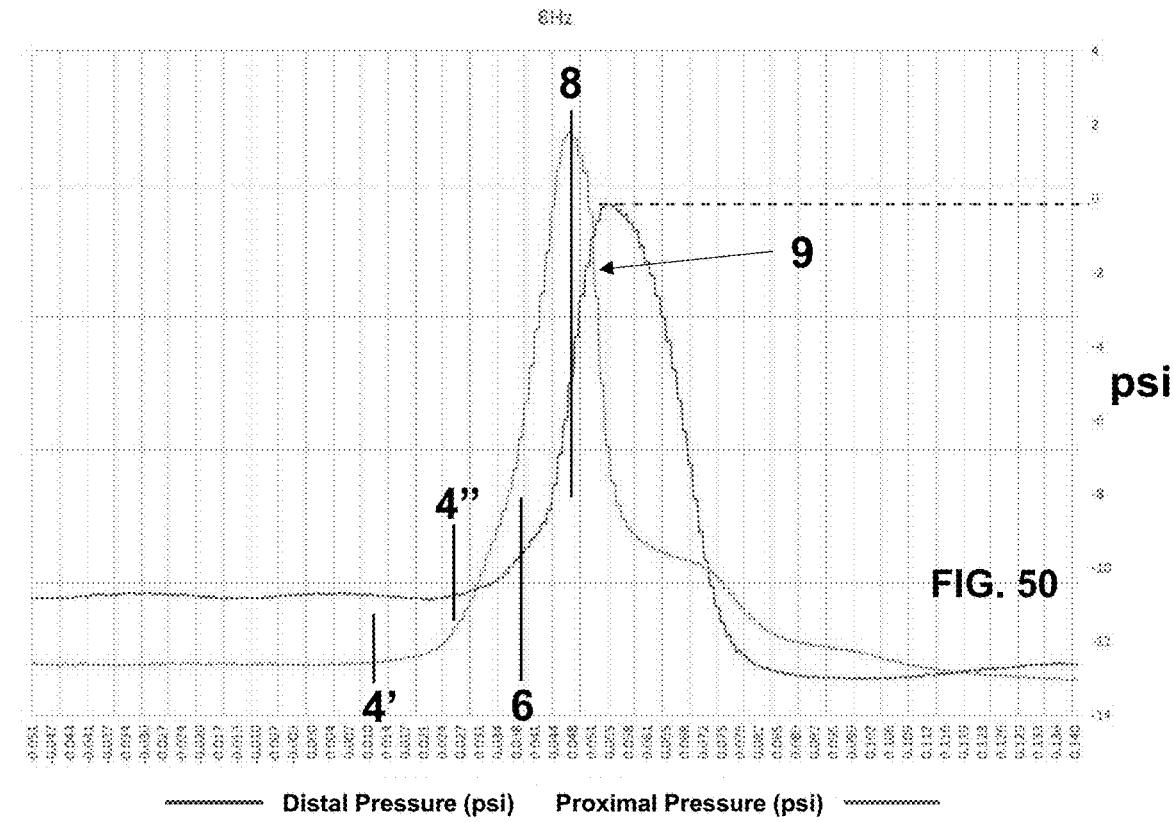
FIG. 50 is a graph illustrating pressure curves at a proximal portion and a distal portion of a lumen of a catheter of the system of FIG. 47 operating with the waveform of FIG. 49.
Figure 51:
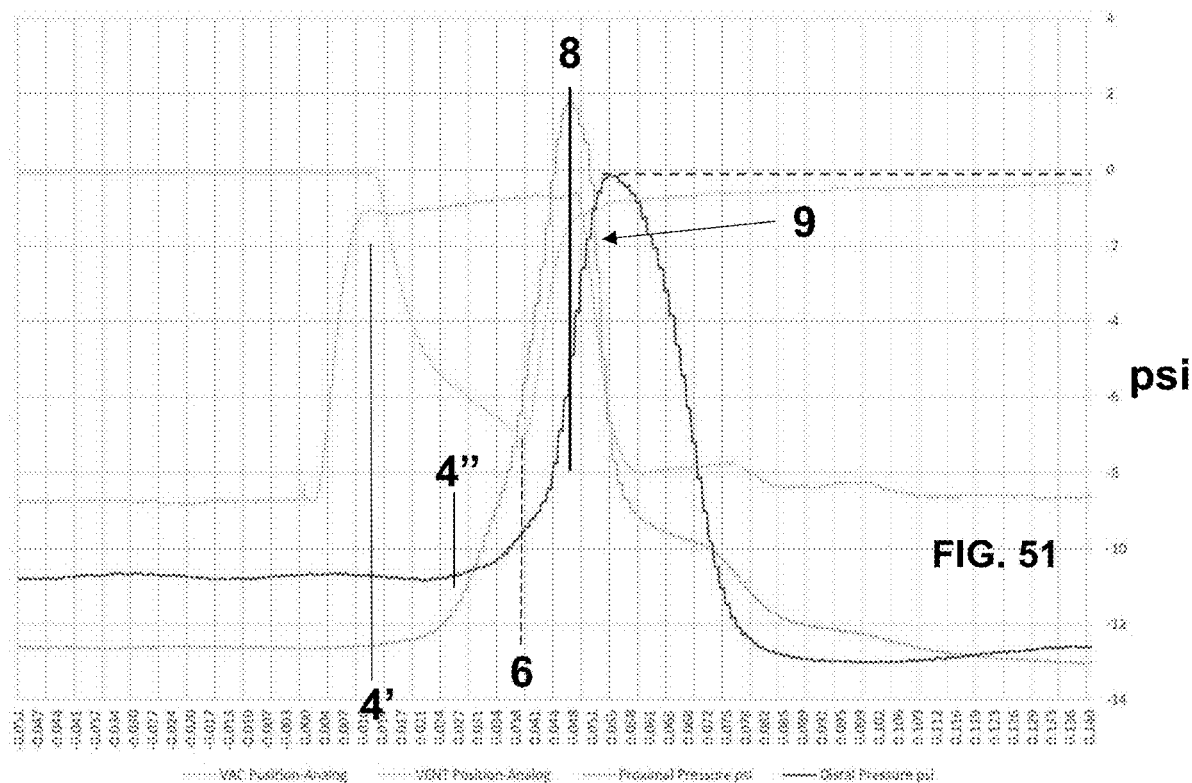
FIG. 51 is a graph illustrating the waveforms of FIGS. 49 and 50 combined together in time.

During operation of the catheter 660 with the ROAR effect, measurement of the pressure pulse can be undertaken with the proximal and distal pressure measurement devices 690, 692. The graph of FIG. 50 illustrates pressure sensed by these devices 690, 692 during the exemplary 10 Hz pulse present in FIG. 49 (FIG. 51 illustrates the graphs of FIGS. 49 and 50 superimposed on one another). The pressure sensed by the proximal pressure measurement device 690 starts at the lower pressure value (approximately at −13 psi) and the pressure sensed by the distal pressure measurement device 692 starts at a higher pressure value (approximately at −11 psi). This represents a partially corked system where an incomplete seal of the thrombus simulant to the catheter allows some flow by creating a slightly lower pressure at the distal measurement. At time 4, vacuum is off and the vent valve 650 starts to open. Accordingly, vacuum in the lumen 662 starts to be relieved. This means that pressure at the proximal pressure measurement device 690 starts to increase, which is evidenced by the upwards curve starting at approximately 4'. A short while later, as the change in pressure propagates distally down the catheter 660, pressure at the distal pressure measurement device 692 starts to increase, which is evidenced by the upwards curve starting at approximately 4". At time 6, the vent valve 650 starts to close and, therefore, no more vent liquid 642 is entering the manifold 630 to add to or augment the fluid column in the lumen 662. Pressure at the proximal pressure measurement device 690, nonetheless, continues to rise as the vacuum (negative pressure) is entirely removed or is compensated by the pressure of the vent liquid 642. Pressure at the proximal pressure measurement device 690 peaks and, as shown in FIG. 50, the pressure at the peak is at a positive pressure of approximately 2 psi—this occurs even though the aspiration thrombectomy system 600 does not actively apply any positive pressure to the fluid or the lumen 662. Rather, this level of pressure being >0.0 psi is due to the momentum of the fluid traveling within the lumen 662. Thus, a positive pressure within the lumen 662 is acceptable but it needs to be suppressed before arriving at distal end. At time 8, the vent valve 650 has already closed and the vacuum valve 620 starts to open at approximately the time of peak pressure at the proximal pressure measurement device 690. Opening of the vacuum valve 620 drops pressure within the lumen 662 and stops pressure at the proximal pressure measurement device 690 from going any higher (if not stopped at this level, then it is possible that pressure at the distal pressure measurement device 692 would be >0.0 psi, which means distal forward flow will occur out from the distal end). Quelling of the pressure pulse is proven by review of the pressure track of the distal pressure measurement device 692. As can be seen in the graph of FIG. 50, the pressure increase at the distal pressure measurement device 692 follows the pressure increase at the proximal pressure measurement device 690. At time 8, pressure recorded at the distal pressure measurement device 692 is still negative (approximately at −5 psi), but is rising. With continued operation of vacuum to and past time 9 (when the vacuum valve 620 is fully open), the peak pressure measured at the distal end 664 by the distal pressure measurement device 692 is less than 0.0 psi (horizontal dashed line), which means that the pressure pulse is quelled and that liquid from the distal portion does not exit the distal end 664, in other words, substantially no forward flow. The ROAR effect allows the clot simulant to remain sealed to the catheter and the system 600 is able to achieve the full vacuum of −13 psi at both measurements. Because the distal pressure is relieved almost to zero but then shortly arrives at the full −13 psi vacuum, the pressure delta illustrated is approximately 13 psi.

As described herein, it is possible to force flow from the distal end 664 of the catheter 660 while cycling between vacuum and vent. The rapid switching between vacuum and vent creates forward flow pressure pulses in the fluid column that, if not managed, will force the fluid column out of the distal end 664 of the catheter 660. The waves move through the fluid column at a very high speed through the medium. The speed is primarily a function of the density of the fluid, the compliance of the system (the bulk modulus), and the length of the fluid column. To prevent these waves from forcing the fluid column out of the catheter, the system is considered as a whole and the parameters of the valve switching cycle are set such that the forces that cause the fluid column to flow are controlled. To ensure that the fluid column does not exit the distal end 664 of the catheter 660, it is important that the catheter 660, any extension tube that connects to the catheter 660, the controller 700, and the valving sequence be tuned as a system.

The goal of the tuning process is at least two-fold: prevent the pressure waves generated during ROAR operation from causing forward flow and optimize the ROAR effect. The length of the fluid column is critical to the tuning of the system. The pressure wave moves rapidly within the fluid column. The time for the wave to reach the distal tip of the catheter is a function of this speed and the length of the fluid column. The speed is a function of the density of the fluid in the column and the bulk modulus of the catheter and extension. The bulk modulus refers to the compliance of the system: both the radial and the longitudinal flexibility of the catheter and the extension tube. The density of the fluid column is not as significant a variable as the bulk modulus unless it changes greatly, such as is the case if the fluid column has gaseous (air) bubbles in it. It is thus, important, to have all air purged from the system prior to implementing ROAR operation. For a given catheter and extension tube configuration, the bulk modulus and the length of the system is fixed. Compliance can be added to the system to change the speed and thus tune the timing of the pressure wave. A flexible length of tubing could be added in-line with the relatively stiff catheter and extension, for example. This flexible length of tubing expands as the pressure pulses occur during ROAR operation. This decreases the bulk modulus of the system and reduces the speed, thus slowing down the pressure wave and increasing its transit time to the distal tip of the catheter. Compliance can be added in other ways as well, such as by including a piston backed by a spring in a bore that communicates with the catheter lumen such that the pressure wave displaces the piston, which increases compliance of the system. By manipulating the compliance and the valve timing, the system can be tuned for many different combinations of catheters and extension lines. Careful tuning results in achieving a resonant condition. If the suction and release pulses in the catheter are tuned to match a natural frequency of the clot, enhanced ROAR effect can be achieved.

Tuning can happen statically or dynamically. A statically tuned system is tuned so that the catheter 660 (and any extension tube that connects to the catheter 660) is mated to the controller 700 with a fixed valving sequence (such as the exemplary configuration shown in FIGS. 29 and 30). The controller 700 senses the presence of the catheter 660 when it is attached and verifies that it is the correct one for the tuned sequence of that controller 700. If the correct catheter is not sensed, the tuned sequence does not initiate. A dynamically tuned system is, in comparison, tuned during operation. Prior to operation, a valve sequence is initiated that creates a series of pressure pulses in the catheter 660. Sensors, such as strain gauges, on the catheter 660 and/or an extension tube detect these pulses and are used to adjust parameters of the controller 700 for operation to create the ROAR effect. The catheter 660 contains and transmits critical data, such as its length, to the controller 700. Using this tuning, any catheter, within limits, could be used without causing the fluid column to flow from the distal end 664 during ROAR operation. Alternatively, the catheter 660 and the extension can be tuned at the manufacturer and the specifics of the valve timing can be transmitted to the controller 700 by the catheter 660.

In an exemplary embodiment, the valve sequence is as follows:
the vacuum valve 620 is closed;
a time later the vent valve 650 is opened;
a time later the vent valve 650 is closed;
a time later the vacuum valve 620 is opened; and
a time later the sequence is repeated.

When the vent valve 650 is opened, a bit of vent liquid 642 enters the system and creates a pressure pulse. If the vent valve 650 is not closed, and the vacuum valve 620 is not opened before the pulse reaches the distal end 664 of the catheter 660, the fluid column will exit the distal end 664 of the catheter 660 as forward flow. To prevent the fluid column from exiting the catheter 660, it is this time—the time that it takes for the pressure pulse to traverse the catheter—for which the system must be tuned. Additionally, the pressure pulse from closing the vacuum valve 620 in a flow condition will cause a pressure increase that must be quelled by opening the vent valve 650 before it causes forward flow.

Figure 52:
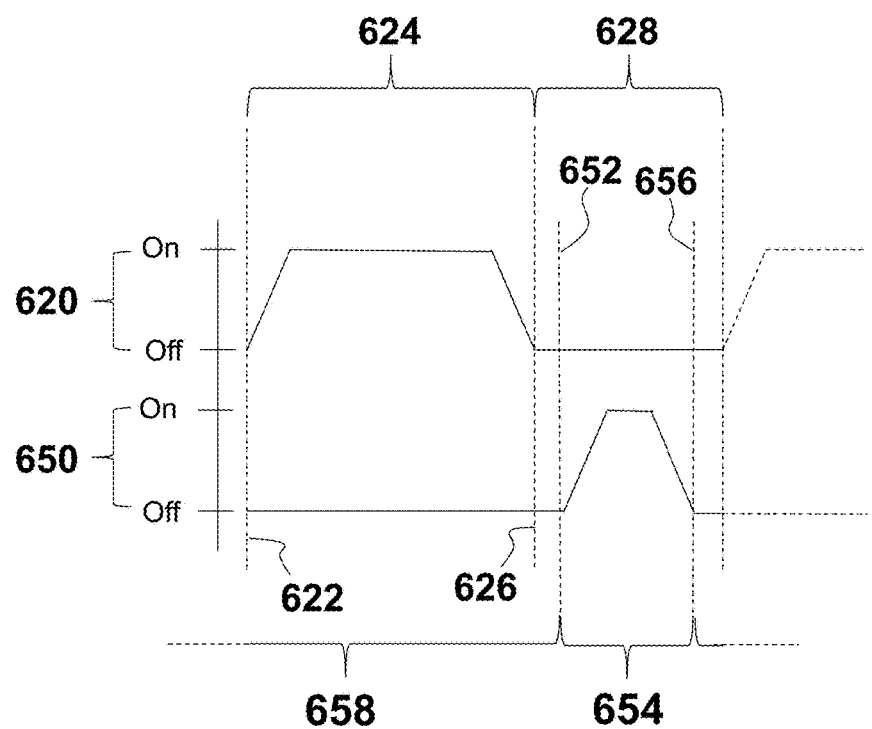
FIG. 52 is a graph of an exemplary embodiment of a waveform for operating the system of FIG. 47 with a ROAR process to quell pressure pulses.

Tuning is accomplished by selecting appropriate times for the vacuum cycle and the vent cycle. In this regard, the vacuum cycle includes Vacon time 622, Vacon duration 624, Vacoff time 626, and Vacoff duration 628 and the vent cycle includes Vnton time 652, Vnton duration 654, Vntoff time 656, and Vntoff duration 658. Accordingly, tuning is explained with reference to FIG. 52. A cycle time is the duration of the repetition of the entire cycle. At 8 Hz, the cycle time is 125 ms and at 12 Hz, the cycle time is 83.33 ms. The cycle time is determined by adding the Vacon duration 624, the Vnton duration 654 and the first and second times in the cycle that both the vacuum and vent valves 620, 650 are off, referred to as the "double-off" or "double-closed" times or states. The cycle time is optimized by the dynamics or the resonance of a particular catheter 660. The Vacon duration 624 must be long enough for the system to pump down to full vacuum and the longer the vacuum is on during a particular cycle, the better the aspiration of the thrombus 4. In this embodiment, opening only the vacuum valve is referred to as the "vacuum-only" state. The first double-off time, which is the time after the vacuum is turned off (vacuum valve 620 closed) up until the time that venting begins (vent valve 650 opens), has an effect on the extent to which forward flow occurs. As this is a short time, such forward flow is referred to as flow burping. Through experimentation, an exemplary embodiment of an 0.071" inner diameter catheter 660 experiences flow burping when the first double-off time is greater than approximately 30 ms; the longer the double-off time, the greater flow burping. During ROAR operation, the first double-off time is about 10 ms; therefore, this is significantly less than the flow burping threshold, which means that substantially all forward flow is quelled. The Vnton duration 654 is determined by a maximum time that occurs before a corked clot 4 is dropped from forward flow. A ratio between the Vnton duration 654 and the second double-off time is a compromise for the longest Vnton time 654 and a minimum of the first double-off time. In this embodiment, opening only the vent valve is referred to as the "vent-only" state. Finally, with respect to the second double-off time, the vent valve 650 is off (fully closed) before the vacuum valve 620 is opened and vacuum recommences.

Figure 53:
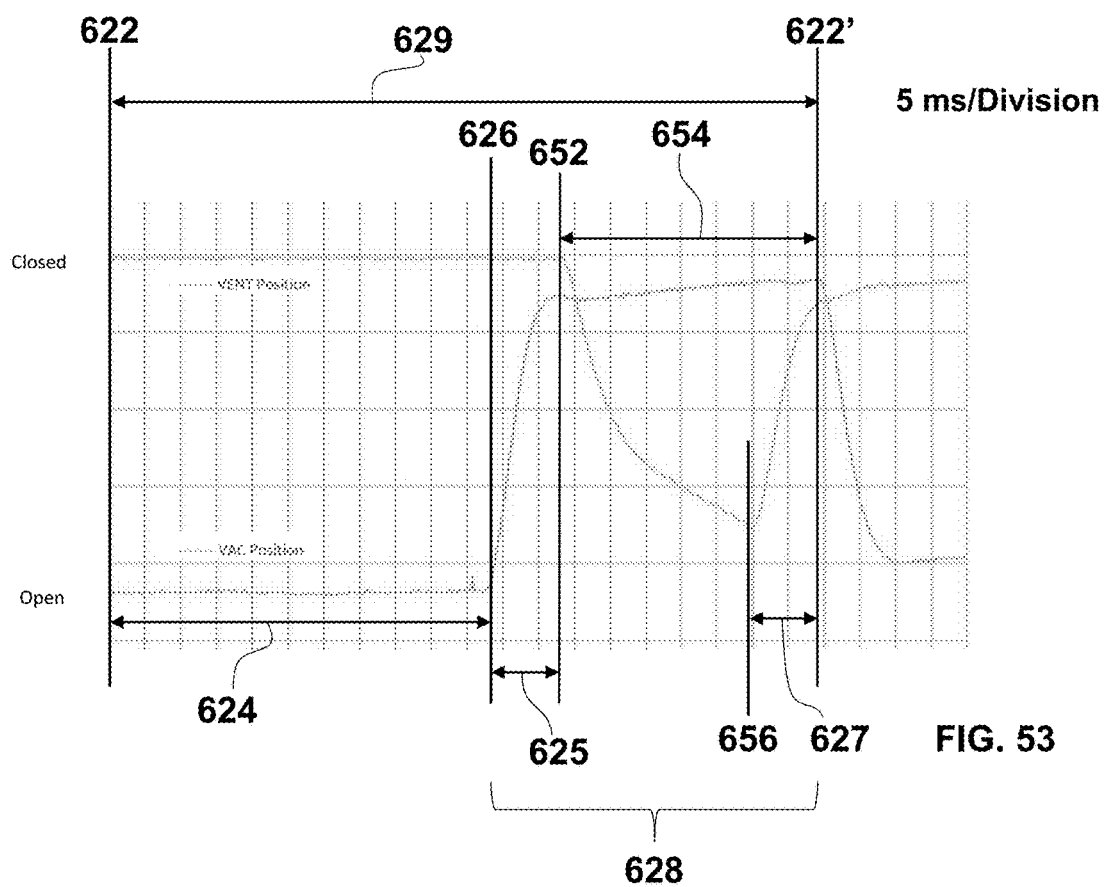
FIG. 53 is a graph illustrating positions of the vacuum and vent valves of the system of FIG. 47 for tuning the valves to create a ROAR effect.

The calculation is explained further with regard to the valve position graphs in FIG. 53. Starting from the left of the graph at Vacon time 622, the vent valve 650 is closed and the vacuum valve 620 is open. The Vacon duration 624 is long enough for the system 600 to pump down to full vacuum (between approximately 10 ms and approximately 50 ms, in particular, approximately 30 ms). The longer the Vacon duration 624, the better the catheter 660 performs because of increased flow rate in the proximal direction. There is a compromise based on achieving a higher frequency for more hits/sec on the clot 4. In an exemplary embodiment, the Vacon duration 624, calculated from the Vacon time 622 to the Vacoff time 626, is between approximately 40% and approximately 60% of the cycle time 629. As set forth above, the cycle time 629 is a minimum determined by summation of Vacon duration 624 plus the first and second double-off times 625, 627 plus the Vnton duration 654. The Vnton duration 654 is short enough to fill the lumen with vent liquid without causing forward flow (between approximately 10 ms and approximately 50 ms, in particular, approximately 30 ms). The first double-off time 625 is set based upon when open flow burping occurs. The maximum value for the first double-off time 625 applies to either of the periods from the Vacoff time 626 to the Vnton time 652 or the Vacoff time 626 to the Vacon time 622' whichever is shorter. Each of these values are optimized by the dynamics/resonance/compliance/length of the particular catheter 660 and extension set.

From this, some observations can be made. When the vent is opened, a pressure pulse is generated. It is important to stop the pressure pulse before it reaches the distal end. If the pressure pulse is not stopped before it reaches the distal end, the catheter 660 will experience forward flow. The way to stop the pressure pulse is to either close the vent and/or turn the vacuum back on if the vacuum was off prior to venting. If the vacuum remains on, then there is a need to turn the vent off. Or, if the vacuum does not remain on, the vent is turned off and the vacuum is turned back on before the pressure pulse makes it to the distal end 664. In other words, the vent needs to be closed before the pressure pulse makes it to the distal end 664 and the vacuum has to be turned on. So, the condition of merely opening the vacuum valve 620 when the vent valve 650 is opened may not be enough to quell the pressure pulse because of the low resistance between the vent and the vacuum; the vent will overwhelm the vacuum so the vacuum cannot have an effect over the length of the catheter. The time that it takes for the pressure pulse to propagate to the tip of the catheter 660 and then cause forward flow is used to define the time that the vent valve 650 is left open. The time that the vent is left open is selected to be shorter than the time it takes for the pressure pulse to propagate to the distal end 664.

Figure 55:
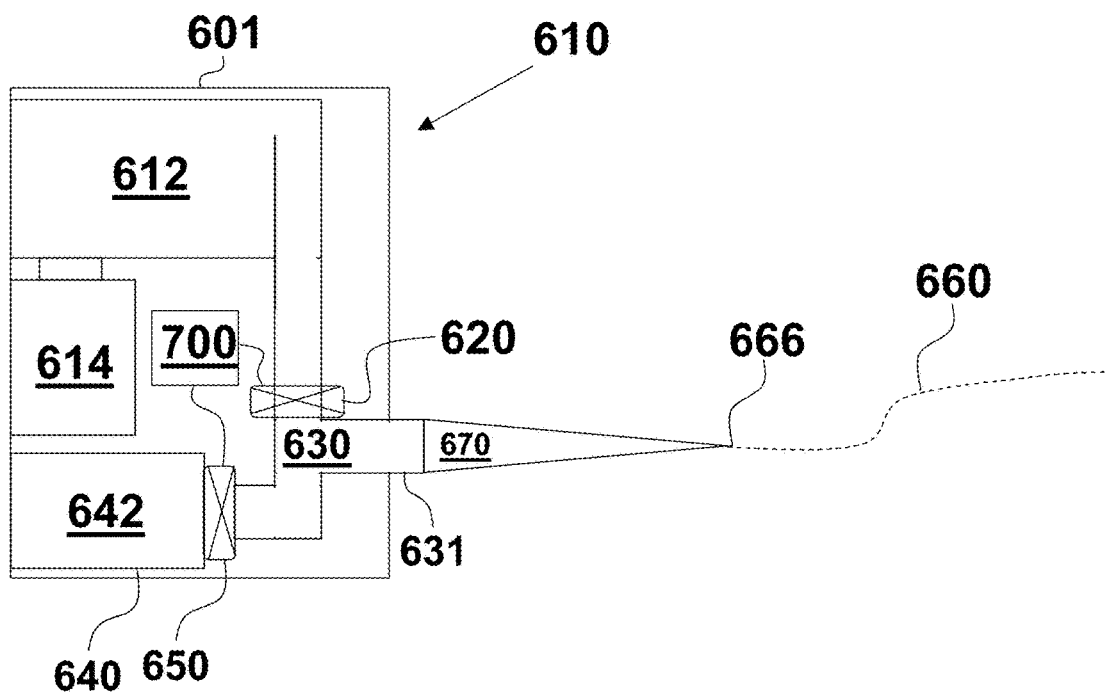
FIG. 55 is a block diagram of an exemplary embodiment of a self-contained, aspiration thrombectomy system.

In an exemplary embodiment illustrated diagrammatically in FIG. 55, all portions of the aspiration thrombectomy system 600 except for the ROAR catheter 660 are incorporated into the body 601 of the vacuum source 610. In particular, the vacuum source 610 comprises the body 601, a collection canister 612, and a vacuum motor 614. The vacuum motor 614 is fluidically connected to an outlet of the collection canister 612 and the input of the collection canister 612 is fluidically connected to a vacuum side of the manifold 630. Accordingly, vacuum generated by the vacuum motor 614 imparts vacuum within the collection canister 612 to draw fluid into the collection canister 612 from the manifold 630 but not into the vacuum motor 614. The vacuum valve 620 present at the manifold 630 prevents input fluid received at the manifold 630 from entering the collection canister 612 and closes off the manifold 630 from vacuum generated by the vacuum motor 614. The vent fluid reservoir 640 containing the vent liquid 642 is fluidically connected to a vent side of the manifold 630. The vent valve 650 present at the manifold 630 closes off the manifold 630 from the vent liquid 642 and prevents liquid within the manifold 630 from entering the vent fluid reservoir 640 (as pressure in the manifold 630 is typically lower than pressure within the reservoir 640, liquid from the manifold 630 will not typically enter the reservoir 640). In summary, a catheter input port 631 of the manifold 630 is fluidically connected to the collection canister 612 through the vacuum valve 620 and is fluidically connected to the vent liquid 642 in the reservoir 640 through the vent valve 650. The catheter input port 631 is fluidically connected to the downstream end of the proximal manifold connector assembly 670. The upstream end of the proximal manifold connector assembly 670 is fluidically connected to the proximal end of the catheter 660.

Figure 54:
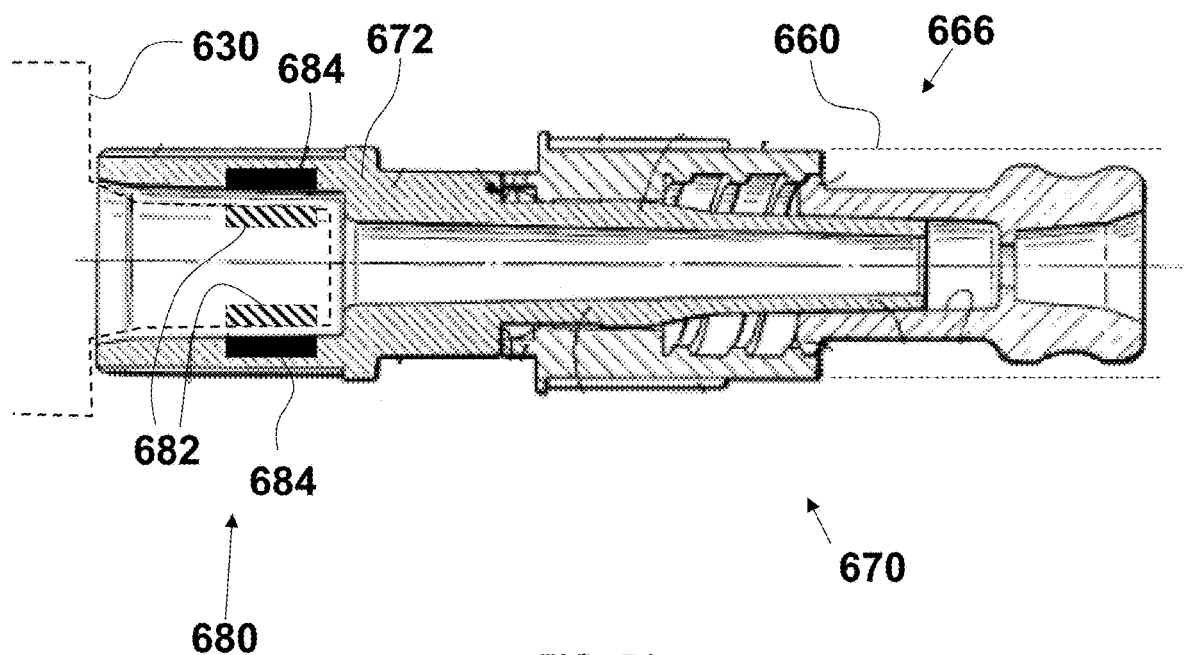
FIG. 54 is a fragmentary, longitudinal cross-sectional view of a proximal manifold connector assembly for the system of FIG. 47.

Direct connection of the catheter 660 to the aspiration thrombectomy system 600 is explained with regard to FIGS. 54 and 55. The proximal manifold connector assembly 670 connects the proximal end 666 of the ROAR catheter 660 to the manifold 630. In an exemplary embodiment shown in FIG. 54, the proximal manifold connector assembly 670 comprises a male luer lock fitting 672 connected to the manifold 630 (shown in dashed lines), either removably or integrally. The assembly 670 includes a ROAR identification (ID) sub-assembly 680. The exemplary embodiment of the ID sub-assembly 680 shown in FIG. 54 comprises an inductive sensing device or sensor 682 connected to the manifold 630. The inductive sensor 682 detects the presence of an inductive sensed part 684 that is present in or integral with the proximal manifold connector assembly 670. In an exemplary embodiment where the manifold 630 can be used with various different ROAR catheters 660, each of the types of ROAR catheters has a unique inductive sensed part 684 and the inductive sensor 682 of the manifold 630 is able to determine which type of ROAR catheter 660 is attached. Accordingly, with an appropriate communication of the ROAR catheter 660 type to the controller 700, the controller 700 is able to operate the ROAR catheter 660 according to its own unique configuration to produce the ROAR effect for every one of the different ROAR catheters 660 that are used.

When the sensor 682 does not detect a sensed part 684 and the aspiration thrombectomy system 600 is, nonetheless, operated, the controller 700 will automatically prevent ROAR operation of aspiration thrombectomy system 600 and that connected catheter will only be operated as a standard vacuum catheter.

Figure 56:
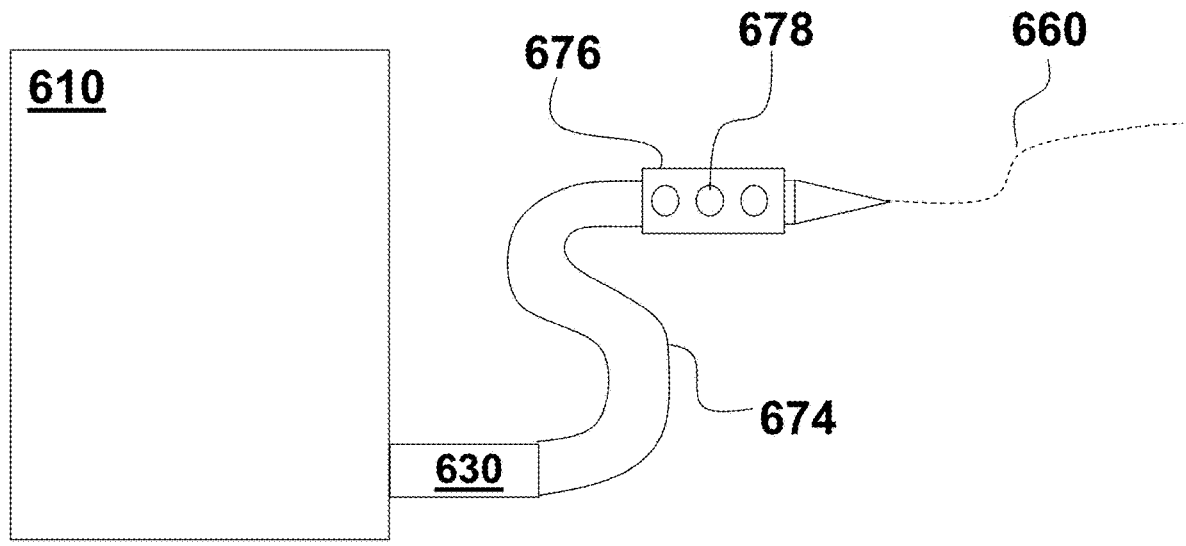
FIG. 56 is a block diagram of the system of FIG. 55 with an exemplary embodiment of a proximal manifold connector assembly having remote controls.
Figure 57:
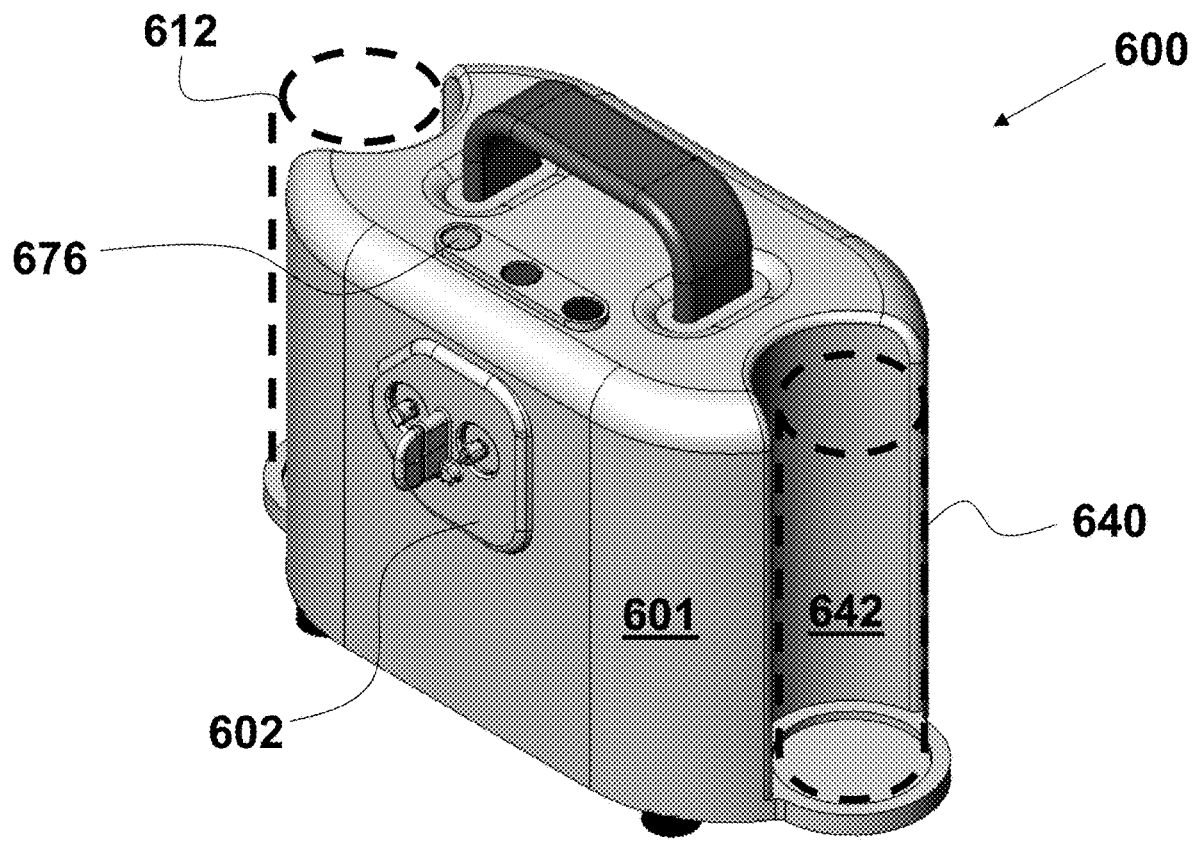
FIG. 57 is a perspective view of an exemplary embodiment of a self-contained, aspiration thrombectomy system with a collection canister and a vent liquid reservoir indicated diagrammatically.
Figure 58:
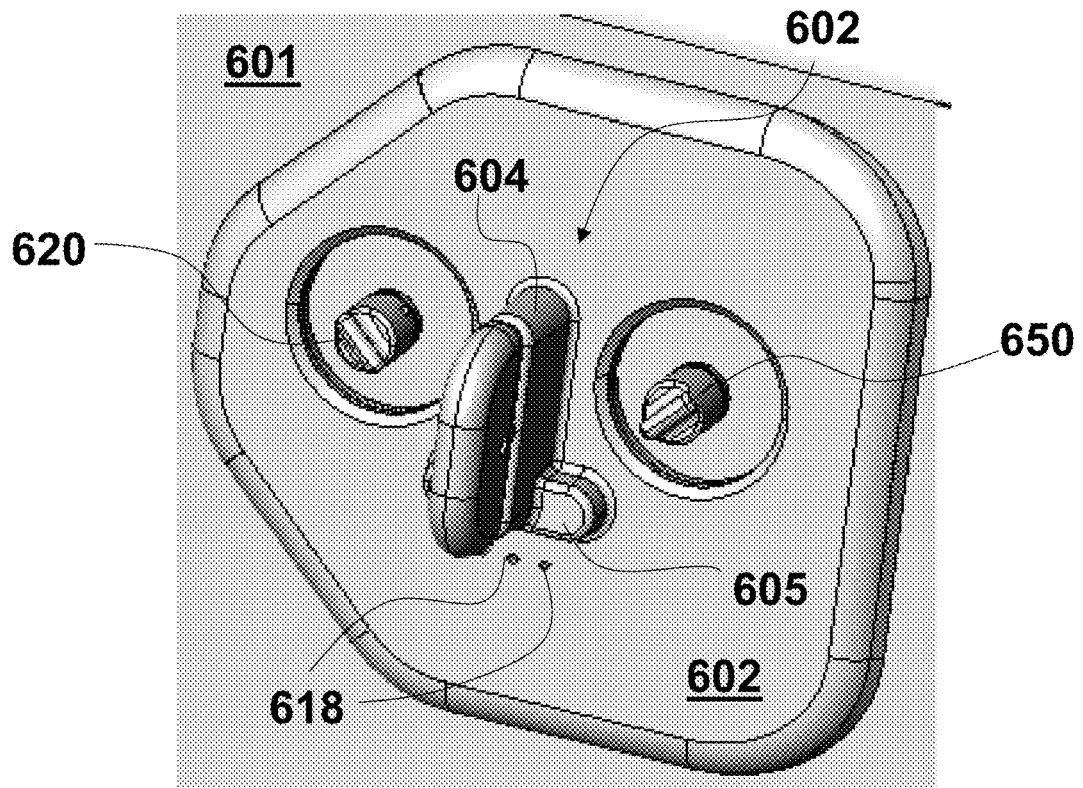
FIG. 58 is a fragmentary, perspective view of a cassette connection assembly of the system of FIG. 57.
Figure 59:
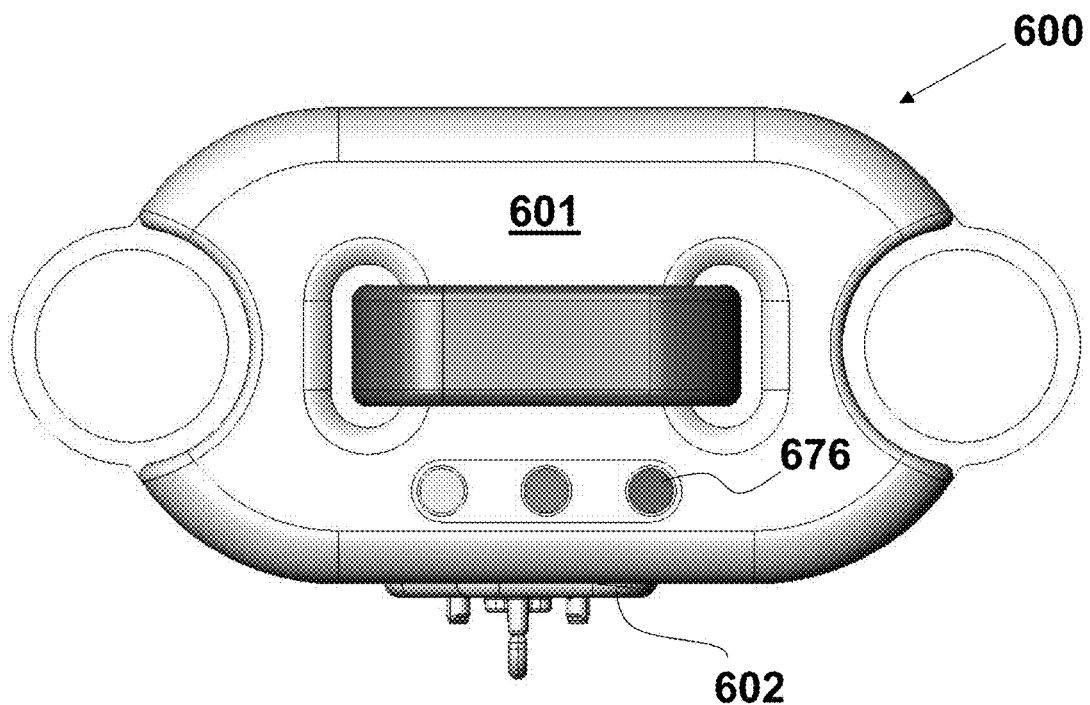
FIG. 59 is a top plan view of the system of FIG. 57.
Figures 60, 61:
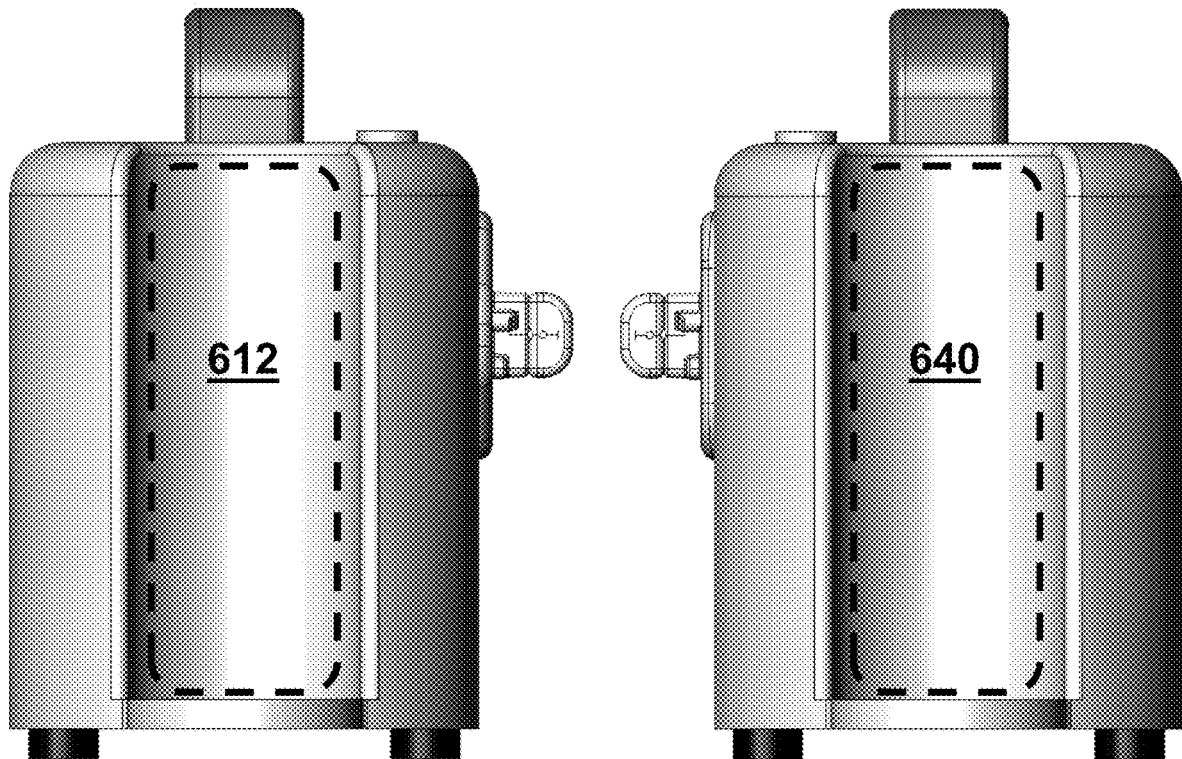
FIG. 60 is a left side elevational view of the system of FIG. 57.
FIG. 61 is a right side elevational view of the system of FIG. 57.
Figure 62:
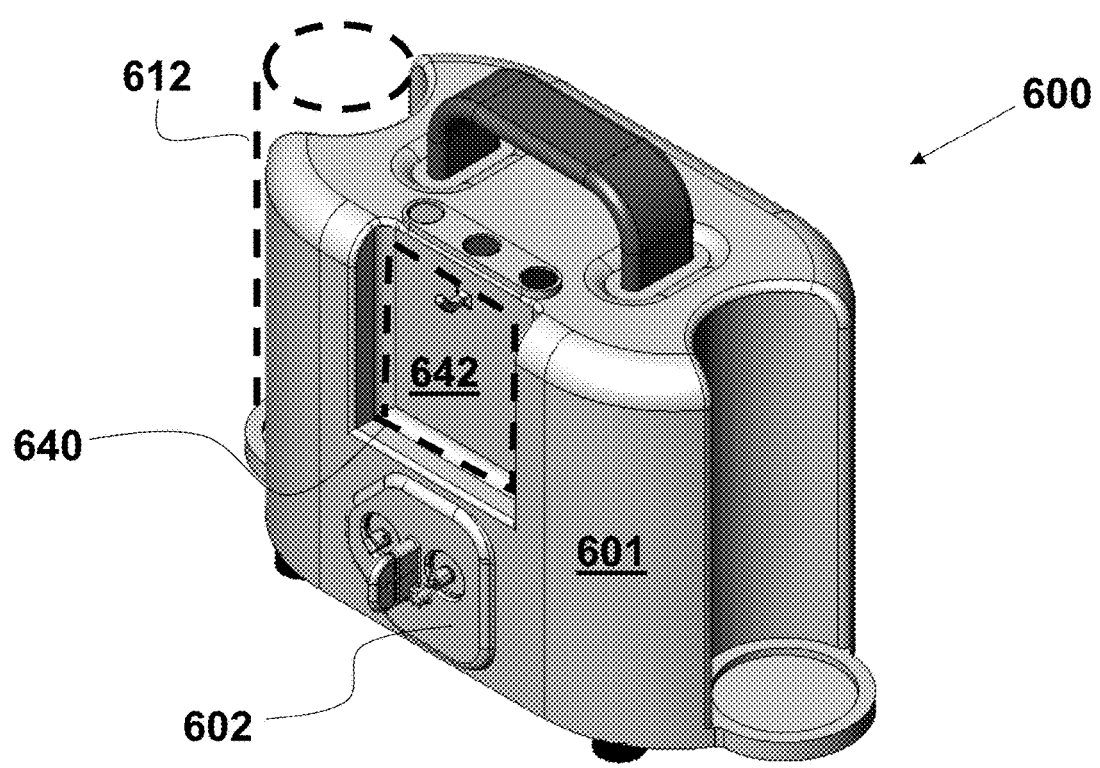
FIG. 62 is a perspective view of an exemplary embodiment of a self-contained, aspiration thrombectomy system with a collection canister and a hanging vent liquid reservoir indicated diagrammatically.
Figure 63:
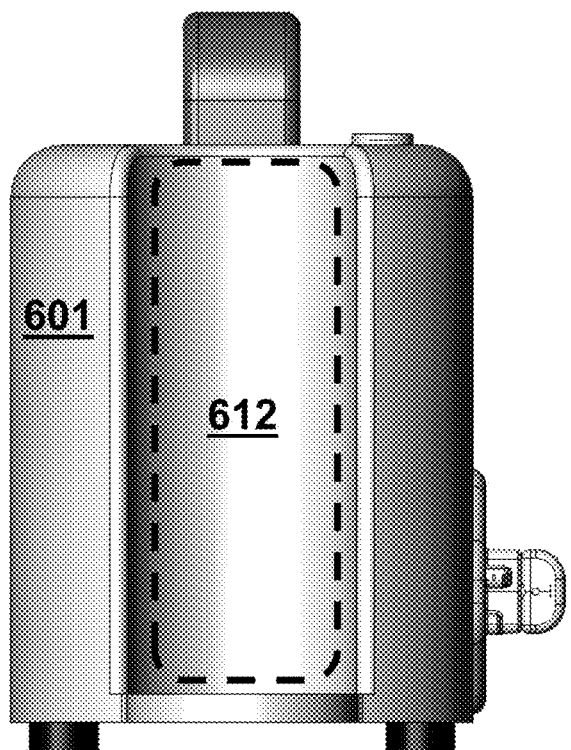
FIG. 63 is a left side elevational view of the system of FIG. 62.
Figure 64:
FIG. 64 is a right side elevational view of the system of FIG. 62.
Figure 65:
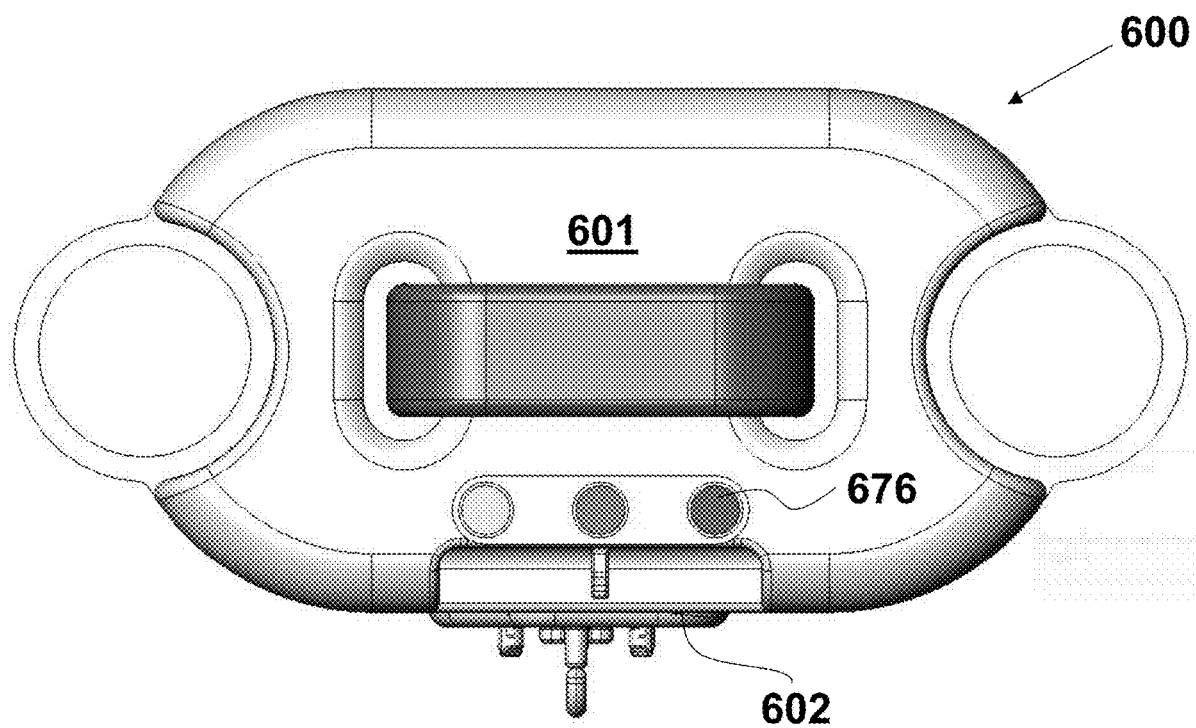
FIG. 65 is a top plan view of the system of FIG. 62.
Figure 66:
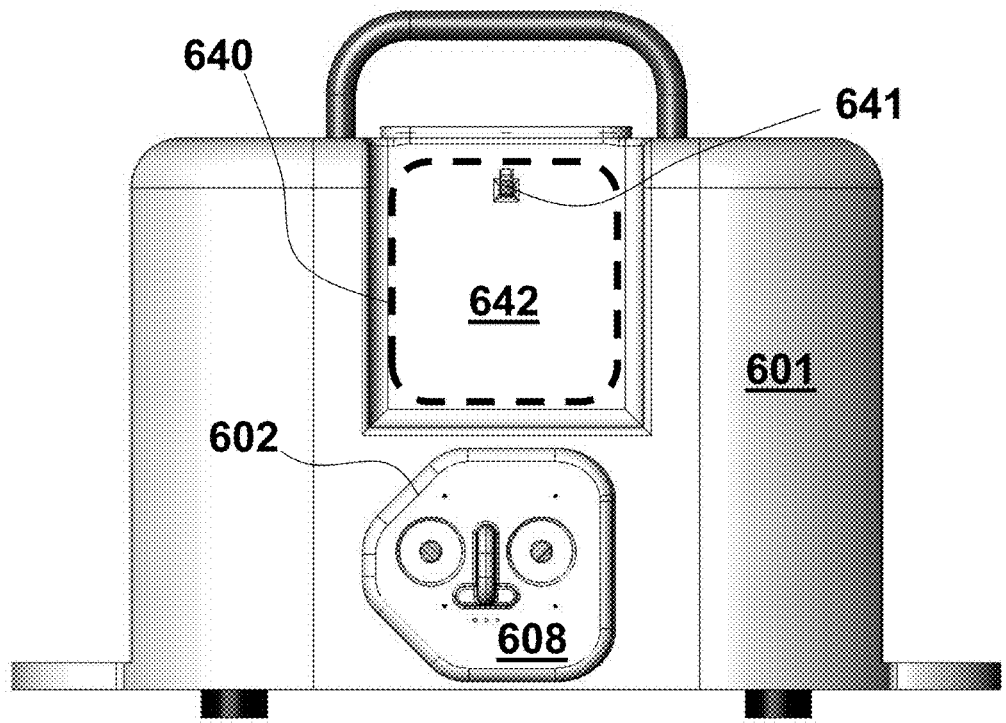
FIG. 66 is a front elevational view of the system of FIG. 57.
Figure 67:
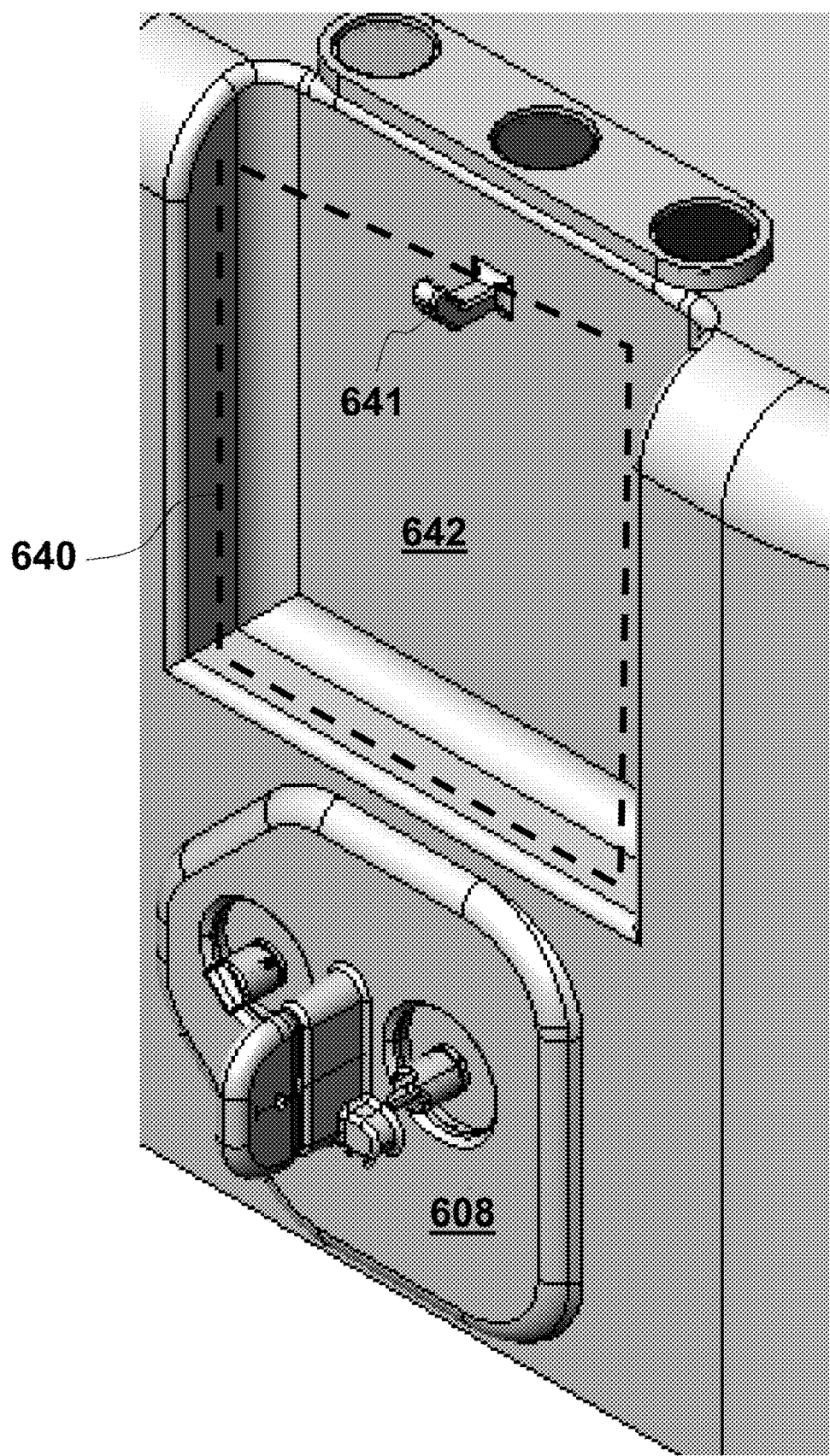
FIG. 67 is a fragmentary, front perspective view of cassette connection assembly and the hanging vent liquid reservoir of the system of FIG. 57.

Indirect connection of the catheter 660 to the aspiration thrombectomy system 600 is explained with regard to FIG. 56. The proximal manifold connector assembly 670 can simply be a fitting 672 as shown in FIG. 54 or it can be or include a separate extension line 674 between the catheter input port 631 and whatever catheter 660 (standard or ROAR) that is to be used along with the aspiration thrombectomy system 600. In an exemplary embodiment of the extension line 674, not only does the extension line 674 comprise a lumen extension for aspiration through the catheter 600, the extension line 674 also comprises system controls for operating the aspiration thrombectomy system 600. These controls include, for example, turning on and off the vacuum motor 614 and turning on the ROAR operation (e.g., one button for each of these or an on/off switch for vacuum and a push-to-start button for ROAR). As shown in the diagram of FIG. 56, the extension line 674 has a distal end that is able to connect to both standard catheters and ROAR catheters 600—as both can be used with the aspiration thrombectomy system 600. When the standard catheter is connected to the extension line 674, the aspiration thrombectomy system 660 only acts as a standard vacuum pump and ROAR is disabled. When a ROAR catheter 660 is connected to the extension line 674, identification sub-assemblies in the ROAR catheter 660 and the extension line 674 inform the system 600 which ROAR catheter 660 and which extension line 674 are connected.

In the exemplary embodiments with digital control of the vacuum and vent valves 620, 650, a processor and memory in the controller 700 stores the identification data and, upon identification of a particular ROAR catheter (e.g., different lengths, different outer diameters, different materials), the controller 700 loads the valve sequence and operates the vacuum and vent valves 620, 650 according to the characteristics of the particular catheter connected to the vacuum source 610. In one exemplary embodiment, the identification data can be preprogrammed at the manufacturer for all ROAR catheters 660 that currently exist. Thus, with direct connection of the ROAR catheter 660 to the system 600, the controller 700 can operate without receiving any information other than the identity of the catheter 660. If a ROAR extension line 674 is used between the ROAR catheter 660 and the controller 700 (in other words, an extension line that is ROAR compatible and is able to inform the system 600 of its augmentary characteristics to those of the ROAR catheter 660 to which it is connected), the controller 700 can operate without receiving any information other than the identity of the catheter 660 and the identity of the intermediate extension line 674 because connection with the ROAR extension line 674 allows the system 600 to detect which particular one of the different ROAR catheters 660 has been connected to the distal end of the ROAR extension line 674 and then to operate ROAR in a predefined manner appropriate for that particular ROAR catheter 660 with the ROAR extension line 674. In the case of RFID or near field communication (NFC), the chip embedded in the ROAR catheter 660 is programmed with the specific valve timings required by that catheter 660. The controller 700 reads these values and functions properly for that catheter 660. This ensures future compatibility with new generation catheters that require different tuning, which tuning would not be known at the time the controller 700 is programmed at the manufacturer. If the catheter to be used is not a ROAR catheter 660, then ROAR should not be used with that catheter because of the high probability of forward flow at the distal end. Accordingly, the system 600 automatically prevents use of the ROAR effect when a non-ROAR catheter is connected to the distal end of the ROAR extension line 674 or is connected directly to the system 600 or is connected to the distal end of a non-ROAR extension line 674.

The identification sub-assemblies include various measures present at least at the proximal end of the ROAR catheter 660 (e.g., the inductive sensing system 682, 684 or a 1-wire detection system, such as a DALLAS Semiconductor encryption chip, RFID, Bluetooth low energy (BLE), metallic touch pads, a simple passive design based upon resistors (in series for catheter and extension, to name a few). In the sub-assemblies, there can be two or more electrical contacts. For example, there can be three contacts including power, ground, and a signal using a Hall sensor. In a two-contact configuration, there can be a 2-wire configuration using resistors and mechanical switches. Resistance can be measured between two contacts and, depending on the resistance, a state of the switch can be detected. Power and signal can be combined on one line (plus an additional ground line) to create a "one-wire" connection, for example, using a DALLAS chip mentioned above. An identification sub-assembly also can be present at the distal connection (e.g., a Luer fitting) of the extension line 674 (to contact with the identification sub-assembly at the proximal end of the ROAR catheter 660) and extend back through the extension line 674 to a communication connection with the vacuum source 610, e.g., the proximal manifold connector assembly 670. Therefore, the aspiration thrombectomy system 600 has an ability to sense/detect when a ROAR catheter 660 is connected as differentiated from a standard catheter (i.e., not ROAR). Connection of the ROAR catheter 660 enables use of the ROAR function; connection of a non-ROAR catheter (or, e.g., to a side port of a rotating hemostasis valve (RHV)) disables use of the ROAR function and only normal aspiration is available. Where the identification sub-assembly includes electrical contacts in the ROAR catheter 660, the conductive connection to the vacuum motor 614 can utilize one or more coils of the ROAR catheter 660 as one of these conductors. Alternatively, two or more conductors can be wrapped within the ROAR catheter 660. Alternatively, or additionally, conductors can be bonded on the outside of the ROAR catheter 660.

In addition to the exemplary embodiments where the system 600 already stores the operating parameters for performing aspiration and automatically uses those parameters when the ROAR catheter 660 and/or the extension line 674 is connected or where the ROAR catheter 660 or the extension line 674 provides the operating parameters for performing aspiration, the user can be provided with selectable programs in the controller. These selectable programs can be, in one exemplary embodiment, programmed where the controller 700 is manufactured. The user has an instruction manual associating the particular ROAR catheter 660 and/or the extension line 674 being used with a code that loads in the operating parameters, such as pressures, delays, timing. Instead of an instruction manual, these operating parameters can be manually entered by the user instead of through the selectable program(s), for example, by reading the information the instructions for use (IFU) or the packaging of the system 600, or ROAR catheter 660, or extension line 674. In addition, if the user has a desired method of operation (for example, to increase a particular timing), the user can enter the parameter(s) directly through a user interface on the system 600. In other exemplary embodiments, a code supplier (e.g., a QR code, a barcode, or an RFID chip) could be on the packaging of one or more of the components and the user presents that code supplier to the controller for reading. In this regard, the system 600 comprises a bar-code reader and/or a QR code reader and/or an RFID communication device. With a display on the system 600, in another exemplary embodiment, the screen presents parameters to the user and those parameters could be fixed or alterable by the user. In other words, the user could accept or alter the parameters shown. In a particularly inexpensive embodiment, the parameters can be "stored" on a punch card that is supplied with the ROAR catheter 660 or the extension line 674 and the system 600 has a punch card reader. In this embodiment, the user inserts the inexpensive card (e.g., provided with a covering that protects it from liquids present in the operating room) into the card reader and the controller 700 utilizes the parameters on the card or utilizes a code on the card, which code is associated with a set of stored parameters.

All of these embodiments could present the operator with a choice of alternative programs or parameters, or the system 600 could list the parameters that are about to be utilized separately on a display screen and then allow the operator to select those parameters or alter the provided parameters. Similarly, operators are able to store parameters/programs into empty memories within the controller 700. The stored information provided by the catheter, the extension line, the card, the code, etc., could be either ROAR parameters or, alternatively, the information can be characteristics of the catheter and the extension line so that the controller 700 could make compensations to provide a predefined ROAR waveform at catheter tip. In other words, rather than offer up stored ROAR programs, the catheter and the extension line could simply give information to the controller 700 so that the timing and pressures could be modified for each catheter/extension line combination to achieve the predefined ROAR pressure/time profile. By storing either compensation parameters or actual time/pressure parameters, the controller 700 is able to allow future catheters and extensions not yet available. Further, chips, resistors, RFIDs, or BLE could be used to prevent use of the system 600 with catheters not provided by the manufacturer of the system 600, and/or to present a warning or alarm condition to the operator so that they know that the catheter and/or extension is not supported by the system 600.

One exemplary embodiment of the proximal manifold connector assembly 670 comprises the extension line 674 having a system control board 676 with remote controls 678 illustrated in FIG. 56. An exemplary embodiment of the remote control 678 is a mechanical slide switch that turns vacuum on or off based upon a longitudinal position. This can be a two position switch with a button for ROAR operation. Alternatively, a three-position switch can be provided. In a forward position, the vacuum is off, in a middle or intermediate position the vacuum is on, and in a rear position ROAR operation takes place. When the remote switch is connected, any control buttons on pump are disengaged but the pump can have an "emergency off" switch on the pump that allows the user to turn off the pump if desired regardless of the operation of the remote controls. LEDs can be provided on the remote controls 678 and/or on the body 601. These LEDs can, for example, be: Red=off, Green=Vacuum on, Blinking Green=ROAR, Blinking Red=Error, Blue=vent/purge. In an exemplary embodiment, a mechanical redundant pinch valve is present against catheter that, when actuated, pinches closed the lumen of the catheter. In the exemplary embodiment, the distal end of the proximal manifold connector assembly 670 that connected to the ROAR catheter 660 comprises a luer lock part that connects to another luer lock part on the ROAR catheter 660. In various exemplary embodiments, the switch is passive (e.g., a simple mechanical switch) or it is an active switch (e.g., capacitive, pressure, magnetic). In such a case, the switch is powered by wires through the extension line 674. In an alternative embodiment, the switch is a separate module that attaches to the extension line 674 and is, for example, battery-powered.

Figure 72:
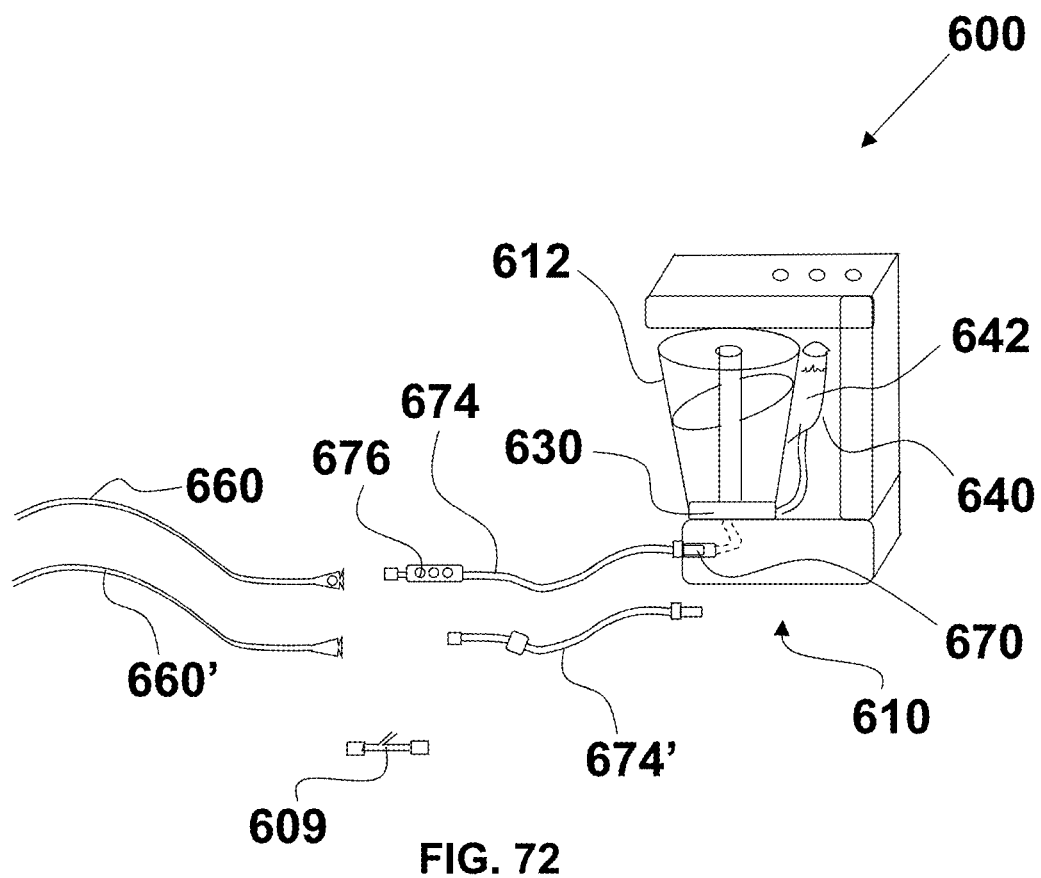
FIG. 72 is a diagrammatic illustrated of an exemplary embodiment of a self-contained, aspiration thrombectomy system.

A first benefit of the aspiration thrombectomy system 600 is that, with such a configuration, the same vacuum source 610 can be used with all catheters that previously could be connected to any surgical aspiration devices/vacuum pumps. A second advantage relates to security for enacting the ROAR effect. In such a configuration, users are persuaded to connect the proximal end of the ROAR catheter 660 to the distal end of the proprietary extension line 674. This is beneficial for various reasons. First, ROAR will not work unless the two unique ROAR parts are directly connected and a positive ROAR ID is established. Second, if a standard rotating hemostasis valve is connected between the ROAR catheter 660 and the extension line 674 (for whatever reason that the surgeon/nurse may have), then identification will be negative and ROAR will be disabled. There is a risk that fluid contained within lumens of such rotating hemostasis valves will enter into the ROAR catheter's fluid column and, thereby, introduce air bubbles, which need to be purged entirely from the system for use. An RHV 609 increases the probability of air remaining in the lumens or entering the fluid system. See FIG. 72. Thus, a particularly desirable configuration for the ROAR catheter 660 is a direct connection between the proximal end of the ROAR catheter 660 and a distal end of the proprietary extension line 674. There is also an issue of safety to ensure that the ROAR effect is utilized only with ROAR catheters 660. As described above, each ROAR catheter 660 has a particular set of characteristics related to compliance and, therefore, operation of the vacuum and vent valves 620, 650 is set for that characteristic set. The system 600 is set to react with a particular ROAR configuration based upon the physical characteristics of the ROAR catheter 600 connected, such as length and lumen size. Therefore, the system 660 is tuned/programmed to store a given ROAR setting for each ROAR catheter 660.

However, it is possible that new ROAR catheters 660 and new ROAR extension lines 674 are created after the system 600 or the controller 700 are put into the field. Providing the identity of the ROAR catheter 660 or the ROAR extension line 674 would, therefore, not be sufficient to permit operation of those components properly. Thus, in an additional or alternative embodiment, each of the ROAR catheters 660 and the ROAR extension lines 674 are provided with a memory device (e.g., a DS28E07 EEPROM memory chip) that, when connected to the system 600, provides the controller 700 with the variables necessary for that ROAR catheter 660 and/or that ROAR extension line 674 to operate with the ROAR effect. Example variables that are stored in the memory of each of the ROAR catheters 660 and the ROAR extension lines 674 include, but are not limited to, the frequency of the waveform cycle, a time in the cycle at which the vacuum turns on (Vacon time 622), a duration of the vacuum (Vacon duration 624), a time in the cycle at which the vacuum turns off (Vacoff time 626), a duration that the vacuum is off (Vacoff duration 628), a time in the cycle at which the vent turns on (Vnton time 652), a duration of the vent (Vnton duration 654), a time in the cycle at which the vent turns off (Vntoff time 656), and/or a duration that the vent is off (Vntoff duration 658). By being able to provide such information to the controller 700, the system 600 can utilize any future ROAR catheter 660 and/or ROAR extension line 674 that might be created for use with the system 600.

An exemplary embodiment of a self-contained aspiration thrombectomy system 600 is shown in FIGS. 57 to 71. The system 600 has an exterior body 601 containing therein a vacuum motor 614, the controller 700, and controls for the vacuum and vent valves 620, 650 (exemplary embodiments of the controls for the valves are shown in FIG. 29 and FIGS. 42 to 46). The vacuum motor 614 is fluidically connected to a collection canister 612 (shown diagrammatically with dashed lines). The body 601 houses a set of system controls 676 (in an alternative embodiment, the controls 676 can be located on/also located on the extension line 674). In this exemplary embodiment, there are three buttons: off, purge, and ROAR/Vac. (The purge function will be described in further detail below.) On a side opposite the collection canister 612 is a vent fluid reservoir 640 (shown diagrammatically with dashed lines) containing therein vent liquid 642. As mentioned above, the fluid path of the catheter 660 is to be free from bubbles/air at all times during a surgical procedure.

The body 601 has cassette connection assembly 602 on a front face thereof. The cassette connection assembly 602 protrudes from the front face and has an exterior shape substantially the same as a cassette 710 that will be attached thereto. The vacuum and vent valves 620, 650 protrude from the front face 608 of the cassette connection assembly 602 and, in an exemplary embodiment, are centered within respective depressions of the cassette connection assembly 602. In this embodiment, the vacuum and vent valves 620, 650 are pistons that have at a distal-most end thereof a pinching structure. In this exemplary embodiment, the pinching structure is substantially in the shape of a standard slot screwdriver. As the vacuum and vent pistons extend out from the depression a given distance (e.g., 8 mm), the slot presses against tubing (in the cassette 710) to close off the lumen within the respective vacuum or vent hose. Closing off the hose acts as a shut-off of the respective valve and releasing away from the hose acts to open the vacuum or vent, respectively. Thus, if the hoses for each of the vacuum and vent lines are placed directly in front of the pistons, the valves 620, 650 will control vacuum and vent according to the ROAR process described herein. (As described below, the cassette 710 positions those hoses in this manner.) In between the valves 620, 650 is a boss 604 protruding from the front face 608 of the cassette connection assembly 602. The boss 604 has an exterior surface with a given shape, e.g., a raceway, and orientation wings 605. At the end of the boss 604 is a rotating lock 606 in the shape of half circle or half oval. The rotating lock 606 has a central pivot to allow it to rotate 90 degrees from the position shown in FIGS. 57 to 67. In the rotated orientation, therefore, the rotating lock 606 defines lower surfaces (opposite the front face 608 of the cassette connection assembly 602) that are perpendicular to the protruding extent of the boss 604. These lower surfaces are set at a distance to define a gap between the lower surface of the rotating lock 606 and the front face 608 of the cassette connection assembly 602. Also present on the front face 608 of the cassette connection assembly 602 is/are conductive connectors 618. The conductive connectors 618 are used to detect when a cassette 710 is present and locked on the cassette connection assembly 602. Detection of the cassette 710 can be made by mechanical measures (such as a pogo pin) or a combination of mechanical and optical and electrical measures.

Figure 68:
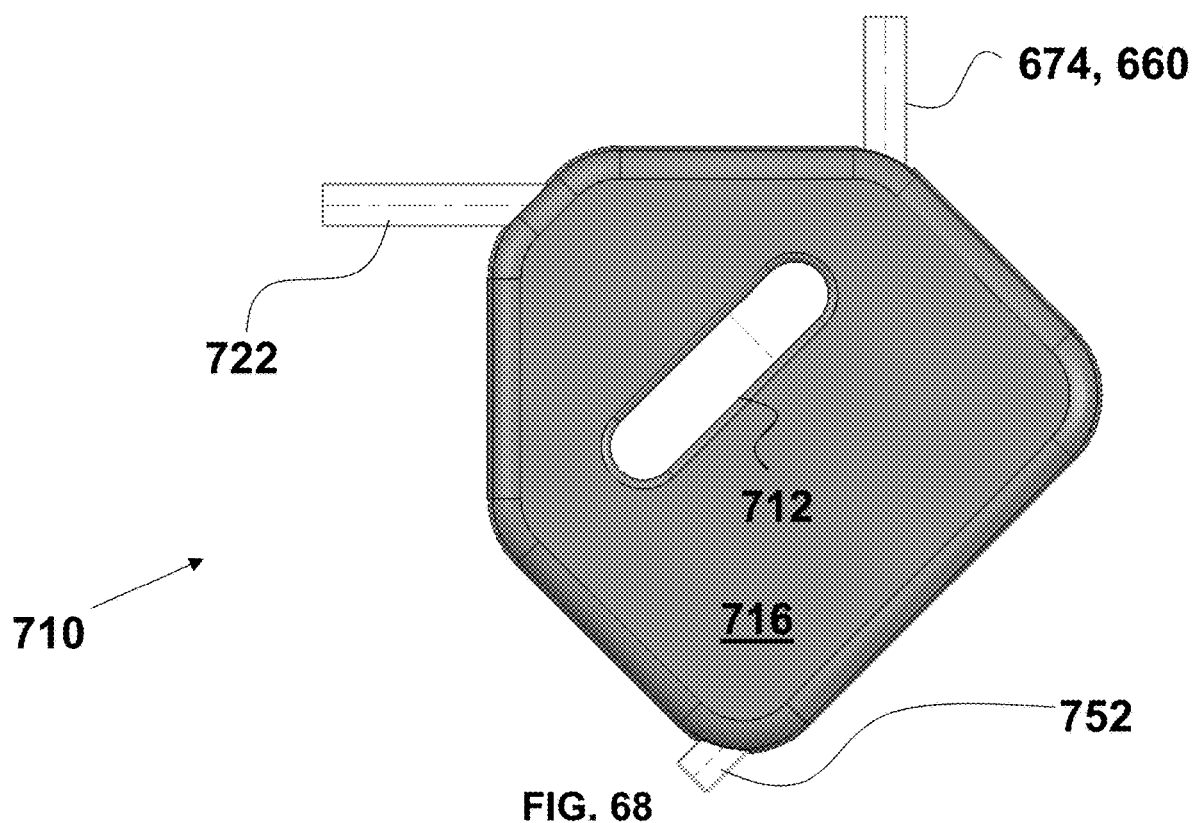
FIG. 68 is a top plan view of an exemplary embodiment of a valve cassette for the systems of FIGS. 57 to 67 with hidden line views of fluid lumens.
Figure 69:
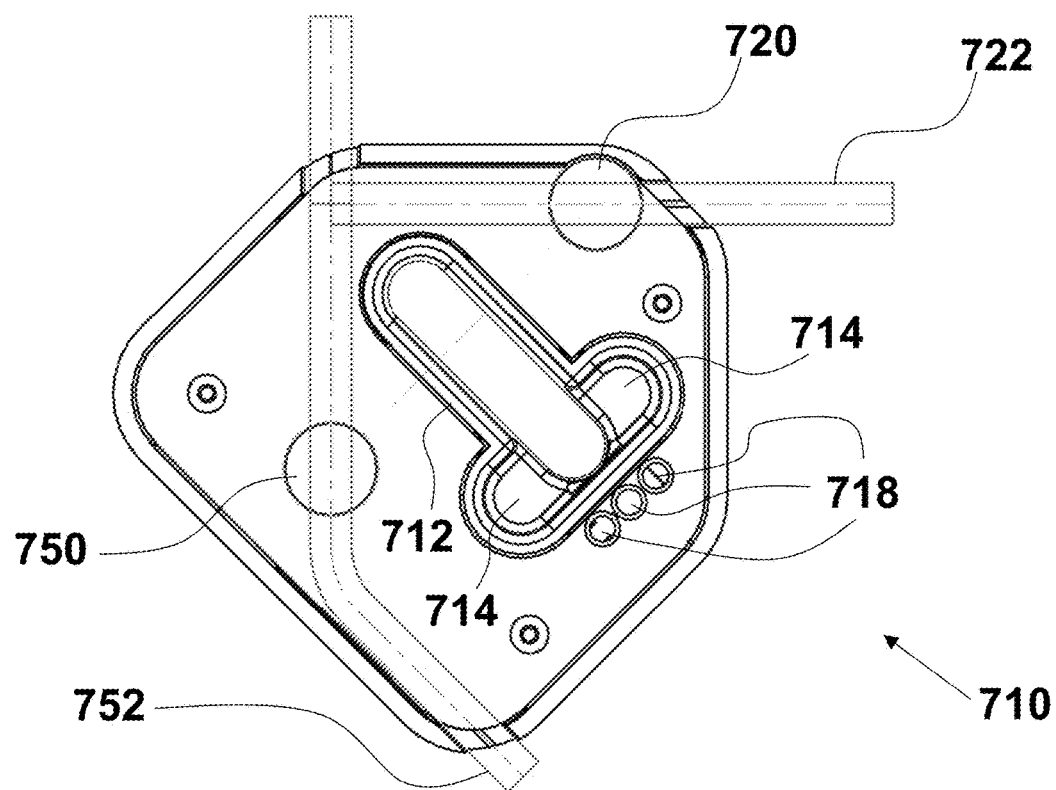
FIG. 69 is a bottom plan view of the valve cassette of FIG. 69.
Figure 70:
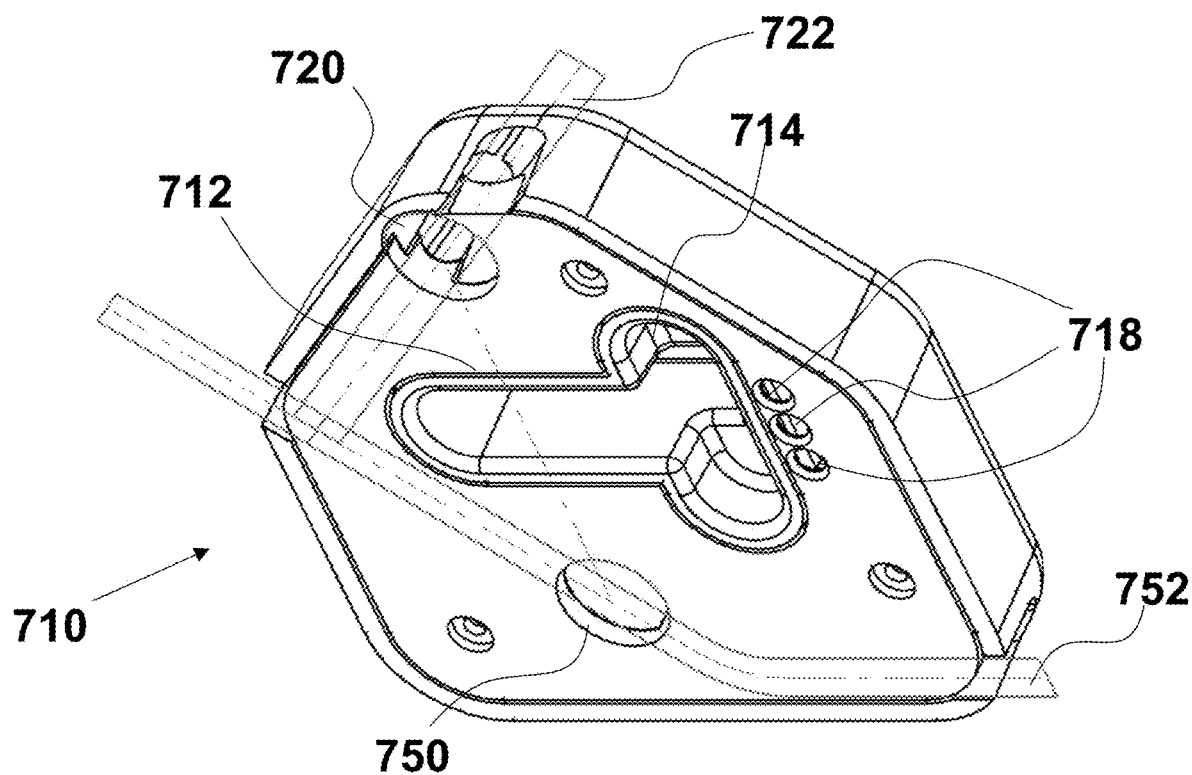
FIG. 70 is a bottom perspective view of the valve cassette of FIG. 69.
Figure 71:
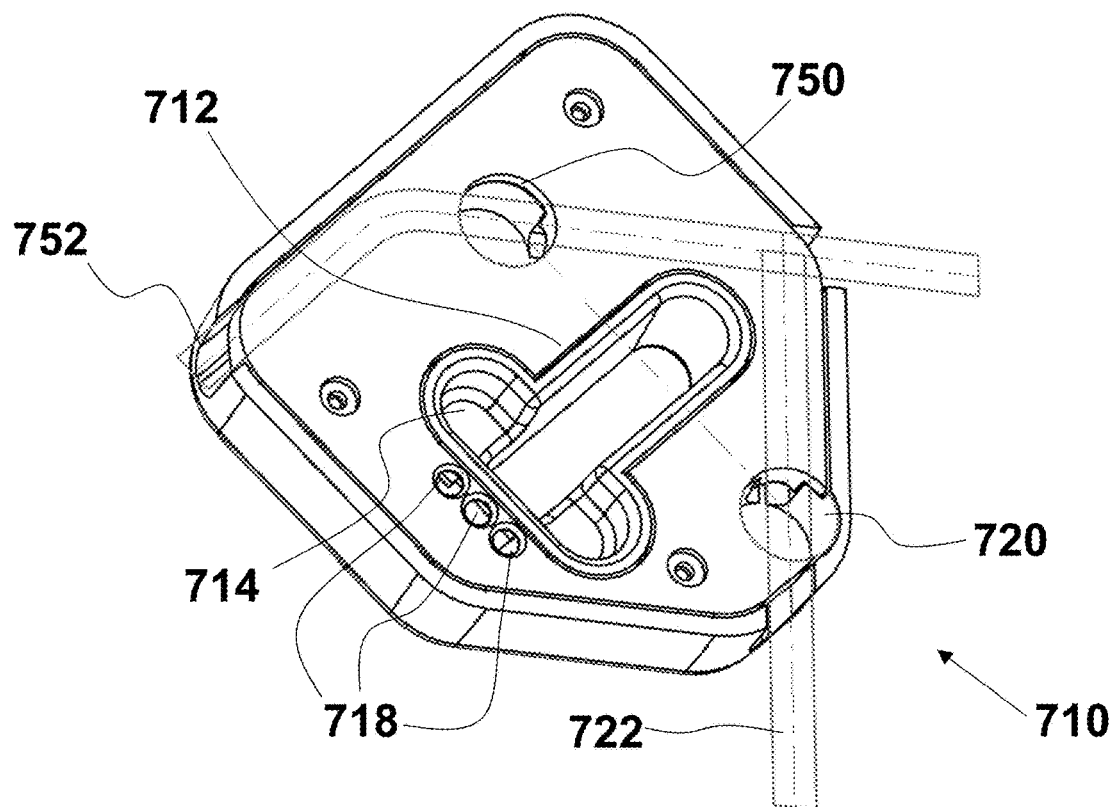
FIG. 71 is a bottom perspective view of the valve cassette of FIG. 69.

A cassette 710 is removably connected to the cassette connection assembly 602 and an exemplary embodiment of this cassette 710 is illustrated in FIGS. 68 to 71. As shown in FIG. 68, the cassette 710 has an interior orifice 712 with a shape corresponding to the given shape of the boss 604. The boss 604 and interior orifice are matched in shape so that the cassette 710 can fit onto the boss 604 and slide down thereon until the rear face of the cassette 710 aligns with and/or touches the front face 608 of the cassette connection assembly 602. The rear face of the cassette 710 is depicted in FIG. 69. In the view of FIG. 69, pockets 714 corresponding in shape to the orientation wings 605 are present in the interior surface of the cassette 710 at the interior orifice 712. In this regard, when the cassette 710 is slid down the boss 604, there is only one orientation in which the cassette 710 can approach the front face 608 in a lower-most position e.g., as in a key within a keyhole. This placement insures that the distal end effectors of the vacuum and vent valves 620, 650 are always aligned with vacuum valve area 720 and the vent valve area 750 within the cassette 710.

When the "T" shape of the boss 604 and wings 605 are matched with the interior T-shape of the orifice 712, three connections are made possible. First, as set forth above, the distal end effectors of the vacuum and vent valves 620, 650 are aligned with vacuum and vent valve areas 720, 750 within the cassette 710. Second, conductive connectors 718 on a rear face of the cassette 710 are aligned with and make contact with respective conductive connectors 618 adjacent the boss 604. These connectors 718, 618 can be, for example, respective pads and pogo pins to insure positive electrical connection when the rotating lock 606 is used to lock the cassette 610 onto the body 611. With appropriate electrical connections, these connectors 718, 618 can inform the controller 700 that the cassette 710 is installed and ready for use and which kind of cassette 710 is installed if it is associated with a particular ROAR catheter 660 and needs identification. Finally, the rotating lock 606 is located above the front face 608 of the cassette connection assembly 602 and the bottom surfaces of the rotating lock 606 are above the outer front face 716 of the cassette 710. A protrusion distance of the boss 604 is configured to place bottom surfaces of the rotating lock 606 (those surfaces facing the front face 608) at a distance approximately equal to the thickness of the cassette 710 such that, with rotation of the lock 606, the bottom surfaces of the lock 606 engage the outer front face 716 of the cassette 710, thereby pressing the cassette 710 firmly in place against the front face 608 to touch the connectors 718, 618 together and locking the cassette 710 to the body 601. The quarter-turn rotating lock 606 secures the cassette 710 on the body 601 and also provides a cam force that holds the cassette 710 thereon, in particular, while the valves 620, 650 actuate against vacuum and vent tubing present within the cassette 710. In an exemplary embodiment, a non-illustrated switch is integrated in the rotating lock 606, the switch detecting the quarter-turn and, with the electrical connectors 718, 618, verifying that the system 600 is armed and ready for use.

In a particularly efficient configuration, the cassette 710 can be removable, replaceable, and disposable as an entire set including the junction box shown in FIGS. 68 to 71 and a tubing set. The cassette 710 has as set of relatively short whips of tubing including a first tubing whip 722 fluidically connected to the collection canister 612 of the vacuum source 610 and a second tubing whip 752 fluidically connected to an intake of the vent valve 650, and an extension whip that can be the extension line 674 or it can be a short tubing to be connected directly to the catheter 660. Once connected, this efficient configuration allows the system of lumens to be automatically cleared of air/bubbles. By locating the vent liquid above all of the lumens (such as with the bag 640 in FIG. 67), the catheter 660, and the collection canister, opening the output of the vent fluid reservoir 640 will fill all interior lumens and clear the system of any air/bubbles before use. If desired, a cam lock can be mechanically connected to the vacuum motor 614 (either temporarily or fixed) and the motor 614 can be operated to actively draw all air into the collection canister and thereby purge the system 600. As an alternative to the front-loaded configuration of the cassette 710, the cassette 710 can be connected or molded as a part of a bottom of the disposable collection canister 612. In this configuration, two disposable parts can be provided together in a sterile packaging and disposed of in one piece. With a vent fluid reservoir that is either a hard container (FIGS. 57 to 61) or a bag (FIGS. 62 to 67), the vent liquid 642 can be part of the cassette 700 with all lumens pre-filled with saline and part of a single disposable package. The vent fluid reservoir 640 and the collection canister 612 can either or both be part of a disposable cassette 700 system. All of the disposable parts used in a catheter procedure can be integrated together in one disposable package.

As explained previously, it is important for the system to be purged of air to achieve the ROAR effect. Purging can be achieved in several ways. The two main methods used to purge the system are forced purged and dribble purge. The forced purge method involves submerging the tip of the extension line 674 into sterile fluid such as saline and while submerged activating the "purge" function. The controller 700 will then alternatively open one or both of the control valves for a predetermined time and sequence to pull the sterile fluid through the extension line 674 and valves and displace all the air that may have been in the system. Once this purge process is complete, both valves will close and the extension line 674 with a full fluid column can be connected to the catheter which has also be de-aired and ROAR applied. In comparison, the dribble method relies on a small positive pressure (created by gravity, squeezing the fluid bag, pressurizing the vent fluid tank, or a peristaltic pump or any similar measures) to allow the vent fluid to dribble through the lumens and, thus, flood them. In an exemplary case of the dribble purge system, the vent fluid source 640 is higher than the exit of the extension line 674 and the vent liquid path does not contain any air traps.

For the dribble method, the purge cycle is initiated by pressing the purge button and, in an exemplary embodiment, is performed by the controller 700. With the vacuum valve 620 closed, the vacuum source 610 is turned on and the vacuum vessel is pumped down to a desired vacuum level. The vent valve 650 is opened and vent liquid 642 is allowed to flood the vent line and the extension line 674. To ensure that all air is removed from the manifold 630, the vacuum valve 620 is opened momentarily while the vent valve 650 is also open. This allows the vent liquid 642 to be drawn from the vent fluid source 640 and from the extension line 674, and through the vacuum manifold passageways thus purging them of air. The vent valve 650 is left open for a period of time after the vacuum valve 620 closes to ensure that the quantity of fluid that the vacuum cycle removed from the extension line 674 is replenished. This cycle of vent liquid flow and momentary vacuum can be repeated several times to ensure complete purging. The purge pump can be a peristaltic pump, a pressurized cuff around a flexible vent liquid container (such as an IV bag), and/or a vent fluid canister pressurized by using the exhaust from the vacuum source 610.

The presence of bubbles in the fluid system adversely affects the water-hammer effect. Accordingly, the system 600 facilitates or automatically purges air from the fluid lumens. In an exemplary embodiment, bubble sensors (either optical, ultrasonic, or fluid-pressure-profile based) are incorporated into the system 600 to facilitate this purging or to automatically engage a purging function (e.g., under operator control to prevent purging when the catheter 660 is present in the bloodstream). There are various measures for bubble detection. For example, an optical sensor could be placed in the cassette 710 to sense the presence of bubbles. With a sensor coupled to the vacuum source 610, a slow rise in pressure can be sensed to prevent using the incorrect catheter or extension. The specific compliance of a catheter 660 or an extension line 674 is among the parameters used to program or compensate the system 600. A user-feedback indication informs the user when the system has been sufficiently purged. In an exemplary embodiment, the compliance of the catheter 660 and the extension line 674 are controlled to be below some optimum range. Also, pressure-rise information is used to modify the ROAR settings, for example, to detect corking and provide an optimum pressure profile for that condition.

The exemplary configurations of the aspiration thrombectomy system 600 described and shown provide various significant benefits. Before describing these additional benefits, reference is made to FIG. 72, which illustrates one exemplary embodiment of the aspiration thrombectomy system 600 with extension lines 674, and catheters 660. The aspiration thrombectomy system 600 comprises the vacuum source 610 with the collection canister 612, the vent liquid reservoir 640 with the vent liquid 642, the manifold 630, and the proximal manifold connector assembly 670. Removably connected to the proximal manifold connector assembly 670 is a ROAR extension line 674. Next to the ROAR extension line 674 is an off-the-shelf extension line 674' usable both with the system 600 by connecting through the proximal manifold connector assembly 670 and with conventional surgical vacuum sources. The ROAR extension line 674 comprises the system controls 676, which are also shown on a top surface of a frame of the system 600. Also shown is a ROAR catheter 660 and an off-the-shelf aspiration catheter 660'. With proximal Luer connectors, both catheters 660, 660' can be used with either extension line 674, 674'.

There are several topologies for the disposable, reusable, and limited-reuse components of the aspiration thrombectomy system 600 as described and shown herein. The vacuum source 610 can be a limited-reuse component that plugs into a reusable electronics/power-supply system, such as the frame in FIG. 72. The valve-element cassette 710 includes pinch-tubes and, therefore, it is a single-use only component. Alternatively, the valving components can be reusable, for example, where the valve actuator is separate, either in a separate semi-reusable module, or part of the pump/control system. The different kinds of valves (e.g., rotary, trumpet) that have different ways to separate the disposable/reusable portions of the system 600. The valve actuators can be part of a reusable portion or part of a limited-reuse portion (e.g., along with a pump module). Alternatively, the valve-actuators can be a second limited-reuse module. The cassette 710 with the valve elements can include a diaphragm or piston that is actuated by a mechanical actuator in the reusable part of the system 600. With such modularity, the architecture of the system 600 becomes adaptable to use with any vacuum source, even a household vacuum system (which could include a vacuum pressure regulator to ensure uniformity of the system 600. The power source for the system 600 may be a rechargeable battery or a replaceable module attached to the system 600, in which case the latter does not require sterility. Alternatively, the power source is a primary battery included as part of the disposable components, which could include disposable pumping elements.

The various configurations permit multiple product topologies specifically targeted at different use cases. For example, one topology is a minimum-recurring-cost system with only the tubing set being disposable. Alternatively, another topology is a system requiring minimum capital cost and incorporating modules whose costs are easily amortized for each surgical case.

Various additional safety measures can be added to the system 600. For example, a liquid level detector can be provided at or with the vent fluid reservoir 640 to confirm that vent liquid 642 is within the tank or pouch, to indicate a warning to the user when the level of vent liquid is low, and to prevent operation of the system 600 if the vent liquid about to run out or is empty. In the configurations with the cassette 710, the system 600 will not start unless the cassette 710 is in place and is correctly installed. The system 600 can have a purging function that is used to fill the various lumens of the catheter 660, the extension line 674, and any tubing connecting the vent fluid reservoir 640 and the collection canister 612 before use. It is noted that the system 600 should not be operated if air is present anywhere in the lumens. Thus, the controller 700 can operate the system to draw in vent liquid 642 and fill the various lumens in a pre-use setup phase. This could include having the vacuum motor 614 operate in reverse to apply positive pressure for purging the various lumens. Alternatively, the controller 700 could actuate a peristaltic pump to purge vent fluid through the lumens. The controller 700 can be programmed, during operation of the system 600, to detect peaks of use during ROAR. If these peaks are not sharp, then a conclusion that air is present in the system can be determined. Bubble detectors (i.e., ultrasonic) can be added to the system such that they straddle the tubing in the cassette and provide feedback to the controller to ensure that the tubing has been properly purged. With such a conclusion, the controller 700 can be programmed to cease operation and start an auto-purge routine to flush the various lumens with an external liquid source or from the vent fluid reservoir 640.

It is noted that various individual features of the inventive processes and systems may be described only in one exemplary embodiment herein. The particular choice for description herein with regard to a single exemplary embodiment is not to be taken as a limitation that the particular feature is only applicable to the embodiment in which it is described. All features described herein are equally applicable to, additive, or interchangeable with any or all of the other exemplary embodiments described herein and in any combination or grouping or arrangement. In particular, use of a single reference numeral herein to illustrate, define, or describe a particular feature does not mean that the feature cannot be associated or equated to another feature in another drawing figure or description. Further, where two or more reference numerals are used in the figures or in the drawings, this should not be construed as being limited to only those embodiments or features, they are equally applicable to similar features or not a reference numeral is used or another reference numeral is omitted.

The foregoing description and accompanying drawings illustrate the principles, exemplary embodiments, and modes of operation of the systems, apparatuses, and methods. However, the systems, apparatuses, and methods should not be construed as being limited to the particular embodiments discussed above. Additional variations of the embodiments discussed above will be appreciated by those skilled in the art and the above-described embodiments should be regarded as illustrative rather than restrictive. Accordingly, it should be appreciated that variations to those embodiments can be made by those skilled in the art without departing from the scope of the systems, apparatuses, and methods as defined by the following claims.

What is claimed is:

1. A clot removal system, comprising:
   a catheter:
      comprising a proximal end, a distal end, and controller operating parameters; and
      defining a lumen configured to be filled with a liquid column having a proximal portion;
   a vacuum source configured to supply vacuum; and
   a controller:
      configured to carry out a control pattern of turning on and off the vacuum based upon the controller operating parameters; and
      configured to receive the controller operating parameters in an automatic response to the catheter being operatively connected to at least one of the vacuum source and the controller and, responsive to the connection, to carry out the control pattern to change a level of vacuum at the distal end of the catheter.

2. The system according to claim 1, wherein the controller operating parameters are stored in the catheter and are provided to the controller responsive to the connection.

3. The system according to claim 1, wherein the catheter comprises an extension line:
   having a first end connected to the catheter and a second end connected to at least one of the vacuum source and the controller; and
   comprising the controller operating parameters and, responsive to the connection:
      configured to provide the controller operating parameters to the controller; and
      fluidically connecting the proximal end of the catheter with the vacuum source.

4. The system according to claim 3, wherein:
   the controller is part of the vacuum source; and
   the controller is configured to receive the controller operating parameters in the automatic response to the catheter being operatively connected to the vacuum source.

5. The system according to claim 3, wherein:
   the controller is separate from the vacuum source; and
   the controller is configured to receive the controller operating parameters in the automatic response to the catheter being operatively connected to the controller.

6. The system according to claim 3, wherein the extension line comprises an identification subassembly including system controls for operating the aspiration thrombectomy system.

7. The system according to claim 3, wherein one of:
   the controller is part of the vacuum source and the extension line fluidically connects the proximal end of the catheter to the vacuum source; and
   the controller is separate from the vacuum source and is removably coupleable to the vacuum source and the extension line fluidically connects the proximal end of the catheter to the controller.

8. The system according to claim 3, further comprising an identification sub-assembly disposed at the connection between the catheter and the extension line.

9. The system according to claim 8, wherein the identification sub-assembly is at least one of:
   an inductive sensor and sensed part;
   an RFID tag and reader;
   an NFC tag and reader;
   a 1-wire detection system;
   a 2-wire detection configuration;
   a Bluetooth low energy device;
   metallic touch pads;
   at least one passive resistor configuration; and
   at least one hall sensor.

10. The system according to claim 8, wherein the identification sub-assembly is at least one of:
    a manual user interface in which a user communicates to the controller which controller operating parameters to use with the catheter;
    a QR code and a QR code reader in which the QR code provided with the catheter communicates to the controller which controller operating parameters to use with the catheter;
    a bar code and a bar code reader in which the bar code provided with the catheter communicates to the controller which controller operating parameters to use with the catheter; and
    a punch-card and a punch-card reader in which the punch-card provided with the catheter communicates to the controller which controller operating parameters to use with the catheter.

11. The system according to claim 8, wherein the identification
    sub-assembly comprises a reader disposed at least at:
       the vacuum source; and/or
       the controller.

12. The system according to claim 3, wherein the operative connection of at least one of the catheter and the extension line to the at least one of the vacuum source and the controller is an identification sub-assembly.

13. The system according to claim 1, wherein:
    the controller operating parameters comprise a catheter identifier; and
    the controller is configured to receive the catheter identifier in the automatic response to the catheter being operatively connected to at least one of the vacuum source and the controller and, responsive to the connection, to carry out a pre-determined control pattern associated with the catheter identifier to change the level of vacuum at the distal end of the catheter.

14. The system according to claim 13, wherein:
    the controller is part of the vacuum source; and
    the controller is configured to receive the catheter identifier in the automatic response to the catheter being operatively connected to the vacuum source.

15. The system according to claim 13, wherein:
    the controller is separate from the vacuum source; and
    the controller is configured to receive the catheter identifier in the automatic response to the catheter being operatively connected to the controller.

16. The system according to claim 1, wherein:
    the controller operating parameters comprise a catheter identifier; and the catheter comprises an extension line:
having a first end connected to the catheter and a second end connected to at least one of the vacuum source and the controller;
comprising the catheter identifier; and
responsive to the connection, the extension line:
is configured to provide the catheter identifier to the controller; and
fluidically connects the proximal end of the catheter with the vacuum source.

17. The system according to claim 16, wherein:
the controller is part of the vacuum source; and
the controller is configured to receive the catheter identifier in the automatic response to the extension line being operatively connected to the vacuum source.

18. The system according to claim 16, wherein:
the controller is separate from the vacuum source; and
the controller is configured to receive the catheter identifier in the automatic response to the extension line being operatively connected to the controller.

19. The system according to claim 1, wherein the controller is configured to repeatedly and periodically carry out the control pattern.

20. The system according to claim 1, wherein the controller is one of a mechanical valve controller and an electronic valve controller.

21. The system according to claim 1, which further comprises an identification subassembly including a sensed part configured to be operatively connected to the catheter and, responsive to sensing the sensed part, the controller carries out the control pattern.

22. The system according to claim 1, wherein the operative connection of the catheter to the at least one of the vacuum source and the controller is an identification sub-assembly.

23. The system according to claim 1, wherein:
the catheter comprises an extension line having a first end connected to the catheter and a second end opposite the first end; and
the operative connection of the catheter is an identification sub-assembly comprising a reader disposed at least at:
the extension line;
the vacuum source; and/or
the controller.

24. A clot removal system, comprising:
a catheter:
comprising a proximal end, a distal end, and controller operating parameters; and
defining a lumen configured to be filled with a liquid column having a proximal portion;
a vacuum source configured to supply vacuum;
a vacuum modulator configured to fluidically communicate:
with the vacuum from the vacuum source; and
with the proximal portion of the liquid column at the proximal end of the catheter; and
a controller:
configured to carry out a control pattern of modulating the vacuum modulator based upon the controller operating parameters; and
configured to receive the controller operating parameters in an automatic response to the catheter being operatively connected to at least one of the vacuum modulator and the controller and, responsive to the connection, to carry out the control pattern to change a level of vacuum at the distal end of the catheter.

25. The system according to claim 24, further comprising:
a manifold comprising the vacuum modulator and an output; and
an extension line fluidically connecting the proximal end of the catheter to the output of the manifold.

26. The system according to claim 24, wherein the controller is configured to repeatedly and periodically carry out the control pattern.

27. The system according to claim 24, which further comprises an extension line:
operatively connected to at least one the vacuum modulator and the controller; and
fluidically connecting the proximal end of the catheter to at least one the vacuum modulator and the controller.

28. The system according to claim 24, wherein the operative connection of the catheter to the at least one of the vacuum modulator and the controller is an identification sub-assembly.

29. A clot removal system, comprising:
a catheter:
comprising a proximal end, a distal end, and controller operating parameters; and
defining a lumen configured to be filled with a liquid column having a proximal portion;
a vacuum source configured to supply vacuum;
a vent container holding a vent liquid;
a vent valve configured to fluidically communicate:
with the vent liquid in the vent container; and
with the proximal portion of the liquid column at the proximal end of the catheter;
a vacuum valve configured to fluidically communicate with:
the vacuum source; and
the proximal portion of the liquid column at the proximal end of the catheter; and
a controller:
configured to carry out a control pattern of opening and closing the vent and vacuum valves based upon the controller operating parameters; and
configured to receive the controller operating parameters in an automatic response to the catheter being operatively connected to at least one of the vent valve, the vacuum valve, the vacuum source, and the controller and, responsive to the connection, to carry out the control pattern to change a level of vacuum at the distal end of the catheter.

30. The system according to claim 29, wherein a portion of the control pattern includes a time period where both the vent and vacuum valves are closed.

31. The system according to claim 29, wherein the controller is configured to repeatedly and periodically carry out the control pattern with the vent and vacuum valves.

32. The system according to claim 29, wherein the controller is configured to open and close the vent and vacuum valves in a repeated cycle comprising a vent-only state in which the vacuum valve is closed and the vent valve is open, and a time of the vent-only state is no greater than 50 ms.

33. The system according to claim 29, wherein:
the lumen has a diameter of between approximately 0.038" and approximately 0.106"; and
the controller is configured to repeatedly and periodically carry out the control pattern of opening and closing the vent and vacuum valves at a frequency of between approximately 2 Hz and approximately 16 Hz.

34. The system according to claim 29, which further comprises an extension line:

operatively connected to at least one of the vent valve, the vacuum valve, and the controller; and fluidically connecting the proximal end of the catheter to at least one of the vent valve, the vacuum valve, and the controller.

35. The system according to claim 34, wherein the operative connection of the catheter to the at least one of the vent valve, the vacuum valve, the vacuum source, and the controller is an identification sub-assembly.

* * * * *

UNITED STATES PATENT AND TRADEMARK OFFICE
CERTIFICATE OF CORRECTION

PATENT NO. : 12,059,161 B2
APPLICATION NO. : 16/899514
DATED : August 13, 2024
INVENTOR(S) : Derek Dee Deville et al.

Page 1 of 2

It is certified that error appears in the above-identified patent and that said Letters Patent is hereby corrected as shown below:

On the Title Page

Page 4, Column 1, under "Other Publications", Line 17, delete "tequenique" and insert -- technique --.
Page 4, Column 1, under "Other Publications", Line 17, delete "Neurolintervent" and insert -- NeuroIntervent --.
Page 4, Column 1, under "Other Publications", Line 24, delete "534" and insert -- 534. --.
Page 4, Column 1, under "Other Publications", Line 30, delete "Endthelium" and insert -- Endothelium --.
Page 4, Column 2, under "Other Publications", Line 16, delete "Fragented" and insert -- Fragmented --.
Page 4, Column 2, under "Other Publications", Line 22, delete "thrombectormy" and insert -- thrombectomy --.
Page 4, Column 2, under "Other Publications", Line 58, delete "Artiries" and insert -- Arteries --.
Page 4, Column 2, under "Other Publications", Line 63, delete "therombectomy" and insert -- thrombectomy --.
Page 5, Column 1, under "Other Publications", Line 15, delete "pateient" and insert -- patient --.
Page 5, Column 1, under "Other Publications", Line 16, delete "watchmana" and insert -- watchman --.
Page 5, Column 1, under "Other Publications", Line 16, delete "exprerience," and insert -- experience, --.
Page 5, Column 1, under "Other Publications", Line 29, delete "Trhombi" and insert -- Thrombi --.
Page 5, Column 1, under "Other Publications", Line 30, delete "(Struttgar)" and insert -- (Stuttgart) --.
Page 5, Column 1, under "Other Publications", Line 54, delete "NeuraIntervent" and insert -- NeuroIntervent --.
Page 5, Column 2, under "Other Publications", Line 3, delete "NeuraIntervent" and insert -- NeuroIntervent --.
Page 5, Column 2, under "Other Publications", Line 7, delete "NeuraIntervent" and insert -- NeuroIntervent --.
Page 5, Column 2, under "Other Publications", Line 11, delete "NeuraIntervent" and insert -- NeuroIntervent --.

Signed and Sealed this
Second Day of December, 2025

John A. Squires
*Director of the United States Patent and Trademark Office*

Page 5, Column 2, under "Other Publications", Line 19, delete "NeuraIntervent" and insert -- NeuroIntervent --.

In the Specification

In Column 3, Line 29, delete "hereinafore" and insert -- hereinbefore --.
In Column 4, Line 22, delete "context" and insert -- context. --.
In Column 16, Line 42, under "Brief Description of the Drawings", delete "of FIG.".
In Column 20, Line 47, delete "tum," and insert -- turn, --.
In Column 20, Lines 66-67, delete "know to be" and insert -- known to be --.
In Column 24, Line 53, delete "that that" and insert -- that --.
In Column 25, Lines 57-58, delete "cross-sectional sectional" and insert -- cross-sectional --.